US006451543B1

(12) United States Patent
Kochendoerfer et al.

(10) Patent No.: US 6,451,543 B1
(45) Date of Patent: Sep. 17, 2002

(54) LIPID MATRIX-ASSISTED CHEMICAL LIGATION AND SYNTHESIS OF MEMBRANE POLYPEPTIDES

(75) Inventors: Gerd. G. Kochendoerfer, Oakland; Christie L. Hunter, San Francisco; Stephen B. H. Kent, San Francisco; Paolo Botti, San Francisco, all of CA (US)

(73) Assignee: Gryphon Sciences, South San Francisco, CA (US)

(*) Notice: Subject to any disclaimer, the term of this patent is extended or adjusted under 35 U.S.C. 154(b) by 0 days.

(21) Appl. No.: 09/384,302

(22) Filed: Aug. 26, 1999

Related U.S. Application Data

(63) Continuation-in-part of application No. 09/263,971, filed on Mar. 5, 1999, now abandoned, which is a continuation-in-part of application No. 09/144,964, filed on Aug. 31, 1998, now abandoned.

(51) Int. Cl.[7] .............................................. G01N 33/53
(52) U.S. Cl. ..................... 435/7.1; 435/7.1; 435/870; 530/359; 530/400; 530/334; 530/402; 530/404; 530/408; 436/87; 436/88; 436/89; 436/90; 436/501; 436/544; 424/450
(58) Field of Search ................................ 530/359, 400, 530/334, 402, 404, 408; 436/87, 88, 89, 90, 501, 544; 435/810, 701; 424/450

(56) References Cited

U.S. PATENT DOCUMENTS

| | | | |
|---|---|---|---|
| 4,374,120 A | 2/1983 | Soini et al. | 436/546 |
| 4,868,103 A | 9/1989 | Stavrianopoulos et al. | 435/5 |
| 5,162,109 A | 11/1992 | Rajagopalan et al. | 424/1 |
| 5,254,477 A | 10/1993 | Walt | 436/172 |
| 5,288,517 A | 2/1994 | Kanno et al. | 427/244 |
| 5,525,232 A | 6/1996 | Veiro et al. | 210/643 |
| 5,552,155 A | 9/1996 | Bailey et al. | 424/450 |
| 5,585,235 A | 12/1996 | Brocia | 435/4 |
| 5,618,735 A | 4/1997 | Saul et al. | 436/518 |
| 5,622,872 A | 4/1997 | Ribi | 436/518 |

FOREIGN PATENT DOCUMENTS

| | | |
|---|---|---|
| WO | WO 95/00846 | 1/1995 |
| WO | WO 96/03427 | 2/1996 |
| WO | WO 96/34876 | * 11/1996 |
| WO | WO 96/34878 | 11/1996 |
| WO | WO 98/28434 | 7/1998 |

OTHER PUBLICATIONS

Bechinger et al., Towards Membrane Protein Design: pH–sensitive Topology of Histidine–containing Polypeptides, J. Mol. Biol. (1996) 263:768–775.*
Bear et al., "Purification and Functional Reconstitution of the Cystic Fibrosis Transmembrane Conductance Regulator (CFTR)," Cell, 68:809–818, (1992).
El–Jammal et al., "Electrochemical Oxidation of Some Therapeutic 3–Hydroxpryidin–4–one iron chelators," Chemical Abstract, 120(4), Abstract No. 40384, (1994).
Hase et al., "Purification and Functional Reconstitution of the Recombinant Large Mechanosensitive Ion Channel (MscL) of *Escherichia coli*," J. Biol. Chem., 270(32):18329–18334, (1995).
Futaki, Peptide Ion Channels: Design and Creation of Function, Chemical Abstract, 129(17), Abstract No. 213827, (1998).
Lazdunski et al., "Voltage–Sensitive Calcium Ion Channels in Skeletal Muscle; Receptor for Calcium Ion Channel Inhibitors," Chemical Abstract, 105(19), Abstract No. 169622, (1986).
Mihara et al., "Artificial Membrane Protein Functionalized with Electron Transfer System," Chemistry Letters, 3:187–188, (1996).
Paliwal et al., "Purification and Patch Clamp Analysis of a 40–pS Channel from Rat Liver Mitochondria," Biochem., 31:2223–2229, (1992).
Rehm et al., "Overexpression of AlgE in *Escherichia coli*: Subcellular Localization, Purification and Ion Channel Properties," 122(1), Abstract No. 5031, (1995).
Buckholz, R.G., "Yeast Systems for the Expression of Heterologous Gene Products," Current Opinion in Biotech., vol. 4:538–542 (1993).
Broudy, V.C., et al., "Analysis of c–kit Receptor Dimerization by Fluorescence Energy Transfer," Blood, vol. 91:898–906 (1998).

(List continued on next page.)

Primary Examiner—Karen Cochrane Carlson
Assistant Examiner—Hope A. Robinson
(74) Attorney, Agent, or Firm—Jeffrey I. Auerbach; Liniak, Berenato, Longacre & White, LLC

(57) ABSTRACT

The present invention relates to methods and compositions for lipid matrix-assisted chemical ligation and synthesis of membrane polypeptides that are incorporated in a lipid matrix. The invention is exemplified in production of a prefolded membrane polypeptide embedded within a lipid matrix via stepwise chemoselective chemical ligation of unprotected peptide segments, where at least one peptide segment is embedded in a lipid matrix. Any chemoselective reaction chemistry amenable for ligation of unprotected peptide segments can be employed. Suitable lipid matrices include liposomes, micelles, cell membrane patches and optically isotropic cubic lipidic phase matrices. Prefolded synthetic and semi-synthetic membrane polypeptides synthesized according to the methods and compositions of the invention also permit site-specific incorporation of one or more detectable moieties, such as a chromophore, which can be conveniently introduced during synthesis. The methods and compositions of the invention have multiple uses. For example, they can be used to assay ligand binding to membrane polypeptides and domains comprising a receptor, and thus are extremely useful for structure/function studies, drug screening/selection/design, and diagnostics and the like, including high-throughput applications. The methods and compositions of the invention are particularly suited for FRET analyses of previously inaccessible membrane polypeptides.

33 Claims, 10 Drawing Sheets

OTHER PUBLICATIONS

Chong, S., et al., "Protein Splicing Involving the *Saccharomyces cerevisiae* VMA Intein," J.B.C., vol. 271:22159–22168 (1996).

Chong, S., et al., "Single–column Purification of Free Recombinant Proteins Using a Self–cleavable Affinity Tag Derived from a Protein Splicing Element," Gene, vol. 192:271–281 (1997).

Cload, S.T., et al., "Development of Improved tRNAs for in Vitro Biosynthesis of Proteins Containing Unnatural Amino Acids," Chemistry and Biology, vol. 3:1033–1038 (1996).

Dalgaard, J.Z., et al., "Statistical Modeling and Analysis of the Laglidadg Family of Site–specific Endonucleases and Identification of an Intein that Encodes a Site–specific Endonuclease of the HNH family," Nucleic Acid Res., vol. 25:4626–4638 (1997).

Dawson, P.E., et al., "Synthesis of Proteins by Native Chemical Ligation," Science, vol. 266:776–779 (1994).

Gadella, Jr., T.W.J., and Jovin, T.M., "Oligomerization of Epidermal Growth Factor Receptors on A431 Cells Studied by Time–resolved Fluorescence Imaging Microscopy. A Stereochemical Model for Tyrosine Kinase Receptor Activation," J. of Cell Biology, vol. 129:1543–1558 (1995).

Giorgione, J.R., et al., "Increased Activation of Protein Kinase C with Cubic Phase Lipid Compared with Liposomes," Biochem., vol. 37:2384–2392 (1998).

Grove, A., et al., "Synthetic Peptides and Proteins as Models for Pore–Forming Structure of Channel Proteins," Methods in Enzymology, vol. 207:510–525 (1992).

Guan, X., et al., "Enhancement of Membrane Insertion and Function in a Type IIIb Membrane Protein following Introduction of a Cleavable Signal Peptide," J.B.C., vol. 267:21995–21998 (1992).

Herscovics, A., and Orlean, P., "Glycoprotein biosynthesis in yeast," FASEB, vol. 7:540–550 (1993).

Heyduk, E., et al., "Thiol–reactive, luminescent Europium chelates: luminescence probes for resonance energy transfer distance measurements in biomolecules," Anal. Biochem., vol. 248:216–227 (1997).

Huang, K., et al., "Refolding of an Integral Membrane Protein," J.B.C., vol. 265:3802–3809 (1981).

Inglese, J., et al., "Chemokine Receptor–Ligand Interactions Measured Using Time–Resolved Fluorescence," Biochemistry, vol. 37:2372–2377 (1998).

Joon, K., et al., "Organization of Diphtheria Toxin T Domain in Bilayers: A Site–Directed Spin Labeling Study," Science, vol. 273:810–812 (1996).

Kahn, T.W., and Engelman, D.M., Bacteriorhodopsin Can be Refolded from Two Independently Stable Transmembrane Helices and the Complementary Five–helix Fragment, Biochemistry, vol., 31:6144–6151 (1992).

Larriba, G., "Translocation of Proteins across the Membrane of the Endoplasmic Reticulum: A Place for *Saccharomyces cerevisiae*," Yeast, vol. 9:441–463 (1993).

Lee, J., et al., "Conformational Changes in the Insulin Receptor upon Insulin Binding and Activation as Monitored by Fluoresence Spectroscopy," Biochem., vol. 36:2701–2708 (1997).

Li, M. and Selvin, P.R., "Luminescent polyaminocarboxylate chelates of terbium and Europium. The effect of chelate structure," J. of the American Chemical Society, vol. 117:8132–8138 (1995).

Lindblom, G., and Rilfors, L., "Cubic phases and isotropic structures formed by membrane lipids—possible biological relevance," Biochimica et Biophysica Acta, vol. 988:221–256 (1989).

Luzzati, V., "Structure of the cubic phases of lipid–water systems," Nature, vol. 220–485–488 (1968).

MacKenzie, K.R., et al., "A Transmembrane Helix Dimer: Structure and Implications," Science, vol. 276:131–133 (1997).

Mahal, L.K., et al., "Engineering Chemical Reactivity on Cell Surfaces Through Oligosaccharide Biosynthesis," Science, vol. 276:1125–1128 (1997).

Mathis, G., "Probing Molecular Interactions With Homogenous Techniques Based on Rare Earth Cryptates and Fluorescence Energy Transfer," Clin. Chem., vol. 41:1391–1397 (1995).

Nekrasova, E., et al., "Overexpression, Solubilization and Purification of Rat and Human Olfactory Receptors," Eur. J. Biochem., vol. 238:28–37 (1996).

Oh, J.K., et al., "Organization of Diphtheria Toxin T Domain in Bilayers: A Site–Directed Spin Labeling Study," Science, vol. 273:810–812 (1996).

Portmann, M., et al., "Spectroscopic and Rheological Studies of Enzymes in Rigid Lipidic Matrices: The Case of α–Chymotrypsin in a Lysolecithin/Water Cubic Phase," J. Phy. Chem., vol. 95:8437–8440 (1991).

Razumas, V., et al., "Effects of Distearoylphosphatidylglycerol and Lysozyme on the Structure of the Monoolein–water Cubic Phase: X–ray Diffraction and Raman Scattering Studies," Chemistry and Physics of Lipids, vol. 84:123–138 (1996).

Schnölzer, M., et al., "In situ Neutralization in Boc–chemistry Solid Phase Peptide Synthesis," Int. J. Peptide Protein Res., vol. 40:180–193 (1992).

Terpetschnig, E., et al., "Long–Lifetime Metal–Ligand Complexes as Probes in Biophysics and Clinical Chemistry," Methods in Enzymology, vol. 278:295–321 (1997).

Turcatti, G., et al., "Probing the Structure and Function of the Tachykinin Neurokinin–2 Receptor through Biosynthetic Incorporation of Fluorescent Amino Acids at Specific Sites," J.B.C., vol. 271:19991–19998 (1996).

Turcatti, G., et al., "Characterization of Non–peptide Antagonist and Peptide Agonist Binding Sites on the NK1 Receptor with Fluorescent Ligands," J.B.C., vol. 272:21167–21175 (1997).

Valenzuela, C.F., "Traverse Distance Between the Membrane and the Agonist Binding Sites on the *Torpedo* Acetylcholine Receptor: A Fluorescence Study," Biophys. J., vol. 66:674–682 (1994).

Wallace, C.J., "Peptide Ligation and Snythesis," Curr. Opin. Biotech., vol. 6:403–410 (1995).

Wilken, J., and Kent, S.B.H., "Chemical Protein Synthesis," Curr Opin Biotech., vol. 9:412–426 (1998).

Woods, A.C., et al., "Synergy in Protein Engineering," J.B.C., vol. 271:32008–32015 (1996).

Wu, P., and Brand, L., "Resonance Energy Transfer: Methods and Applications," Analytical Biochem., vol. 218:1–13 (1994).

Wuttke, D.S., et al., "Semisynthesis of Bipyridyl–Alanine Cytochrome c Mutants: Novel Proteins with Enhanced Electron–Transfer Properties," J. Am. Chem. Soc., vol. 115:8455–8456 (1993).

Xu, M., and Perler, F.B., "The Mechanism of Protein Splicing and Its Modulation by Mutation," EMBO J., vol. 15:5146–5153 (1996).

\* cited by examiner

LIPID MATRIX-ASSISTED CHEMICAL LIGATION AND SYNTHESIS OF MEMBRANE POLYPEPTIDES

This application is a CIP of Ser. No. 09/263,971 filed Mar. 5, 1999 which is a CIP of Ser. No. 09/144,964 filed Aug. 31, 1998.

TECHNICAL FIELD

The present invention relates to membrane polypeptides, methods of preparation, and assays that employ them.

BACKGROUND

Cell membranes are made of lipids capable of forming a barrier between aqueous compartments. They consist primarily of a continuous double or bilayer plate of lipid molecules associated with various membrane proteins. The phospholipids, sphingolipids, and glycolipids make up the three major classes of membrane forming lipid molecules. These lipids are amphipathic (amphiphilic) molecules in that they have a hydrophilic (polar) head and a hydrophobic (non-polar) tail. In the aqueous environment of cells, the polar head groups face toward the water while their hydrophobic tail groups interact with each other to create a lamellar bilayer, and to a lessor extent other aggregate structures depending on the lipid composition and conditions. For example, membrane lipids can form a variety of different shapes including spheres (vesicles), rods (tubes) and lamellae (plates) depending on lipid and water content, and temperature. These shapes represent basic units that interact to form two- and three-dimensional lattice matrix structures classified as lamellar phase (e.g., bilayer plate, closed sphere), hexagonal phase (e.g., rod), or cubic phase (e.g., spheres, rods or lamellae connected by aqueous channels) (Lindblom, et al., *Biochimica et Biophysica Acta* (1989) 988:221–256). A cross section of a typical cell membrane bilayer (lamellar phase) of phospholipid can be viewed as having a hydrophobic core region of about 30 Angstroms (Å) with two interfacial regions of about 15 Å each (White, et al., *Curr. Struc. Biol.* (1994) 4:79–86).

Proteins can associate with cell membranes in different ways. Integral membrane proteins contain at least one component that is embedded within the lipid bilayer. The nonpolar segments of these integral membrane proteins, which embed in the lipid bilayer perpendicular to the surface of the membrane, may consist of a hydrophobic region of the polypeptide, a covalently attached fatty acid chain or other types of lipid chains. Peripheral membrane proteins normally associate with the lipid bilayer through non-covalent interactions with these integral membrane proteins. Additionally, some peripheral membrane proteins are located entirely in the aqueous phase, associated with the membrane through a covalently attached fatty acid or lipid chain. The co-translational attachment of a fatty acid chain such as myristic acid to the amino-terminal glycine of a protein through an amide linkage results in localization of the protein to the cytoplasmic face of cellular membranes. Prenyl groups and palmitic acid groups are attached post-translationally via thioether linkages to cysteine residues and also result in localization of proteins to the membrane. These types of covalent attachments are important for function in a wide variety of cell signaling proteins, like the heterotrimetric G proteins (James, et al., Biochemistry (1990) 29(11):2623–2634; Morello, et al., *Biochem. Cell Biol.* (1996) 74(4):449–457; Mumby, S. M., *Curr. Opin. Cell. Biol.* (1997) 9(2):148–154; Resh, M. D., *Cell Signal* (1996) 8(6):403–412; and Boutin, J. A., *Cell Signal* (1997) 9(1):15–35). Glycosylphosphatidylinositol anchors, found at the C-terminus of soluble proteins, result in the attachment of these proteins to the cell surface membrane (Turner, A. J., *Essays Biochem.* (1994) 28:113–127).

The two major classes of known integral membrane proteins are those that insert α-helices into the lipid bilayer, and those proteins that form pores in the lipid bilayer by β-barrel strands (Montal, et al., *Curr. Opin. Stuc. Biol.* (1996) 6:499–510; Grigorieff, et al., *J. Mol. Biol.* (1996) 259:393–42; and Weiss, et al., *J. Mol. Biol.* (1992) 227:493–509). Single membrane spanning proteins, or single-pass membrane proteins, generally have a hydrophobic region that anchors that sequence in the lipid bilayer via an α-helix configuration. Multiple membrane spanning proteins, or multi-pass membrane proteins, result from the polypeptide chain passing back and forth across the lipid bilayer and typically employ α-helix and/or β-barrel structured membrane anchors.

Examples of membrane proteins include membrane-associated receptors, transporter proteins, enzymes, and immunogens. For instance, cell membrane-associated receptors represent a dynamic collection of membrane proteins of particular therapeutic importance. Four basic superfamilies are recognized: the enzyme-linked receptors, the fibronectin-like receptors, the seven transmembrane receptors, and the ion channel receptors. Enzyme-linked receptors represent single-pass membrane proteins, with the basic structure consisting of a single polypeptide traversing the plasma lamella once via an α-helix anchor domain. The extracellular domain of enzyme-linked receptors binds hormone/ligand, while the carboxyl-terminal domain contains a catalytic site that promotes signal transduction via hormone/ligand binding and receptor aggregation.

The fibronectin-like receptors have the same general structure as the enzyme-linked receptors except that no specific catalytic site is represented in the cytoplasmic domain. Class 1 fibronectin-like receptors contain two modified extracellular domains formed from two seven-stranded β-sheets that join at right angles to create a ligand-binding pocket. The class 2 fibronectin-like receptors have a slightly different structure in that they form repeats of five-stranded β-sheets that extend over the hormone like fingers. The class 1 and 2 receptors contain a conserved proline-rich cytosolic juxtamembrane region that constituatively binds soluble tyrosine kinases, which is activated by ligand/hormone-binding and receptor aggregation.

The seven-transmembrane receptors, also called G-protein coupled receptors, serpentine receptors, or heptahelical receptors, represent the largest and most diverse family of membrane receptors identified to date. These receptors mediate sensory and endocrine related signal transduction pathways and are multi-pass membrane proteins having α-helical anchor regions that transverse the membrane seven times. The transmembrane spanning regions for some of these proteins form a small ligand/hormone-binding pocket, while larger binding sites are formed through extended amino terminal regions. Seven-transmembrane receptors also contain one or more intracellular loops that bind and activate G-proteins, which act as second messengers in cells.

The ion channel receptors are represented by the ligand- and voltage-gated channel membrane protein receptors. Ligand-gated ion channels are formed by pentamers of homologous subunits. Each subunit contributes an α-helix toward forming the wall of the channel. Ligand/hormone binding appears to occur between the subunits. The typical voltage-gated channel receptors are homotetramers, with each subunit having six transmembrane α-helices.

Different techniques have been used to study membrane proteins and/or exploit them for therapeutic purposes, diagnostics, and drug screening assays and the like. However, unlike non-membrane proteins, the biggest obstacle in working with membrane proteins is the poor solubility of their hydrophobic polypeptide chains, the difficulty in folding membrane proteins from unfolded polypeptide chains and the difficulty in overexpressing and isolating them in environment suitable for quantitative analyses (Huang, et al., *J. Biol. Chem.* (1981) 256:3802–3809; and Liao, et al., *J. Biol. Chem.* (1983) 258:9949–9955). For example, unfolding and folding whole transmembrane proteins is difficult since they are insoluble in the lipid bilayer in the unfolded form, as well as in the aqueous phase in both their folded and unfolded forms, because of their highly hydrophobic character (Haltia, et al., *Biochimica et Biophysica Acta* (1995) 1241:295–322). This feature of membrane proteins is particularly problematic when attempting to synthesize, label or otherwise manipulate them chemically in a cell free environment. Nevertheless, individual transmembrane segments of membrane proteins have been chemically synthesized via solid phase chemistry, followed by subsequent insertion into membranes and spontaneous assembly of native-like structures with biological activity (Popot, et al., *Biochemistry* (1990) 29:4031–4037; and Grove, et al., *Methods Enzymol.* (1992) 207:510–525). To date, however, solid phase synthesis has been limited to synthesis of only a few short transmembrane peptide segments, since membrane proteins are recalcitrant to standard chemical synthesis techniques.

Establishing access to membrane proteins with site-specific chemical modifications is crucial both for the analysis of structure-function relationships of membrane proteins and for drug discovery. The most important techniques currently employed to achieve this goal are the synthesis of small membrane-spanning peptide fragments of these proteins (Grove, et al., *Methods Enzymology* (1992) 207:510–525; and MacKenzie, et al., *Science* (1997) 276:131–133), chemical modification of existing or engineered cysteine residues (Oh, et al., *Science* (1996) 273:810–812), and in vitro suppression mutagenesis to incorporate unnatural amino acids (Cload, et al., *Chemistry and Biology* (1996) 3:1033–1038; and Turcatti, et al., *J. Biol Chem.* (1996) 271:19991–19998). None of these techniques provides general access to totally synthetic or semi-synthetic membrane proteins containing chemically modified amino acid side-chains, or their production in a quantity sufficient for most biophysical techniques. Additionally, such techniques do not permit modular synthesis and reassembly of membrane-incorporated transmembrane polypeptide segments or domains.

Relevant Literature

Wilken, et al. (*Curr. Opin. Biotech.* (1998) 9(4):412–426) review chemical protein synthesis. Dawson, et al. (*Science* (1994) 266:776–779) disclose chemical synthesis of water-soluble polypeptides by native chemical ligation. Grove, et al. (*Methods in Enzymology* (1992) 207:510–525) disclose Boc-chemistry solid phase synthesis of small pore forming membrane peptides and their subsequent incorporation and activity in a lipid membrane. MacKenzie, et al. (*Science* (1997) 276:131–133) disclose recombinant synthesis and radioactive labeling of the transmembrane domain of glycophorin A and its incorporation and NMR structure in a lipid membrane. Oh, et al. (*Science* (1996) 273:810–812) disclose NMR structure of a diptheria toxin transmembrane domain by chemical modification of existing or engineered cysteine residues with a methanethiosulfate spin label to generate a nitroxide side chain. Turcatti, et al. (*J. Bio. Chem.* (1996) 271:19991–19998) disclose in vitro suppression mutagenesis in Xenopus oocytes to introduce fluorescence-labeled amino acids into the seven transmembrane neurokinin-2 receptor and its incorporation and activity in oocyte membranes. Portman, et al. (*J. Phy. Chem.* (1991) 95:8437–8440) disclose incorporation and activity of α-chymotrypsin and bacteriodopsin in a cubic phase lipid matrix. Giorgione, et al. (*Biochemistry* (1998) 37(8):2384–2392) disclose incorporation and activity of protein kinase C in a cubic lipidic phase matrix and liposome.

SUMMARY OF THE INVENTION

The present invention relates to methods and compositions for lipid matrix-assisted chemical ligation and synthesis of membrane polypeptides, compositions produced by the methods, and assays that employ them. The methods involve contacting a lipid matrix-incorporated membrane polypeptide with a ligation label comprising one or more amino acids, where the polypeptide and label comprise amino acids having unprotected reactive groups capable of chemoselective chemical ligation. A variety of chemoselective chemistries can be used for ligation such as native chemical ligation, oxime-forming ligation, thioester forming ligation, thioether forming ligation, hydrazone forming ligation, thiazolidine forming ligation, and oxazolidine forming ligation. Compositions of the invention include totally synthetic and semi-synthetic lipid matrix-embedded membrane polypeptides that are produced by the lipid matrix-assisted chemical ligation method of the invention.

The present invention further includes a method of forming a lipid matrix-embedded membrane polypeptide comprising a ligation site amenable to chemoselective chemical ligation when treated with a reagent that cleaves the polypeptide directly adjacent to a residue amenable to chemoselective ligation. This aspect of the invention involves contacting a membrane polypeptide that is embedded in a lipid matrix with a reagent that selectively cleaves the polypeptide at a specific site so as to generate a lipid matrix-embedded membrane polypeptide with an unprotected N-terminal or C-terminal residue that is amenable to chemoselective chemical ligation. The cleavage site may occur naturally in the polypeptide or the polypeptide can be engineered to contain one or more such sites.

The present invention also includes a method of detecting a ligand that directly or indirectly interacts with a folded membrane polypeptide embedded in a lipid matrix. This aspect of the invention involves contacting with a ligand, a lipid matrix-embedded synthetic or semi-synthetic membrane polypeptide produced by lipid matrix-assisted chemical ligation, where the ligand and/or the membrane polypeptide comprise a detectable label. The ligands may be derived from any number of sources including naturally occurring ligands and synthetic and semi-synthetic sources, such compound libraries. This method is particularly useful for diagnostic assays, screening new compounds for drug development, and other structural and functional assays that employ binding of a ligand to a prefolded membrane polypeptide.

Also provided is support matrix suitable for screening assays, where the support matrix comprises a detectably labeled lipid matrix-embedded membrane polypeptide attached thereto through a chemical handle. The present invention also provides kits having at least one or more compositions of the invention.

The present invention further provides a method for on-resin labeling a peptide with a chelator-sensitized metal ion probe. The method involves labeling one or more amino acids of a peptide attached to a resin with a zwitterionic chelator moiety label capable of chelating metal ions. Also included is a method to increase the solubility of a zwitterionic chelating agent. This method involves combining an insoluble zwitterionic chelating agent with a solubilizing agent that produces a soluble salt form of the zwitterionic chelating agent. The invention also provides s a composition comprising a soluble salt form of a zwitterionic chelator agent.

The methods and compositions of the invention permit unprecedented access to membrane polypeptides and their site-specific labeling with one or more detectable labels. The methods and compositions also have multiple additional uses. For example, they can be used to assay ligand binding to membrane polypeptides and domains comprising a receptor, and thus are extremely useful for structure/function studies, drug screening/selection/design, and diagnostics and the like, including high-throughput applications. The methods and compositions of the invention are particularly suited for FRET analyses of previously inaccessible membrane polypeptides.

DEFINITIONS

Figure 1:
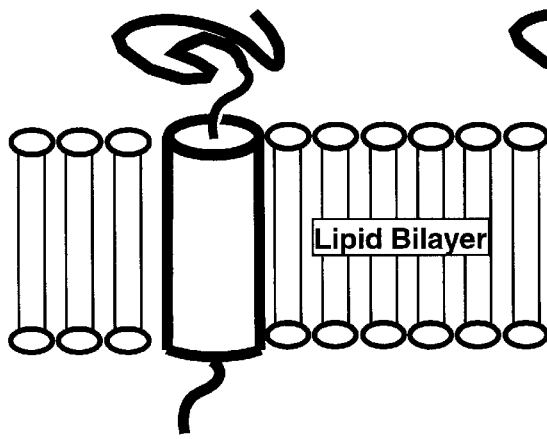
FIGS. 1 A–D illustrates various ways membrane polypeptides associate with a lipid bilayer.
Figure 1:
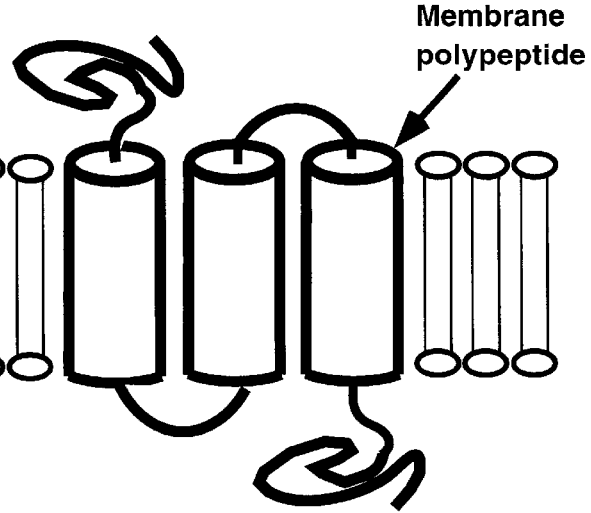
Figure 1:
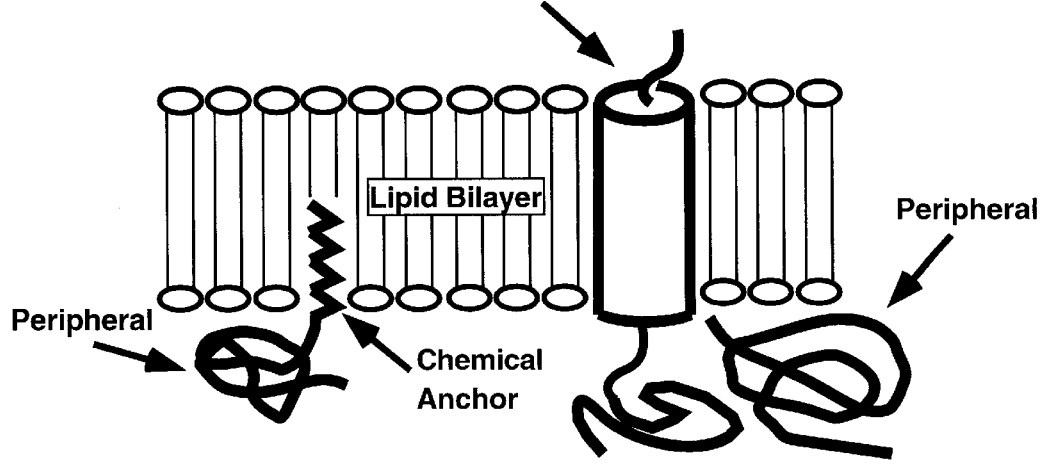
Figure 2:
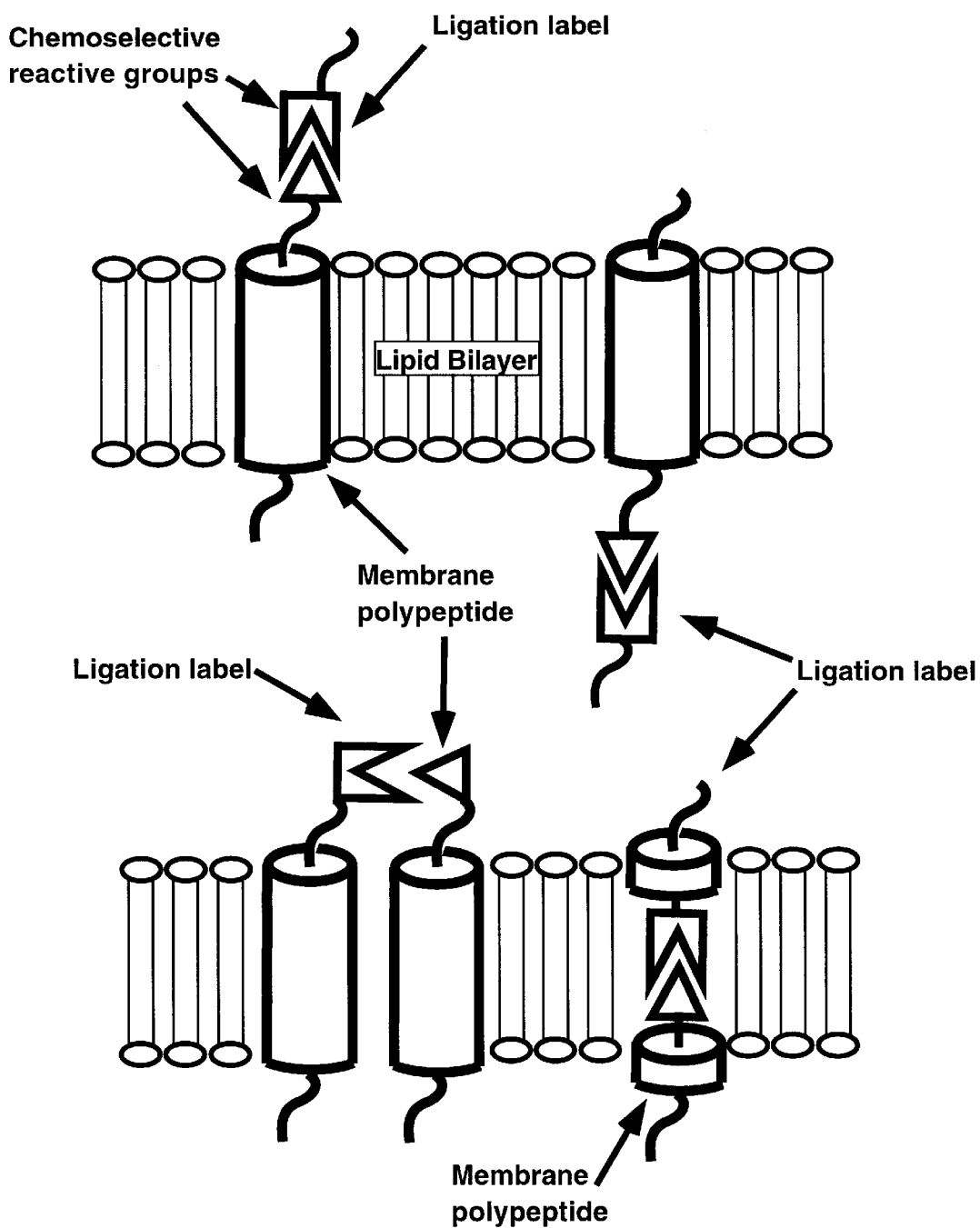
FIG. 2 illustrates various chemical ligation schemes for lipid matrix-embedded membrane polypeptides.

Amino Acids: Include the 20 genetically coded amino acids, rare or unusual amino acids that are found in nature, and any of the non-naturally occurring and modified amino acids. Sometimes referred to as amino acid residues when in the context of a peptide, polypeptide or protein.

Chemoselective chemical ligation: Chemically selective reaction involving covalent ligation of (1) a first unprotected amino acid, peptide or polypeptide with (2) a second amino acid, peptide or polypeptide. Any chemoselective reaction chemistry that can be applied to ligation of unprotected peptide segments.

Chromophore: Chemical moiety that displays light absorption within the ultraviolet (250–400 nm) to visible (400–700 nm) light regions of the spectrum. Includes fluorophores, dyes and donor and acceptor moieties of a resonance energy transfer system. Can occur naturally (intrinsic) or be added (extrinsic) to a biological molecule such as a peptide, polypeptide, carbohydrate or lipid.

Cleavage Site: Amino acid sequence capable of being cleaved by a reagent comprising a chemical or protease that facilitates hydrolysis of a peptide bond between two amino acids of a target polypeptide.

Hydrazone chemical ligation: Chemoselective reaction involving ligation of a first unprotected amino acid, peptide or polypeptide having a hydrazine moiety and a second unprotected amino acid, peptide or polypeptide having an aldehyde or ketone moiety resulting in the formation of a ligation product containing a hydrazone moiety at the ligation site. The backbone structure of a peptide or polypeptide product resulting form hydrazone forming chemical ligation is distinguishable from that of a peptide or polypeptide occurring in nature or via recombinant expression.

Ligation Label: A chemical moiety comprising one or more amino acids. Can be a peptide or polypeptide.

Lipid Matrix: A molecular matrix containing natural, synthetic or combinations thereof of lipid molecules capable of forming a lyotropic phase (i.e., formation of an ordered structure upon interaction with water). Also referred to as a lipid membrane. The lipid molecules have intermediate molecular weight of about 100–5000 and contain a substantial portion of aliphatic or aromatic hydrocarbon. Includes one or more polar lipids such as phospholipids, lysophospholipids, sphingolipids, and glycolipids capable of forming lamellar bilayers and other lipid aggregates having various two-dimensional lamellae and/or hexagonal phase lattice structures and/or three-dimensional cubic phase lattice structures.

Membrane Polypeptide: A polypeptide comprising a hydrophobic moiety that anchors the polypeptide to the lipid membrane. Also referred to as a membrane peptide or membrane protein. Can include one or more lipid membrane anchoring domains, such as a hydrophobic segment of the polypeptide, a covalently attached fatty acid chain or a covalently attached lipid chain. May be a single or multipass transmembrane polypeptide. May include one or more extramembranous amino acid residues that preferentially interact with the aqueous phase, such as residues comprising an extracellular or intracellular loop.

Native chemical ligation: Chemoselective reaction involving ligation of a first unprotected amino acid, peptide or polypeptide and a second unprotected amino acid, peptide or polypeptide resulting in the formation of an amide bond having a backbone structure indistinguishable from that of a peptide or polypeptide occurring in nature or via recombinant expression.

Oxazolidine chemical ligation: Chemoselective reaction involving ligation of a first unprotected amino acid, peptide or polypeptide having an aldehyde or ketone moiety and a second unprotected amino acid, peptide or polypeptide having a 1-amino, 2-ol moiety resulting in the formation of an oxazolidine moiety at the ligation site. The backbone structure of a peptide or polypeptide product resulting from oxazolidine forming chemical ligation is distinguishable from that of a peptide or polypeptide occurring in nature or via recombinant expression.

Oxime chemical ligation: Chemoselective reaction involving ligation of a first unprotected amino acid, peptide or polypeptide having an amino-oxy moiety and a second unprotected amino acid, peptide or polypeptide having an aldehyde or ketone moiety resulting in the formation of an oxime moiety at the ligation site. The backbone structure of a peptide or polypeptide product resulting from oxime chemical ligation is distinguishable from that of a peptide or polypeptide occurring in nature or via recombinant expression.

Peptide: A polymer of at least two monomers, wherein the monomers are amino acids, sometimes referred to as amino acid residues, which are joined together via an amide bond. May have either a completely native amide backbone or an unnatural backbone or a mixture thereof. Can be prepared by known synthetic methods, including solution synthesis, stepwise solid phase synthesis, segment condensation, and convergent condensation. Can be synthesized ribosomally in cell or in a cell free system, or generated by proteolysis of larger polypeptide segments. Can be synthesized by a combination of chemical and ribosomal methods.

Polypeptide: A polymer comprising three or more monomers, wherein the monomers are amino acids, sometimes referred to as amino acid residues, which are joined together via an amide bond. Also referred to as a peptide or protein. Can comprise native amide bonds or any of the known unnatural peptide backbones or a mixture thereof. Range in size from 3 to 1000 amino acid residues, preferably from 3–100 amino acid residues, more preferably from 10–60 amino acid residues, and most preferably from 20–50 amino acid residues. Segments or all of the polypeptide can be prepared by known synthetic methods, including solution synthesis, stepwise solid phase synthesis, segment condensation, and convergent condensation. Segments or all of the polypeptide also can be prepared ribosomally in a cell or in a cell-free translation system, or generated by proteolysis of larger polypeptide segments. Can be synthesized by a combination of chemical and ribosomal methods.

Thiazolidine chemical ligation: Chemoselective reaction involving ligation of a first unprotected amino acid, peptide or polypeptide having an aldehyde or ketone moiety and a second unprotected amino acid, peptide or polypeptide having a 1-amino, 2-thiol moiety resulting in the formation of a thiazolidine moiety at the ligation site. The backbone structure of a peptide or polypeptide product resulting from thiazolidine chemical ligation is distinguishable from that of a peptide or polypeptide occurring in nature or via recombinant expression.

Thioester chemical ligation: Chemoselective reaction involving ligation of a first unprotected amino acid, peptide or polypeptide and a second unprotected amino acid, peptide or polypeptide resulting in the formation of a thioester bond at the ligation site. The backbone structure of a peptide or polypeptide product resulting from thioester chemical ligation is distinguishable from that of a peptide or polypeptide occurring in nature or via recombinant expression.

Thioether chemical ligation: Chemoselective reaction involving ligation of a first unprotected amino acid, peptide or polypeptide and a second unprotected amino acid, peptide or polypeptide resulting in the formation of a thioether bond at the ligation site. The backbone structure of a peptide or polypeptide product resulting from thioether chemical ligation is distinguishable from that of a peptide or polypeptide occurring in nature or via recombinant expression.

DESCRIPTION OF SPECIFIC EMBODIMENTS

The present invention relates to methods and compositions for lipid matrix-assisted chemical ligation and synthesis of membrane polypeptides or membrane polypeptide domains that are incorporated into a lipid matrix. The present invention also relates to compositions produced by the methods of the invention and assays that employ them.

Lipid matrix-assisted chemical ligation and synthesis methods of the invention involve chemoselective ligation of a ligation label to a membrane polypeptide embedded in a lipid matrix. The membrane polypeptide and ligation label components possess unprotected reactive groups that selectively react to yield a covalent bond at the ligation site, also referred to as a chemoselective ligation site. The lipid matrix is exploited to provide (1) environment for maintaining the membrane polypeptide in a prefolded state, and (2) positioning of reactive groups for chemoselective ligation. This aspect of the invention is exemplified in Scheme 1.

   Scheme 1

"$X_n$" represents one or more amino acids. "$R^1$" and "$R^2$" represent unprotected reactive groups capable of chemoselective chemical ligation with respect to each other. "MP" represents a membrane polypeptide comprising at least one hydrophobic (non-polar) region embedded in a lipid matrix. Dashes "—" connecting groups depict covalent bonds. Chemoselective interaction between the unprotected reactive groups of ligation components "$X_n$—$R_2$" and "$R_1$—MP" yields the chemical ligation product "$X_n$—$R_3$—MP," where "$R_3$" represents resultant covalent linkage formed by chemoselective chemical ligation between $X_n$—$R_2$ and $R_1$—MP. Reaction intermediates and side-products are not depicted. A totally synthetic product is produced where all ligation components are man-made by chemical synthesis, i.e., ribosomal-free synthesis. A semi-synthetic product is produced where at least part of a ligation component is made by biological synthesis, i.e., ribosomally in a cell or cell-free translation system, and another part is made by chemical synthesis.

A variety of chemistries can be employed in accordance with the methods of the invention. Any chemoselective reaction chemistry that can be applied to the ligation of unprotected peptide segments is amenable to lipid matrix-assisted chemoselective chemical ligation. These chemistries include, but are not limited to, native chemical ligation (Dawson, et al., Science (1994) 266:776–779; Kent, et al., WO 96/34878), extended general chemical ligation (Kent, et al., WO 98/28434), oxime-forming chemical ligation (Rose, et al., J. Amer. Chem. Soc. (1994) 116:30–33), thioester forming ligation (Schnölzer, et al., Science (1992) 256:221–225), thioether forming ligation (Englebretsen, et al., Tet. Letts. (1995) 36(48):8871–8874), hydrazone forming ligation (Gaertner, et al., Bioconj. Chem. (1994) 5(4):333–338), thiazolidine forming ligation and oxazolidine forming ligation (Zhang, et al., Proc. Natl. Acad Sci. (1998) 95(16):9184–9189; Tam, et al., WO 95/00846).

Reaction conditions for a given ligation chemistry are selected to maintain the desired interaction of the lipid matrix-embedded membrane polypeptide and ligation label components. For example, pH and temperature, water-solubility of the ligation label, ratio of lipid to polypeptide and label, water content and composition of the lipid matrix can be varied to optimize ligation. Addition or exclusion of reagents that solubilize the lipid matrix and/or the membrane polypeptide to different extents may further be used to control the specificity and rate of the desired ligation reaction, i.e., control exposure and presentation of reactive groups by manipulating solubility of the lipid matrix and/or membrane polypeptide. Reaction conditions are readily determined by assaying for the desired chemoselective reaction product compared to one or more internal and/or external controls.

For lipid matrix-assisted native chemical ligation, the membrane polypeptide and ligation label comprise a compatible native chemical ligation component pairing in which one of the components provides a cysteine having an unprotected amino group and the other component provides an amino acid having an unprotected α-thioester group. These groups are capable of chemically reacting to yield a native peptide bond at the ligation site.

The membrane polypeptide and ligation label for lipid matrix-assisted oxime-forming chemical ligation comprise a compatible oxime-forming chemical ligation component pairing in which one of the components provides an unprotected amino acid having an aldehyde or ketone moiety and the other component provides an unprotected amino acid having an amino-oxy moiety. These groups are capable of chemically reacting to yield a ligation product having an oxime moiety at the ligation site.

For lipid matrix-assisted thioester-forming chemical ligation, the membrane polypeptide and ligation label comprise a compatible thioester-forming chemical ligation component pairing in which one of the components provides an unprotected amino acid having a haloacetyl moiety and the other component provides an unprotected amino acid having an α-thiocarboxylate moiety. These groups are capable of chemically reacting to yield a ligation product having an thioester moiety at the ligation site.

The membrane polypeptide and ligation label for lipid matrix-assisted thioether-forming chemical ligation comprise a compatible thioether-forming chemical ligation component pairing in which one of the components provides an unprotected amino acid having a haloacetyl moiety and the other component provides an unprotected amino acid having an alkyl thiol moiety. These groups are capable of chemically reacting to yield a ligation product having a thioether moiety at the ligation site.

The membrane polypeptide and ligation label for lipid matrix-assisted hydrazone-forming chemical ligation comprise a compatible hydrazone-forming chemical ligation component pairing in which one of the components provides an unprotected amino acid having an aldehyde or ketone moiety and the other component provides an unprotected amino acid having an hydrazine moiety. These groups are capable of chemically reacting to yield a ligation product having a hydrazone moiety at the ligation site.

For lipid matrix-assisted thiazolidine-forming chemical ligation, the membrane polypeptide and ligation label comprise a compatible thiazolidine-forming chemical ligation component pairing in which one of the components provides an unprotected amino acid having a 1-amino, 2-thiol moiety and the other component provides an unprotected amino acid having an aldehyde or a ketone moiety. These groups are capable of chemically reacting to yield a ligation product having a thiazolidine moiety at the ligation site.

For lipid matrix-assisted oxazolidine-forming chemical ligation, the membrane polypeptide and ligation label comprise a compatible oxazolidine-forming chemical ligation component pairing in which one of the components provides an unprotected amino acid having a 1-amino, 2-hydroxyl moiety and the other component provides an unprotected amino acid presenting an aldehyde or a ketone moiety. These groups are capable of chemically reacting to yield a ligation product having an oxazolidine moiety at the ligation site.

As is readily apparent, any combination of ligation components that are adapted for chemoselective chemical ligation to yield a lipid matrix-embedded polypeptide product having a covalent bond at the ligation site are considered part of the invention, provided that at least one of the reaction ligation components comprises a membrane polypeptide embedded in a lipid matrix. In particular, the membrane polypeptide ligation component is required to comprise at least one hydrophobic region that anchors the polypeptide to a lipid matrix. An example of an anchoring region is a cell membrane anchor comprising hydrophobic α-helix and/or β-barrel transmembrane components. The membrane polypeptide also may include native amide bonds or any of the known unnatural peptide backbones or a mixture thereof, and other chemical differences from a native amino acid sequence, such as an unnatural amino acid comprising a chromophore or other detectable moiety compatible with maintenance of the membrane polypeptide in the lipid matrix. This includes single-pass and multi-pass transmembrane polypeptides or domains thereof having a native or non-native sequence of amino acids that embed in and interact with a hydrophobic portion of a lipid matrix, and may include one or more extramembranous amino acids that protrude into aqueous phase environment formed by the lipid matrix-water interface. Examples of extramembranous amino acids include those that are part of or form an intracellular or extracellular loop connecting two membrane anchors, an N- or C-terminal sequence, a sequence necessary to facilitate insertion of the polypeptide into a lipid membrane, and/or some other linker or capping sequence of interest.

The membrane polypeptide ligation component preferably comprises an amino acid sequence that permits both insertion and anchoring in a lipid membrane. For example, the membrane polypeptide generally comprises an amino acid sequence capable of forming a transmembrane structure, such as an amphipathic α-helix, organized such that non-polar residues are in contact with the membrane interior and charged or polar residues are in contact with the aqueous phase. Membrane polypeptide ligation components of this type are of sufficient length to span the lipid bilayer, and thus are typically greater than 15–20 amino acids in length. They may range in size up to the full length of a naturally occurring membrane polypeptide, and may include one or more amino acids in addition to such full-length polypeptides, provided the membrane polypeptide is capable of incorporation in the lipid matrix.

The lipid matrix into which the membrane polypeptide component is incorporated includes natural and synthetic lipids capable of forming a lyotropic phase (i.e., formation of an ordered membrane type structure on interaction with water, such as a liquid crystalline phase). These include polar lipids such as phospholipids, lysophospholipids, sphingolipids, and glycolipids capable of forming lamellar bilayers and other lipid aggregates. Preferred lipid matrices form stable membrane monolayers or bilayers and aggregate phases thereof. Of particular interest are lipids that form stable cubic phases (cubic lipidic phase or CLP matrix) (Luzatti, et al., *Nature* (1968) 218:1031–1034; and Lindblom, et al., *Biochimica et Biophysica Acta* (1989)

988:221–256). A cubic phase is one in which the lipid aggregates form a three-dimensional lattice. The lipid aggregate units can have different shapes such as spheres, rods, or lamellae. In contrast, lamellar liquid crystalline phases exhibit a one-dimensional periodicity in which lamellar units of infinite expression are stacked regularly, and hexagonal liquid crystalline phases exhibit a two-dimensional periodicity with rod-like aggregates of infinite length packed into a hexagonal lattice. Thus, cubic phases are optically isotropic whereas lamellar and hexagonal phases are optically anisotropic.

Lipids that form cubic phases consist of a multiple lipid bilayers protruded by multiple aqueous channels formed between certain lipids and polar solvents at specific lipid:solvent ratios (Luzatti, et al., supra; and Lindblom, et al., supra). The lipid diffusion rate inside the CLP is comparable to the rate in lamellar lipid phases and that the diffusion rate in the aqueous compartments is approximately three times slower than in bulk water (Lindblom, et al., supra). Additionally, membrane polypeptides can exhibit full activity when incorporated into cubic phase lipids (Portmann, et al., *J. Phys. Chem.* (1991) 95:8437–8440). Since CLPs are optically isotropic, they can be employed in sensitive spectrophotometric assays. Thus, manipulation of a membrane polypeptide incorporated into a lipid matrix not only provides a prefolded membrane polypeptide serving as a template for chemoselective chemical ligation, the lipid matrix itself can be exploited to facilitate assays that require a lipid-mediated folded membrane polypeptide.

The ligation label component comprises one or more amino acids, and is preferably a peptide or polypeptide. At least one amino acid of the ligation label provides a reactive group that is capable of reacting with and forming a covalent bond with a compatible reactive group provided by the lipid matrix-embedded membrane polypeptide. The ligation label also can comprise a membrane polypeptide component, for example, when modular ligation and synthesis of a multipass transmembrane polypeptide is desired. The ligation label also may comprise native and/or unnatural peptide backbone structure or unnatural amino acid residues or other chemical differences from a native peptide sequence, such as an unnatural amino acid comprising a chromophore or other detectable moiety compatible with chemical ligation of the ligation label and the target lipid matrix-embedded membrane polypeptide.

The lipid matrix, the lipid matrix-embedded membrane polypeptide, and/or ligation label of the invention also may employ one or more chemical tags. The chemical tag may be utilized for multiple purposes such as part of the synthesis process, purification, anchoring to a support matrix, detection and the like. Of particular interest is a chemical tag provided by an unnatural amino acid comprising a chromophore. This includes a chromophore that is an acceptor and/or donor moiety of an acceptor-donor resonance energy transfer pair. Of particular interest are synthesis and purification handles, as well as detectable labels and optionally chemical moieties for attaching the lipid matrix or the lipid matrix embedded membrane polypeptide to a support matrix for screening and diagnostic assays and the like. Various labels described herein are suitable for this purpose. As can be appreciated, in some instances it may be advantageous to utilize a given chemical tag for more than one purpose, e.g., both as a handle for attaching to support matrix and as a detectable label. Examples of chemical tags include metal binding tags (e.g., his-tags), carbohydrate/substrate binding tags (e.g., cellulose and chitin binding domains), antibodies and antibody fragment tags, isotopic labels, haptens such as biotin and various unnatural amino acids comprising a chromophore. A chemical tag also may include a cleavable linker.

Exploiting the lipid matrix to perform chemical ligation of a membrane polypeptide embedded in a lipid matrix provides unprecedented site-specific ligation, detectable labeling and modular synthesis of prefolded membrane polypeptides. Not only does the lipid matrix provide the proper environment for insertion, folding and presentation of a chemical ligation site, embedding the membrane polypeptide component in a lipid matrix exploits the lipid matrix itself as a novel component for controlling specificity of the chemical ligation reaction. For example, a ligation site on the membrane polypeptide can be selected such that it is buried within a lipid membrane bilayer of the matrix. In this situation chemical ligation of a hydrophobic ligation label will be preferred compared to a hydrophilic ligation label. Alternatively, a ligation site can be extra-membranous such that ligation of a hydrophilic ligation label is preferred. Another variation made possible by exploiting the lipid matrix component in combination with the location of the ligation site is construction of a lipid membrane system designed to partition two aqueous phases from each other, such as with closed membrane vesicles (e.g., liposomes), where a ligation site is selected for exposure on one side of the membrane. Exposure of a ligation site can be further adjusted to control the rate and/or extent of the ligation reaction by the addition or exclusion of reagents that solubilize the lipid matrix to different extents. Furthermore, the extent of exposure and reactivity of the ligation site can be controlled by adjusting the reaction conditions such as pH and temperature, as well as the water-solubility of the ligation peptide, water content and composition of the lipid matrix. Thus, depending on the position and orientation of the ligation site with respect to the lipid membrane in which it is embedded, the solubility of the ligation label, and the integrity and composition of the lipid matrix, the specificity and rate of the ligation reaction can be controlled.

The present invention further includes a method of forming a chemoselective ligation site in a lipid matrix-embedded membrane polypeptide when treated with a cleavage reagent that selectively cleaves the polypeptide directly adjacent to an amino acid residue that provides a reactive group for chemical ligation. This aspect of the invention involves contacting a membrane polypeptide that is embedded in a lipid matrix with a reagent that selectively cleaves the polypeptide at a specific site so as to generate a polypeptide comprising an N-terminal residue having an unprotected amino group or a C-terminal residue having an unprotected carboxyl group. This aspect of the invention is exemplified in Scheme 2.

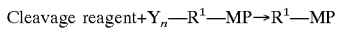

Cleavage reagent+$Y_n$—$R^1$—MP→$R^1$—MP  Scheme 2

"$Y_n$" represents an amino acid sequence comprising a cleavage site, such as a chemical or protease cleavage site, that permits cleavage directly adjacent to the amino acid residue providing the $R_1$ reactive group for subsequent chemoselective chemical ligation.

The cleavage site may occur naturally in the polypeptide or the polypeptide can be engineered to contain one or more such sites. One or more cleavage sites also may be present in the ligation label if desired depending on its intended end use. A naturally occurring or engineered cleavage site therefore allows for the generation of a free and unprotected N-terminal and/or C-terminal residue by site-specific proteolysis. A ligation component generated in this manner therefore contains a residue having an unprotected reactive group amenable to lipid matrix-assisted chemical ligation methods of the invention. It is readily apparent from Scheme 2 that one or more cleavage sites can be incorporated in any combination with a target ligation component of the invention, provided that upon cleavage the cleavage product is adapted for lipid matrix-assisted chemoselective chemical ligation.

The cleavage site can be a protease or a chemical cleavage site. A cleavage site is chosen and/or incorporated into the polypeptide during its synthesis so that upon exposure to the complementary cleavage reagent, the polypeptide is selectively cleaved at the site so as to generate a polypeptide having a free, unprotected amino acid residue having a chemoselective reactive group that is compatible for ligation with a complementary reactive group provided by the ligation label. By way of example, when native chemical ligation chemistry is employed and an endopeptidase cleavage site sequence is incorporated between a linker or capping sequence and a Cys-polypeptide, the cleavage site permits removal of the linker or capping sequence and generation of the desired unprotected Cys-polypeptide. Alternatively, the cleavage site may be positioned adjacent to a residue capable of spontaneous ligation with a complementary reactive group donated by a properly positioned neighboring residue.

Some commonly encountered protease cleavage sites are: Thrombin (KeyValProArg/GlySer); Factor Xa Protease (IleGluGlyArg); Enterokinase (AspAspAspAspLys); rTEV (GluAsnLeuTyrPheGln/Gly), which is a recombinant endopeptidase from the Tobacco Etch Virus; and 3C Human rhino virus Protease (Pharmacia Biotech) (LeuGluValLeuPhe Gln/GlyPro).

Various chemical cleavage sites also are known and include, but are not limited to, the intein protein-splicing elements (Dalgaard, et al., *Nucleic Acids Res.* (1997) 25(6):4626–4638) and cyanogen bromide cleavage sites. Inteins can be constructed which fail to splice, but instead cleave the peptide bond at either splice junction (Xu, et al., *EMBO J* (1996) 15(19):5146–5153; and Chong, et al., *J. Biol. Chem.* (1996) 271:22159–22168). For example, the intein sequence derived from the *Saccharomyces cerevisiae* VMA1 gene can be modified such that it undergoes a self-cleavage reaction at its N-terminus at low temperatures in the presence of thiols such as 1,4-dithiothreitol (DTT), 2-mercaptoethanol or cysteine (Chong, et al., *Gene* (1997) 192:271–281).

Cyanogen bromide (CnBr) cleaves at internal methionine (Met) residues of a polypeptide sequence. Cleavage with CnBr yields two or more fragments, with the fragments containing C-terminal residues internal to the original polypeptide sequence having an activated alpha-carboxyl functionality, e.g. cyanogen bromide cleavage at an internal Met residue to give a fragment with a C-terminal homoserine lactone. For some polypeptide, the fragments will re-associate under folding conditions to yield a folded polypeptide-like structure that promotes reaction between the segments to give a reasonable yield (often 40–60%) of the full-length polypeptide chain (now containing homoserine residues where there were Met residues subjected to cyanogen bromide cleavage)(Woods, et al.,*J. Biol. Chem.* (1996), 271:32008–32015).

In general, a cleavage site for generating a ligation site amenable to a desired chemical ligation chemistry usually is selected to be unique, i.e., it occurs only once in the target polypeptide. However, when more than one cleavage site is present in a target polypeptide that is recognized and cleaved by the same cleavage reagent, if desired one or more of such sites can be permanently or temporarily blocked from access to the cleavage reagent and/or removed during synthesis. In particular, positioning of the cleavage site may be controlled from exposure to the cleavage reagent by exploiting its position in the lipid matrix as described above for the chemoselective ligation site. Cleavage sites can be removed during synthesis of the membrane polypeptide by replacing, inserting or deleting one or more residues of the cleavage reagent recognition sequence, and/or incorporating one or more unnatural amino acids that achieve the same result. A cleavage site also may be blocked by agents that bind to the membrane polypeptide, including ligands that bind the polypeptide and remove accessibility to all or part of the cleavage site. However a cleavage site is blocked or removed, one of ordinary skill in the art will recognize that the method is selected such that upon cleavage the membrane polypeptide is capable of chemoselective chemical ligation to a target ligation component of interest.

Inclusion of a cleavage site for generating a chemoselective ligation site is particularly advantageous when the membrane polypeptide is adapted with a capping, signal or other type of leader sequence containing information necessary to facilitate or improve efficacy of insertion into a lipid membrane, insertion into particular membranes of choice, detection, and/or purification. For example, cleaving a membrane polypeptide after it is embedded within a lipid membrane matrix permits selection of properly folded polypeptides, as well as removal of sequences that may be needed to initiate proper insertion and folding, but are no longer needed once a hydrophobic anchoring sequence is embedded in the lipid matrix. The cleavage site also can be used for detection and/or purification of properly incorporated and folded polypeptides. For example, when a membrane polypeptide is selected to comprise a cleavage site designed for extramembranous exposure, then polypeptides having the appropriate configuration in a lipid membrane, and thus extramembranous exposure of the cleavage site, are likely to exhibit maximum sensitivity to cleavage when a water-soluble cleavage reagent is employed under aqueous conditions, such as a water-soluble endoprotease. A cleavage site for generating a chemoselective ligation site may also be included when a purification handle or tag is included as part of a fusion polypeptide to ease its purification following synthesis. Thus, inclusion of a cleavage site designed to generate a chemoselective ligation site can be exploited for multiple purposes.

The membrane polypeptide and ligation label component pairings suitable for the chemical ligation approaches exemplified by Schemes 1–2 can be designed de novo or derived from virtually any known membrane protein system, including those derived from viral, eukaryotic, prokaryotic, and archaebacterial systems, including psychrophilic, mesophilic and thermophilic organisms, and particularly the two major classes of membrane proteins, i.e., those that insert α-helices into the lipid bilayer, and those that form pores by a β-barrel strands. Examples include membrane associated receptors, transporter proteins (e.g., ion and other channels such as potassium, sodium, proton, chloride channels, pores; active transporters such as TEXAN drug transporters, mini-TEXANS and ABC drug transporters and antiporters such as the H+/glucose antiporter); enzymes (e.g. leucotriene C4 synthase); and immunogens (e.g. tumor metastasis-associated antigen). Of particular interest are enzyme-linked receptors, fibronectin-like receptors, the seven transmembrane receptors, and the ion channel receptors, including the tyrosine and serine-threonine kinases, and guanylate cyclase families of enzyme-linked receptors. Examples of the tyrosine kinase family of receptors include epidermal growth factor, insulin, platelet-derived growth factor, and nerve growth factor. Examples of the serine kinase family of receptors include growth factor β-family. Examples of the guanylate cyclase family includes those receptors that generate cyclic GMP (cGMP) in response to atrial natriuretic factors. Examples of the seven-transmembrane receptors include those membrane proteins that bind catecholamines, histamines, prostaglandins, etc., and the opsins, vasopressin, chemokine and melanocortin receptors. Examples of the ion channel receptors are represented by the ligand- and voltage-gated channel membrane protein receptors, and include the acetylcholine activated sodium channels, glycine and gamma-aminoisobutyric acid activated chloride channels, and serotonin and glutamate activated calcium channels, and the family of cyclic nucleotide-gated channels (cAMP and cGMP), and the family of inositol 1,4,5-triphosphate (IP3) and the cyclic ADP-ribose receptors that modulate calcium storage. One of ordinary skill in the art will recognize that nucleic acid and/or amino acid sequences for the above and additional membrane polypeptides can be identified in various genomic and protein related databases. Examples of publicly accessible databases include as GenBank (Benson, et al., *Nucleic Acids Res* (1998)26(1):1–7; USA National Center for Biotechnology Information, National Library of Medicine, National Institutes of Health, Bethesda, Md., USA), TIGR Database (The Institute for Genomic Research, Rockville, Md., USA), Protein Data Bank (Brookhaven National Laboratory, USA), and the ExPASy and Swiss-Protein database (Swiss Institute of Bioinformatics, Genève, Switzerland).

In selecting the membrane polypeptide and ligation label component pairings and their respective ligation sites, complementary chemoselective pairings can be identified by analysis of a target polypeptide's structure in the context of its function using one or more routine procedures such as biological, thermodynamic, computational and structural techniques known in the art and as described herein. The information is used to select one or more chemoselective ligation sites present in the native structure and/or engineered into a synthetic form of the molecule. In particular, structural and functional information can be obtained using standard techniques including homology comparisons to other polypeptides having similar amino acid sequences and domains, preferably other polypeptides for which at least some structural and functional information is known. For an exemplary list of membrane polypeptides of known three-dimensional structure, see Preusch, et al., *Nature Struct. Biol.* (1998) 5:12–14.

Uniqueness of the ligation site, stability of the ligation components, specificity and completeness of the ligation reaction, and stability and function of the lipid matrix-embedded membrane polypeptide ligation product are considerations of the selection process. In particular, ligation component pairings are preferably designed to maximize selectivity of the ligation reaction and stability of the ligation product within the lipid matrix. This includes design of linker or capping sequences comprising one or more cleavage sites employed for incorporation and generation of a chemoselective ligation site of a ligation component in the lipid matrix. For example, mutagenesis, thermodynamic, computational, modeling and/or any technique that reveals functional and/or structural information regarding a target polypeptide of interest can be used for this process. These techniques include immunological and chromatographic analyses, fluorescence resonance energy transfer (FRET), circular dichroism (CD), nuclear magnetic resonance (NRM), electron and x-ray crystallography, electron microscopy, Raman laser spectroscopy and the like, which are commonly exploited for designing and characterizing membrane polypeptide systems. (See, e.g., Newman, R., *Methods Mol. Biol.* (1996) 56:365–387; Muller, et al., *J. Struct. Biol.* (1997) 119(2):149–157; Fleming, et al., *J. Mol. Biol.* (1997) 272: 266–27; Haltia, et al., *Biochemistry* (1994) 33(32): 9731–9740.5; Swords, et al., *Biochem J.* (1993) 289(1): 215–219; Wallin, et al., *Protein Sci.* (1997) 6(4):808–815; Goormaghtigh et al., *Subcell Biochem.* (1994) 23:405–450). Muller, et al., *Biophys J.* (1996) 70(4):1796–1802; Sami, et al., *Biochimica et Biophysica Acta* (1992) 1105(1):148–154. Wang, et al., *J. Mol. Biol.* (1994) 237(1):1–4; Watts, et al., *Mol. Memb. Biol.* (1995) 12(3):233–246; Bloom, M., *Biophys J.* (1995) 69(5):1631–1632; and Gutierrez-Merino, et al., *Biochem Soc. Trans.* (1994) 22(3):784–788).

When structural information is not immediately available, the chemoselective chemical ligation components can be identified and modeled in two-dimensions by various techniques known in the art. For example, amphipathic α-helix segments that span a lipid membrane bilayer, and thus greater than about 15–20 residues, can be identified in the primary structure using secondary structure prediction algorithms. Segments greater than 15–20 residues are selected based on sequence similarity between members of a superfamily, and then one or more ligation sites are identified for compatibility with a ligation label that may or may not be part of the original two-dimensional model. (See, e.g., Reithmeier, R. A., *Curr. Opin. Struct. Biol.* (1995) 5(4):491–500; Du, et al., *Protein Eng.* (1994) 7(10):1221–1229). A preferred homology modeling and database alignments with the aid of one or more computer programs suited for membrane polypeptide modeling and/or prediction. For example, the program "TmPred" and "Top-PredII" can be used to make predictions of membrane-spanning regions and their orientation, which is based on the statistical analysis of a database of transmembrane proteins present in the SwissProt database. (Gunnar von Heijne, *J. Mol. Biol.* (1992) 225:487–494; Hoppe-Seyler, *Biol. Chem.* (1993) 347:166; and Claros, et al., *Comput Appl Biosci.* (1994) 10(6):685–686). Other programs can be used and include: "DAS" (Cserzo, et al., *Prot. Eng.* (1997) 10(6):673–676); "PHDhtm" (Rost, et al., *Protein Science* (1995) 4:521–533); and "SOSUI" (Mitaku Laboratory, Department of Biotechnology, Tokyo University of Agriculture and Technology).

The ligation components and complementary pairings thereof also can be selected by modeling them in three-dimensions at the atomic level to simulate the ligated product and/or the pre-ligation reaction components. First, a sequence alignment between the polypeptide to be modeled and a polypeptide of known structure is established. Second, a backbone structure is generated based on this alignment. This is normally the backbone of the most homologous structure, but a hybrid backbone also may be used. Third, side chains are then placed in the model. Various techniques like Monte Carlo procedures, tree searching algorithms etc., can be used to model rotomer side chains having multiple possible conformations. If the polypeptide to be modeled has insertions or deletions with respect to the known structure, loops are re-modeled, or modeled ab initio. Database searches for loops with similar anchoring points in the structure are often used to build these loops, but energy based ab initio modeling techniques also can be employed. Energy minimizations, sometimes combined with molecular dynamics, are then normally used for optimization of the final structure. The quality of the model is then assessed, including visual inspection, to verify that the structural aspects of the model are not contradicting what is known about the functional aspects of the molecule.

The three-dimensional models are preferably generated using a computer program that is suitable for modeling membrane polypeptides. (Vriend, G., "Molecular Modeling of GPCRs," In: 7TM (1995) vol. 5). Examples of computer programs suitable for this purpose include: "What If" (Vriend, G., J. Mol. Graph. (1990) 8:52–56; available from EMBL, Meyerhofstrasse 1, 69117 Heidelberg, Germany) and "Swiss-Model" (Peitsch MC and Herzyk P (1996) "Molecular modeling of G-protein coupled receptors." In: G Protein-coupled Receptors. New opportunities for commercial development, 6:6.29–6.37, N Mulford and L M Savage Eds., IBC Biomedical Library Series; Peitsch, et al., *Receptors and Channels* (1996) 4:161–164; Peitsch, et al., "Large-scale comparative protein modeling," In: Proteome research: new frontiers in functional genomics," pp. 177–186, Wilkins M R, Williams K L, Appel R O, Hochstrasser D F, Eds., Springer, 1997).

Factors that influence lipid matrix-assisted chemoselective ligation, and thus selection of a compatible ligation site, generally parallel those known for soluble proteins (Woods, et al., *J. Biol. Chem.* (1996) 271:32008–32015). First, secondary structure is not critically important in that ligation sites within most α-helix and β-sheet are amenable to ligation. Ligation sites at most turns also are okay, although ligation sites corresponding to the extremity of a β-turn are less preferred. Second, a ligation site is preferably positioned on the surface of the folded polypeptide, as opposed to being buried or internal to the folded polypeptide at positions required to stabilize the folded form of the polypeptide in the lipid environment.

Accordingly, selection of chemoselective ligation components and complementary pairings thereof also considers the thermodynamic cost of exposing and/or transferring charged or highly polar uncharged compounds into the oil-like hydrocarbon interior of membranes. For instance, positioning of a ligation site, such as one designed for generation by site-specific cleavage of a lipid matrix-embedded membrane polypeptide, is not only designed for ligation selectivity, but it also is designed so that the precursor and final ligation products are sufficiently stable in the lipid matrix. In this aspect of the invention, most amino acid side chains of transmembrane segments must be non-polar (e.g. Ala, Val, Leu, Ile, Phe). Thus residue positions having a naturally occurring ligation site residue or that are targeted for substitution or insertion of a ligation site residue by engineering are selected to maintain the favorable hydrophobic interactions, such as hydrophobic packing interactions found between the α-helix membrane anchors. Additionally, the very polar CONH groups (peptide bonds) of the polypeptide backbone of transmembrane segments are selected to participate in hydrogen bonds (H-bonds) in order to lower the cost of transferring them into the hydrocarbon interior (See, e.g., Roseman, A., *J. Mol. Biol.* (1988) 201:621–625). Thus in selecting a compatible ligation site, this H-bonding is most easily accomplished by maintaining the α-helices for which all peptide bonds are H-bonded internally. It also can be accomplished by maintaining β-sheets for porin-type transmembrane proteins, provided that the β-strands form closed structures such as the β-barrel. Since all membrane polypeptides of known three-dimensional structure adhere to these principles, the chemoselective chemical ligation sites can be selected and/or designed to adhere to these principles when a folded transmembrane polypeptide is desired. In some cases appropriately placed positively charged lysine residues can be used to control the overall membrane orientation (Whitley, et al., *Nat. Struct Biol.* (1994) 1(12):858–862).

Compatible ligation component pairings and their chemoselective chemical ligation sites also can be identified by ligation site scanning. This involves a genetic approach to introduce amino acid residues amenable to a particular ligation chemistry by site-specific, nested and/or random mutagenesis into DNA in a cell or a cell free system, encoding a target membrane polypeptide or domain thereof of interest, followed by expression of the mutated DNA and screening for membrane polypeptides containing functional, ligation compatible substitutions or insertions. Alternatively, mutated membrane polypeptides can be chemically synthesized, or a combination of genetic and chemical synthesis can be used. Whether recombinant DNA and/or chemical synthesis is employed, the polypeptides subjected to ligation site scanning will preferably comprise at least one membrane-anchoring segment capable of insertion into a lipid membrane, such as a transmembrane spanning segment or transmembrane polypeptide domain. Membrane polypeptides and ligation labels comprising one or more of the functional mutations are then synthesized to generate one or more of the chemoselective ligation compatible pairings exemplified in Schemes 1–2. The ligation components are then subjected to the appropriate ligation chemistry of interest and screened for ligated membrane polypeptides that properly insert and fold in the lipid matrix.

The ligation site scanning approach not only permits rapid and high throughput screening of large numbers of compatible ligation components, it also permits rapid screening for novel and diverse recombinant, synthetic and semi-synthetic molecules formed by new combinations of membrane polypeptide and ligation label components pairings. As an example, the membrane polypeptide and ligation label components can be obtained from mixtures or libraries representing a diversity of chemical structures, such as different amino acid sequences as well as different unnatural side-chain substituents. A library may contain certain sets of peptide or polypeptides containing a different chemical entity at a particular position, and/or others that are randomly different. Such components can be recombinantly expressed, derived from phage display libraries, derived from chemical synthesis, or fragments and combinations thereof. Libraries of modular cross-over membrane polypeptides and ligation components also may be constructed utilizing the modular approach described in Kent, at al., WO 99/11655. In this embodiment of the invention, lipid matrix-embedded membrane polypeptides are generated by cross-over chemoselective chemical ligation of two or more peptide segments comprising one or more functional protein modules derived from different parent membrane polypeptides of the same class or family so as to generate one or more lipid matrix-embedded hybrid membrane polypeptides. This permits introduction of functional domains and the like from different members of the same class or family of membrane polypeptides so as to generate libraries of great diversity, including ligation site information as well as structure-function information. As can be appreciated, rapid screening and selection of one or more ligation component pairings by ligation site scanning is therefore particularly suited for identifying compatible and diverse combinations of reaction components illustrated in Schemes 1–2 above.

For synthesis of the ligation components, any number of methods known in the art can be employed. These include chemical and biological methods or combinations thereof. For example, a nucleic acid sequence coding for part or all of a ligation component can be expressed in a host cell, and recovered using standard techniques and/or those described herein. This approach is particularly useful when a membrane polypeptide is recalcitrant to chemical synthesis alone. Peptide or polypeptides also can be produced using chemical methods to synthesize the desired ligation component in whole or in part.

For synthesis in a cell, polypeptides can be generated by standard techniques. Cells that naturally express a target polypeptide can be employed. Transfection and transformation of a host cell with DNA encoding a polypeptide of interest also can be used. For example, a polymerase chain reaction (PCR) based strategy may be used to clone a target DNA sequence encoding all or part of a target membrane polypeptide of interest. (See, e.g., "PCR Cloning Protocols: From Molecular Cloning to Genetic Engineering," B. A. White, ed., Humana Press, Methods in Molecular Biology, Vol. 67, 1997). For example, PCR can be used for cloning through differential and subtractive approaches to cDNA analysis, performing and optimizing long-distance PCR, cloning unknown neighboring DNA, and using PCR to create and screen libraries. PCR also can be used to introduce site-specific and random mutations into DNA encoding a target membrane polypeptide and/or ligation label of interest. This approach is particularly suited for engineering cysteine ligation sites.

For general cloning purposes, complementary and/or degenerate oligonucleotides corresponding to conserved motifs of the target membrane polypeptide may be designed to serve as primers in a cDNA and/or PCR reaction. Templates for primer design can be obtained from any number of sources. For example, sequences, including expressed sequence tags (ESTs) can be obtained from various databases, such as GenBank, TIGR, ExPASy and Swiss-Protein databanks. Homology comparisons performed using any one of a number of alignment readily available programs that employ search engines to find the best primers in a sequence based on various algorithms. Any number of commercially available sequence analysis packages, such as Lasergene, GeneWorks, DNASIS, Gene Jockey II, Gene Construction Kit, MacPlasmap, Plasmid ARTIST, Protein Predictor, DNA/RNA Builder, and Quanta. (See, e.g., "Sequence Data Analysis Guidebook," Simon R. Swindell, ed., Humana Press, 1996). The information can be used to design degenerate primers, nested/multiplex primers, site-directed mutagenesis, restriction enzyme sites etc. Primers can be designed from homology information, and computer programs can be used for primer design as well. Examples include "Primer Premier 4.0" for automatic primer selection (Clone Tech, Inc.). The amplified cDNA and/or PCR fragment may be used to isolate full-length clones by radioactive or non-radioactive labeling of the amplified fragment and screening a library.

Alternatively, membrane polypeptide DNA cloned from one source may be utilized to obtain the corresponding target membrane polypeptide DNA sequence from other sources. Specifically, a genomic and/or cDNA library constructed from DNA and/or RNA prepared from a cell known or expected to express the target membrane polypeptide may be used to transform a eukaryotic or prokaryotic host cell that is deficient in the putative gene. Transformation of a recombinant plasmid coding for the polypeptide into a deficient host cell would be expected to provide the cell with a complement product corresponding to the polypeptide of interest. In some cases, a host cell can be selected to express a particular phenotype associated with the target polypeptide and thus may be selected by this property. For a review of cloning strategies which may be used, see e.g., Sambrook, et al., 1989, Molecular Cloning, A Laboratory Manual, Cold Springs Harbor Press, New York; and Ausubel, et al., 1989, Current Protocols in Molecular Biology, Green Publishing Associates and Wiley Interscience, New York.

To express a target membrane polypeptide in a host cell the nucleotide sequence coding for the polypeptide, or a functional equivalent for modular assembly as described above, is inserted into an appropriate expression vector, i.e., a vector which contains the necessary elements for the transcription and translation of the inserted coding sequence. Host cells containing the coding sequence and that express the target gene product may be identified by standard techniques. For example, these include but are not limited to DNA-DNA or DNA-RNA hybridization; the presence or absence of "marker" gene functions; assessing the level of transcription as measured by the expression of mRNA transcripts in the host cell; and detection of the gene product as measured by immunoassay or by its biological activity.

Once a clone producing the target polypeptide is identified, the clone may be expanded and used to produce large amounts of the polypeptide, which may be purified using techniques well-known in the art including, but not limited to immunoaffinity purification, chromatographic methods including high performance liquid chromatography or cation exchange chromatography, affinity chromatography based on affinity of the polypeptide for a particular ligand, immunoaffinity purification using antibodies and the like. For example, when expressed in a host cell, extraction and purification of membrane polypeptides can be performed following standard techniques. (Ohlendieck, K., *Methods Mol Biol.* (1996) 59:313–322). Ohlendieck, K., *Methods Mol Biol.* (1996) 59:293–304; Josic D, et al., *Methods Enzymol.* (1996), 271:113–134). Thus in another embodiment of the invention, nucleic acid encoding recombinant membrane polypeptides modified to contain one or more engineered ligation site residues designed to be accessible to chemical ligation are provided.

Some commonly used host cell systems for expression and recovery of membrane polypeptides include *E. coli*, *Xenopus oocytes*, baculovirus, vaccinia, and yeast, as well as many higher eukaryotes including transgenic cells in culture and in whole animals and plants. (See, e.g., G. W. Gould, "Membrane Protein Expression Systems: A User's Guide," Portland Press, 1994, Rocky S. Tuan, ed.; and "Recombinant Gene Expression Protocols," Humana Press, 1996). For example, yeast expression systems are well known and can be used to express and recover target membrane polypeptide of interest following standard protocols. (See, e.g., Nekrasova et al, *Eur. J. Biochem.* (1996) 238:28–37; Gene Expression Technology Methods in Enzymology 185: (1990); Molecular Biology and Genetic Engineering of Yeasts, CRC Press, Inc. (1992); Herescovics, et al., *FASEB* (1993) 7:540–550; Larriba, G., *Yeast* (1993) 9:441–463; Buckholz, R. G., *Curr Opinion Biotech* (1993) 4:538–542; Asenjo, et al., "An Expert System for Selection and Synthesis of Protein Purification Processes Frontiers in Bioprocessing II," pp. 358–379, American Chemical Society, (1992); Mackett, M, "Expression of Membrane Proteins in Yeast Membrane Protein Expression Systems: A Users Guide," pp. 177–218, Portland Press, (1995).

When chemical synthesis is employed, the peptide or polypeptides can be linear, cyclic or branched, and often composed of, but not limited to, the 20 genetically encoded L-amino acids. In vitro suppression mutagenesis in a cell free system also can be used to introduce unnatural amino acids into the polypeptides (See, e.g., Cload, et al., *Chem*- istry and Biology (1996) 3:1033–1038) and Turcatti, et al., J. Bio. Chem. (1996) 271:19991–19998). Such chemical synthetic approaches also permit incorporation of novel or unusual chemical moieties including D-amino acids, other unnatural amino acids, oxime, hydrazone, ether, thiazolidine, oxazolidine, ester or alkyl backbone bonds in place of the normal amide bond, N- or C-alkyl substituents, side chain modifications, and constraints such as disulfide bridges and side chain amide or ester linkages. See, for example, Wilkins, et al., Curr. Opin. Biotech. (1998) 9(4):412–426, which reviews various chemistries for chemical synthesis of peptides and polypeptides.

For example, native chemical ligation and synthesis of polypeptides having a native peptide backbone structure is disclosed in Kent, et al., WO 96/34878. See also Dawson, et al. (Science (1994) 266:77–779) and Tam, et al. (Proc. Natl. Acad. Sci. USA (1995) 92:12485–12489). Unnatural peptide backbones also can be made by known methods (See, e.g., Schnolzer, et al., Science (1992) 256:221–225; Rose, et al., J. Am. Chem. Soc. (1994) 116:30–34; and Liu, et al., Proc. Natl. Acad. Sci. USA (1994) 91:6584–6588; Englebretsen, et al., Tet. Letts. (1995) 36(48):8871–8874; Gaertner, et al., Bioconj. Chem. (1994) 5(4):333–338; Zhang, et al., Pro. Natl. Acad. Sci. USA (1998) 95(16):9184–9189; and Tam, et al., WO 95/00846). Extended general chemical ligation and synthesis also may be employed as disclosed in Kent, et al., WO 98/28434.

Additionally, rapid methods of synthesizing assembled polypeptides via chemical ligation of three or more unprotected peptide segments using a solid support, where none of the reactive functionalities on the peptide segments need to be temporarily masked by a protecting group, and with improved yields and facilitated handling of intermediate products is described in Canne, et al., WO/98/56807. Briefly, this method involves solid phase sequential chemical ligation of peptide segments in an N-terminus to C-terminus direction, with the first solid phase-bound unprotected peptide segment bearing a C-terminal α-thioester that reacts with another unprotected peptide segment containing an N-terminal cysteine and a C-terminal thioacid. The techniques also permits solid-phase native chemical ligation in the C- to N-terminus direction. Large polypeptides can also be synthesized by chemical ligation of peptide segments in aqueous solution on a solid support without need for protecting groups on the peptide segments. A variety of peptide synthesizers are commercially available for batchwise and continuous flow operations as well as for the synthesis of multiple peptides within the same run and are readily automated.

A ligation component also can be selected to contain moieties that facilitate and/or ease purification and/or detection. For example, purification handles or tags that bind to an affinity matrix can be used for this purpose. Many such moieties are known and can be introduced via post-synthesis chemical modification and/or during synthesis. (See, e.g., Protein Purification Protocols, (1 996), Doonan, S., ed., Humana Press Inc.; Schriemer, et al., Anal. Chem. (1998) 70(8):1569–1575; Evangelista, et al., J. Chromatogr. B. Biomed. Sci. Appl. (1997) 699(1–2):383–401; Kaufmann, M., J. Chromatogr. B. Biomed. Sci. Appl. (1997) 699(1–2):347–369; Nilsson, et al, Protein Expr. Purif. (1997)11(1):1–16; Lanfermeijer, et al., Protein Expr. Purif. (1998) 12(1): 29–37). For example, one or more unnatural amino acids having a chemical moiety that imparts a particular property that can be exploited for purification can be incorporated during synthesis. Purification sequences also can be incorporated by recombinant DNA techniques. In some instances, it may be desirable to include a chemical or protease cleavage site to remove the tag, depending on the tag and the intended end use. An unnatural amino acid or chemically modified amino acid also may be employed to ease detection, such as incorporation of a chromophore, hapten or biotinylated moiety detectable by fluorescence spectroscopy, immunoassays, and/or MALDI mass spectrometry.

Homogeneity and the structural identity of the desired membrane polypeptide and ligation label component synthesis products can be confirmed by any number of means including immunoassays, fluorescence spectroscopy, gel electrophoresis, HPLC using either reverse phase or ion exchange columns, amino acid analysis, mass spectrometry, crystallography, NMR and the like. Positions of amino acid modifications, insertions and/or deletions, if present, can be identified by sequencing with either chemical methods (Edman chemistry) or tandem mass spectrometry.

The lipid matrix component may include natural and/or synthetic lipids capable of forming a lyotropic phase (e.g., liquid crystalline phase upon interaction with water). Of particular interest are polar lipids such as phospholipids, lysophospholipids, sphingolipids, and glycolipids capable of forming lamellar bilayers and other lipid aggregates, which includes mixtures of lipids capable of forming a lyotropic crystalline phase. Examples of such lipids include, but are not limited to, insoluble non-swelling amphiphiles, insoluble swelling amphiphiles, and various soluble amphiphiles capable of forming lyotropic liquid crystalline phases. Examples of insoluble non-swelling amphiphiles include triglycerides, diglycerides, long chain protonated fatty acids, long chain normal alcohols, long chain normal amines, long chain aldehydes, phytols, retinols, vitamin A, vitamin K, vitamin E, cholesterol, desmosterol, sitosterol, vitamin D, unionized phosphatidic acid, sterol esters of very short chain acids, waxes in which either acid or alcohol moiety is less than 4 carbon atoms long (e.g., methyl oleate), and ceremides. Examples of insoluble swelling amphiphiles include phosphatidylcholine, phosphatidylethanolamine, phosphatidylinositol, sphingomyelin, cardiolipid, plasmalogens, ionized phosphatidic acid, cerebrosides, phosphatidylserine, monoglycerides, acid-soaps, α-hydroxy fatty acids, monoethers of glycerol, mixtures of phospholipids and glycolipids extracted from cell membranes or cellular organelles (plant glycolipids and sulfolipids), sulfocerebrosides, sphingosine (basic form). Examples of soluble amphiphiles capable of forming lyotropic liquid crystalline phases include sodium and potassium salts of long chain fatty acids, many of the ordinary anionic, cationic, and nonionic detergents, lysolecithin, palmitoyl and oleyl coenzyme A, and other long chain thioesters of coenzyme A, gangliosides, and sphingosine (acid form).

Preferred lipid matrices form stable membrane monolayers or bilayers and aggregate phases thereof. Of particular interest are lipids that form stable cubic phases, also referred to as a cubic lipidic phase or CLP matrix (Lindblom, et al., supra). Examples of lipids capable of forming cubic phases include, but are not limited to, the following lipids: phosphatidylcholine (PC); dipalmitoylphosphatidylcholine (DPPC); 1-palmitoyl-2-oleoylphosphatidylcholine (POPC); dioleoylphosphatidylcholine (DOPC); dilinoleoylphosphatidylcholine (DliPC); lysophosphatidylcholine (LPC); 1, palmityol-LPC (PaLPC); 1-oleoyl-LPC (OILPC); 1, monoolein (MO); phosphatidylethanolamine (PE); plasmaenylethanolamine (PalE); glycerol acetal of plasmaenylethanolamine (GAPlaE); didodecylphosphatidylethanolamine (DDPE); dielaidoylphosphatidylethanolamine (DEPE); dioleoylphosphatidylethanolamine (DOPE); dilineoleoylphosphatidylethanolamine (DliPE); dioleoylphosphatidyl-N-monomethyl-ethylethanolamine (DOPE-Me); diphosphatidylglycerol (DPG); phosphatidylglycerol (PG); phosphatidylserine (PS); phosphatidylinositol (PI); monoglucolsyldiacylglycerol (MgluDG); monogalactosyldiacylglycerol (MgalDG); diglucosyldiacylglycerol (DgluDG); digalactosyl-diactylglycerol (DgalDG); dioleoylmonoglucosyldiacylglycerol (DOMGluDG); dioleoyldiglucosyldiacylglycerol (DODGluDG); glyceroldialkylnonitol tetraether (GDNT); and a glycerol-lipid mixture of 70% of GDNT with β-D-glycopyranose linked to the nonitol group; 30% of glycerol dialkyl glycerol tetraether with β-D-galactopyranosyl-β-D-galactopyranose linked to one of the glycerol groups (GL).

Hydration, temperature and lipid composition can be varied to modulate the liquid crystal structure of a lipid matrix. For example, cubic phase lipid systems that include mixtures of MO with 1-palmitoyl-2-oleoyl-3-phosphatidylserine (PaOlPS) and DEPE/alamethicin form bicontinuous cubic phases under fully hydrated conditions within certain concentration ratios and temperature ranges. In contrast, DOPE with up to 10 mol % PaOlPS exists in the hexagonal phase at room temperature. Thus temperature and composition of the lipid membrane can be used to control the crystalline phase. Such parameters are known for many lipid systems, or can be determined by various methods known in the art, including testing a serial array of mixtures with various concentrations of particular lipid components and water, and comparing them over a range of temperatures. More specialized techniques also can be employed to fine tune the cubic phases of a particular lipid/water system, such as determination of phase diagrams, X-ray diffraction, NMR, and polarized light microscopy and the like (Lindblom, et al., supra).

Lipids capable of forming cubic phases that have a certain water content by weight percent (wt %) and minimum temperature (° C.) for formation of the cubic phase include, but are not limited to, the following lipid/water systems: MO with 12–40 wt % water content and temperature minimum of 20° C.; PaLPC with 40–46 wt % water content and temperature minimum of 25° C.; OlLPC with 20–25 wt % water content and temperature minimum of 25° C.; Egg PC with 0–4 wt % water content and temperature minimum of 75° C.; DOPC with 2–11 wt % water content and temperature minimum of 60° C.; DliPC with 4 wt % water content and temperature minimum of 55° C.; Egg PC+22–35 wt % sodium cholate with 22–26 wt % water content and temperature minimum of 22° C.; Egg PC+75–80 wt % diacylglycerol with excess water content and temperature minimum of 10° C.; Egg PC+85 wt % DliPE with excess water content and temperature minimum of 40° C.; DOPE with 67 wt % water content and temperature minimum of 25° C.; DOPE-Me with 67 wt % water content and temperature minimum of 25° C.; DOPC+0–50 wt % DOPE with water content of 10 wt % and temperature minimum of 70° C.; POPC+85–90 wt % DliPE with 29–41 wt % water content and temperature minimum of 7° C.; PE from P. regina with water content of 35–50 wt % and temperature minimum of 40° C.; PE from B. megaterium with 8–26 wt % water content and temperature minimum of 58° C.; DDPE with water content of 10–16 wt % or greater than 33 wt % and temperature minimum of 75° C. or 115° C., respectively; DPG from bovine heart+29 wt % dibucane with 41 wt % water content and temperature minimum of 7° C.; sodium sulfatide from human brain with 40–70% water content and temperature minimum of 20° C.; DOMGluDG from A. laidlawii with 7–15 wt % water content and temperature minimum of 0° C.; DOMGluDG+51 wt % DODGluDG from A. laidlawii with 10 wt % water content and temperature minimum of 25° C.; MgalDG+31 wt % DgalDG from maize chloroplasts with 10–20 wt % water content and temperature minimum of 60° C.; MgalDG 34–50 wt %+DgalDG from wheat chloroplasts with water content of 3–15 wt % and temperature minimum of 10° C.; GDNT with 7–13 wt % water content and temperature minimum of 15° C.; GL with 0–11 wt % water content and temperature minimum of 60° C.; polar lipids from A. laidlawii with 18 wt % water content and temperature minimum of 65° C.; and polar lipids from S. solfactaricus with water content of 20 or 40 wt % and temperature minimum of 85° C. (Lindblom, et al., supra).

The lipids may be obtained from various sources including commercial sources or produced and prepared as micelles, liposome vesicles, CLP matrices, or continuous lamellar membranes purified from cells following standard techniques known in the art. (See, e.g., Small, D. M., (1986) "The physical chemistry of lipids from alkenes to phospholipids," In: Handbook of Lipid Research, vol. 4, pp. 1–672, D. Haccham, ed, Plenum Press New York; Winterhalter, et al., Chem. Phys. Lipids (1993) bx;164(1–3):35–43; McNamee, M G., Biotechniques (1989) 7(5): 466–475; Albertsson et al., Methods Biochem Anal. (1982) 28: 115–150; Graham, J M., Methods Mol Biol. (1993) 19: 97–108; and Kinne-Saffran, et al., Methods Enzymol. (1989) 172: 3–17; Larsson, K., J. Phys. Chem. (1989) 93:7304–7314; Zumbuchl, et al., Biochimica et Biophysica Acta (198X) 640:252–262; Erikson, et al., J. Phys. Chem. (1985) 91:846; Seddon, et al., Prog. Colloid Polym. Sci. (1990) 81:189; and U.S. Pat. No. 5,554,650).

A lipid matrix for incorporation of a membrane polypeptide is selected for compatibility with the polypeptide. In particular, a membrane polypeptide known to be stable over a particular temperature range is selected for incorporation in a lipid matrix having a compatible temperature profile. By way of example, when a CLP matrix is employed, the temperature profile for formation of the cubic phase is selected so as to be compatible with incorporation and stability of the membrane polypeptide. A CLP comprising a MO/water system is suitable for most membrane polypeptides stable at room temperature (~25° C.). Thermostable membrane polypeptides on the other hand may be more suited for insertion in CLP comprising a DOPE/water system having a temperature minimum profile for formation of a cubic phase of about 70° C.

Incorporation of a membrane polypeptide ligation component into a lipid matrix of interest can be accomplished in vitro and/or in vivo. When expressed ribosomally in a cell or cell free system containing a lipid membrane, the membranes and polypeptides associated therewith can be isolated together, further refined if desired, or the polypeptides separated from the membranes for subsequent reconstitution in a preformed lipid matrix following standard techniques in the art. (See, e.g., Hubbel, et al., "Membrane Protein Structure: Experimental Approaches," S. White, ed., Oxford Univ. Press, London, 1994; Kahn, et al., Biochemistry (1992) 31:6144–6151; Nowak, et al., Science (1995) 268:439–442; Turcatti, et al., J. Biol. Chem. (1996) 271(33):19991–19998; Okumura, et al., Biochimica et Biophysica Acta (1994) 1194(2):335–340; Mimms, Biochemistry (1981) 20:833–839; and U.S. Pat. No. 4,515,736). For directing a specific membrane polypeptide to a particular lipid matrix, a native or artificial targeting sequence that facilitates localization of the target polypeptide to a particular cell membrane of interest also may be included. (See., e.g., Pelham, et al., *Cell* (1993) 75:603–605; and Magee, et al., (1994) Protein Targeting: A Practical Approach, D. Rickwood and B. D. Hames, eds., Oxford University Press, Oxford).

When incorporated in a preformed lipid matrix, a target membrane polypeptide can be reconstituted following standard techniques in the art, including a preformed lipid matrix of native cell membranes, liposome, micelles, or CLPs. (See, e.g., Cladera, et al., *Eur. Biochem.* (1997) 243(3) :798–804; Takahashi, et al., *Nature Struct. Biol.* (1997) 4:44–50; Das, TK, *J. Phys. Chem.* (1996) 100:20143–20147; Angrand, et al., *Eur. J. Biochem.* (1997) 250(1):168–176; Zardeneta et al., *Anal. Biochem.* (1994) 223(1): 1–6; Landau, et al., *J. Amer. Chem. Soc.* (1993) 115:2102–2106; Portman, et al., *J. Phy. Chem.* (1991) 95:8437–8440; and Mariani, et al., *J. Mol. Biol.* (1988) 204:165–189). In particular, a target membrane polypeptide can be reconstituted in a preformed lipid matrix by controlled solubilization and/or lipid extraction techniques. For instance, the membrane polypeptide can be added to an appropriate solvent/detergent system, and extracts admixed with a preformed lipid matrix that contains or is devoid of solvent/detergent in an amount that permits solubilization and insertion of the membrane polypeptide in the lipid matrix. One or more reconstitution conditions may be adjusted to optimize the process, such as temperature, pH, water and/or organic solvent content, ion concentration, reducing or oxidizing reagents if present, as well as ratios of detergent to lipid, detergent to polypeptide, and lipid to polypeptide. An example is admixing a lipid matrix and membrane polypeptide in an appropriate buffer system with serial amounts of a detergent, and monitoring membrane polypeptide incorporation at each step of the reconstitution process to assess optimal buffer/detergent profiles for a particular lipid-membrane polypeptide reconstitution system. Examples of lipid solubilization reagents suitable for reconstitution analyses include SDS (sodium dodecyl sulfate), Triton-X100, Ammonyx-LO (N,N-dimethyl lauryl amine oxide), sodium cholate, taurocholate, sucrose monolaurate, dodecylmaltoside, CHAPS (3-(3-cholamidopropyl)-dimethylammonio-1-propanesulfonate), CHAPSO (3-[(3-cholamidopropyl) dimethylammonio]-2-hydroxy-1-propane sulfonate), octylglucoside, octylglucopyranoside and the like. (See, e.g., Rigaud, et al., *Biochimica et Biophysica Acta* (1995) 1231(3):223–246; Yang Q, et al., *Anal. Biochem.* (1994) 218(1):210–221; Scotto, et al, *Biochemistry* (1987) 26(3):833–839). If necessary, detergent can be removed following reconstitution and the content and/or activity of the reconstituted system characterized by various methods known in the art.

Reconstitution by lipid extraction can be performed through addition of isolated membrane polypeptide to a lipid matrix in an appropriate organic solvent system, such as a hexane and buffered aqueous solution, for separation of aqueous soluble phase from lipid-organic solvent soluble phase. As with the solvent/detergent solubilization method above, one or more reconstitution conditions may be adjusted to optimize the process, such as temperature, pH, water and/or organic solvent content, ion concentration, reducing or oxidizing reagents if present, as well as ratios of detergent to lipid, detergent to polypeptide, and lipid to polypeptide. The extracted lipid phase containing the membrane polypeptide can then be employed to form lipid monolayers, bilayers, liposome, micelles or CLPs by standard techniques such as sonication, layering, extrusion, centrifugation and the like depending on the lipid matrix to be obtained. Any suitable technique for reconstitution of membrane polypeptides in a lipid matrix by lipid extraction can be used. (See., e.g., Montal, et al., *Q. Rev. Biophys.* (1981) 14:1–79; Ayala, et al., *Biochimica et Biophysica Acta* (1985) 810(2):115–122; Montal, et al., *Proc. Natl Acad Sci. USA* (1990) 87:6929; Puu, et al., *Biosen Bioelectron* (1995) 10(5):463–476). For instance, the solvent system can be selected for a particular lipid-membrane polypeptide to optimize extraction, such as described above for obtention and preparation of lipids. As with the solubilization method of incorporating a membrane polypeptide in a lipid matrix, serial amounts of a chosen solvent with or without detergent and/or salts can be employed to monitor and select an optimal lipid extraction system to obtain an extracted lipid phase containing the membrane polypeptide.

The ligation label can be optionally added to the lipid matrix before, during and/or after incorporation of the membrane polypeptide depending on the ligation component pairing and its intended end use. When an aqueous-soluble ligation label is used, the label may be added to a lipid matrix that is already incorporated with a target membrane polypeptide. A soluble ligation label also can be added before and/or in conjunction with incorporation of the membrane polypeptide component in the lipid matrix, for instance, inside an aqueous compartment of a liposome, micelle or CLP. The latter is particularly advantageous when the membrane polypeptide is capable of spontaneous insertion in a preformed lipid matrix comprising a ligation label. Similarly, a lipid-soluble ligation label may be added before, during and/or after the membrane polypeptide is incorporated. As an example, when the ligation label comprises a lipid-embedding anchor domain capable of forming a complex with a lipid-embedding anchoring domain of a membrane polypeptide component, it may be desirable to incorporate the ligation label with the membrane polypeptide component before ligation so as to obtain a complex or bundle of self-assembled, yet unconnected domains. Incorporation of the membrane polypeptide and ligation components before ligation can be used to assist in insertion and/or folding of individual polypeptide segments or domains upon their interaction in the lipid matrix as well as promote proper positioning of a target ligation site. This approach also is particularly useful when the target ligation site is a compatible ligation component pairing designed to generate a modular multi-pass transmembrane polypeptide upon ligation of an extracellular and/or an intracellular loop that joins the inserted domains. Another example is the expression and insertion of the ligation label in a lipid membrane of a cell or cell free system, followed by subsequent reconstitution of the cell membrane containing the ligation label with a membrane polypeptide. To maintain the desired lipid matrix system following incorporation of the membrane polypeptide and/or ligation label, conditions such as temperature, pH, water and/or organic solvent content, ion concentration, reducing or oxidizing reagents if present, as well as ratios of detergent to lipid, detergent to polypeptide, and lipid to polypeptide can be adjusted as needed. Aliquots can be removed at specific time intervals to monitor the incorporation and integrity of the following standard techniques or those described herein.

When the membrane polypeptide and ligation label are reconstituted together, one or more of the ligation components can include a linker or capping sequence having one or more cleavage sites positioned for generating a chemically reactive ligation site moiety upon cleavage, and thus used to control the presence or absence of reactive groups needed for the ligation reaction. Additionally, reagents or buffer conditions can be utilized to control the presence and reactivity of such reactive groups. By way of example, buffer conditions with a pH of less than 6.5 also can be utilized to impede native chemical ligation. As another example, when the ligation components are designed for native chemical ligation, and thus collectively provide a complementary ligation component pairing comprising an unprotected N-terminal cysteine and a C-terminal αCOSR group, such as created after cleavage and generation of a cysteine ligation site, a thiol reducing agent such as β-mercaptoethanol may be optionally included if one chooses to delay or impede a ligation reaction. Of course the presence or absence of disulfide bonds and folding of the membrane polypeptide in the lipid matrix are taken into consideration before adding a thiol reducing agent. In general, if a disulfide bond is necessary for maintaining a properly inserted and folded membrane polypeptide, and the disulfide is sensitive to the thiol reducing agent, then the ligation label can be added just prior to ligation, thereby minimizing the need to add a reducing reagent to delay or impede ligation.

However the ligation label component is provided to the lipid matrix system, one of ordinary skill in the art will recognize that the method and order of incorporation can be adjusted for a given end use, provided that the integrity and compatibility of the lipid matrix-embedded membrane polypeptide and ligation label component pairings are maintained and capable of subsequent ligation as exemplified in any one or more of Schemes 1–2.

Once a membrane polypeptide and/or ligation label component is incorporated in a lipid matrix of interest, the matrix can be stored or further processed for ligation. For ligation, the lipid matrix-incorporated membrane polypeptide may be provided in a solution phase or attached to a solid support phase matrix. This includes liquid solutions, gels, slurries, affinity matrix support systems and the like. If the membrane polypeptide or ligation label includes a cleavage site adjacent to a residue targeted for chemoselective chemical ligation, cleavage is performed prior to the ligation reaction. Chemical or protease cleavage is performed by admixing a cleavage reagent specific for the cleavage site and incubating the mixture under the appropriate conditions and time so as obtain cleavage. Many site-specific cleavage reagents are well known and can be produced or obtained from commercial vendors. The cleaving reagent and reaction by-products can then be neutralized or removed prior to ligation if desired, so as to avoid any interference with the ligation reaction. Extent of cleavage after incubation and generation of lipid matrix-incorporated cleavage product can be determined by any number of techniques known in the art or described herein. Of course it will be understood that the product of the cleavage reaction targeted for chemical ligation will contain an unprotected amino acid residue amenable to a particular type of ligation chemistry, whether the product is the ligation label and/or the membrane polypeptide. By way of example, a cleavage product designed for native chemical ligation will preferably contain an unprotected N-terminal cysteine, or in some instances only an appropriately positioned unprotected amino acid is needed for native chemical ligation to a membrane polypeptide or ligation label donating a C-terminal thioester moiety.

For the ligation reaction, reaction conditions are selected that maintain the desired interaction of the lipid matrix-embedded membrane polypeptide and ligation label components. Routine adjustments to identify optimal conditions can be made, for instance, by varying individual reagents, concentrations, temperatures and the like. For example, reaction conditions may be adjusted to optimize ligation, such as temperature, pH, water and/or organic solvent content, ion concentration, reducing or oxidizing reagents if present, as well as ratios of detergent to lipid, detergent to polypeptide, and lipid to polypeptide. Addition or exclusion of reagents that solubilize the lipid matrix and/or the membrane polypeptide to different extents may further be used to control the specificity and rate of the desired ligation reaction. One of ordinary skill will recognize that these conditions are selected based on a given ligation chemistry utilized, and thus conditions appropriate to that chemistry. Such conditions and ranges of conditions are readily determined by one of ordinary skill in the art.

Any number of techniques can monitor formation and the homogeneity of the desired lipid matrix-membrane polypeptide and/or ligation label component system, as well as formation of a desired ligation product. These techniques include assays that detect activity of the inserted membrane polypeptide, fluorescence spectroscopy, mass spectrometry, affinity matrix and ligand binding assays, NMR, circular dichroism (CD), scanning densitometry, calorimetry, and various chromatography techniques such as electrophoresis, affinity chromatography, HPLC using either reverse phase or ion exchange columns, and the like.

A lipid matrix comprising a pre-ligation or post-ligation product can be stored for later use or directly employed in an assay. When stored, the method of storage is selected to retain stability of the lipid matrix and its incorporated components. This includes storage in a frozen form, in the form of a lyophilized powder, crystal, gel, slurry, liquid, or in any other suitable form, including storage on a support matrix such as a film or affinity matrix. For example, a lipid matrix fraction derived from a native cell membrane, unless highly purified, is typically frozen if intended for long term storage. Artificial lipid matrices such as liposomes and CLPs are somewhat more amenable to a range of storage options, particularly CLPs, which may be stored as viscous gels under conditions that favor the cubic phase of the lipid system. When provided as a closed vesicle, such as a liposome, aggregation and fusion may be reduced by adding negative and/or positively charged components to the composition following standard techniques. Introducing lipids that have a higher transition temperature, such as cholesterols or saturated fatty acid containing phospholipids, also may reduce leakage of closed vesicles. Additives such as trehalose may also be employed as a cryoprotector. Of course any suitable method for storing preformed lipid systems known in the art can be used and storage stability in general can be improved by regulating temperature and moisture content, reducing contacts with raw materials or with oxidants, such as by storing under an inert gas, dispersing the lipid matrices in a neutral buffer system and/or eliminating residual solvents.

For employment in an assay, the chemical ligation methods and compositions of the invention can be utilized in a screening assay of the invention. Screening assays of the invention are characterized by binding of a ligand to a target lipid matrix-embedded membrane polypeptide produced by one or more of the methods and compositions of the invention.

In a preferred embodiment, at least one ligation component is provided with one or more detectable moieties, also referred to as a detectable label or probe, such as an isotope, hapten, or chromophore including fluorophores, heavy metal complexes with aromatic ligands or chelate ligands and the like. More preferably, at least one first detectable label is incorporated into the membrane polypeptide by a chemoselective chemical ligation approach exemplified in any one or more of Schemes 1–2. If desired, one or more of a second detectable label can be incorporated into the membrane polypeptide, the lipid matrix, and/or a ligand for the polypeptide by any number of techniques in addition to Schemes 1–2. As described above, a detectable moiety can be incorporated in a ligation component during and/or after synthesis, including after ligation in the lipid matrix, by any technique suitable for such purpose, provided the reactivity, selectivity and stability of the lipid matrix-incorporated membrane polypeptide and/or ligation component system exemplified in any one or more of Schemes 1–2 is substantially maintained. As also described above, one or more residues targeted for covalent attachment of a detectable label can be selected during the design and screening of the compatible ligation component pairings.

Chemical synthesis is the preferred method to incorporate a detectable label. In this embodiment, chemical synthesis is utilized to incorporate at least one detectable label in a pre-ligation component exemplified in any one or more of Schemes 1–2. In this way the resulting lipid-membrane embedded ligation product can be designed to contain one or more detectable labels at pre-specified positions of choice. Isotopic labels detectable by NMR are of particular interest. Also of particular interest is the incorporation of one or more unnatural amino acids comprising a detectable label at one or more specific sites in a target ligation component of interest. By unnatural amino acid is intended any of the non-genetically encoded L-amino acids and D-amino acids that are modified to contain a detectable label, such as photoactive groups, as well as chromophores including fluorophores and other dyes, or a hapten such as biotin. Unnatural amino acids comprising a chromophore and chemical synthesis techniques used to incorporate them into a peptide or polypeptide sequence are well known, and can be used for this purpose. For example, it may be convenient to conjugate a fluorophore to the N-terminus of a resin-bound peptide before removal of other protecting groups and release of the labeled peptide from the resin. Fluorescein, eosin, Oregon Green, Rhodamine Green, Rhodol Green, tetramethylrhodamine, Rhodamine Red, Texas Red, coumarin and NBD fluorophores, the dabcyl chromophore and biotin are all reasonably stable to hydrogen fluoride (HF), as well as to most other acids, and thus suitable for incorporation via solid phase synthesis. (Peled, et al., *Biochemistry* (1994) 33:7211; Ben-Efraim, et al., *Biochemistry* (1994) 33:6966). Other than the coumarins, these fluorophores also are stable to reagents used for deprotection of peptides synthesized using Fmoc chemistry (Strahilevitz, et al., *Biochemistry* (1994) 33:10951). The t-Boc and α-Fmoc derivatives of ε-dabcyl-L-lysine also can be used to incorporate the dabcyl chromophore at selected sites in a polypeptide sequence. The dabcyl chromophore has broad visible absorption and can used as a quenching group. The dabcyl group also can be incorporated at the N-terminus by using dabcyl succinimidyl ester (Maggiora, et al., *J Med Chem* (1992) 35:3727). EDANS is a common fluorophore for pairing with the dabcyl quencher in FRET experiments. This fluorophore is conveniently introduced during automated synthesis of peptides by using 5-((2-(t-Boc)-γ-glutamylaminoethyl) amino) naphthalene-1-sulfonic acid (Maggiora, et al., *J. Med. Chem.* (1992) 35:3727). An α-(t-Boc)-ε-dansyl-L-lysine can be used for incorporation of the dansyl fluorophore into polypeptides during chemical synthesis (Gauthier, et al., *Arch Biochem. Biophys.* (1993) 306:304). As with EDANS fluorescence of this fluorophore overlaps the absorption of dabcyl. Site-specific biotinylation of peptides can be achieved using the t-Boc-protected derivative of biocytin (Geahlen, et al., *Anal. Biochem.* (1992) 202:68), or other well known biotinylation derivatives such as NHS-biotin and the like. Racemic benzophenone phenylalanine analog also can be incorporated into peptides following its t-Boc or Fmoc protection (Jiang, et al., *Intl. J. Peptide Prot. Res.* (1995) 45:106). Resolution of the diastereomers can be accomplished during HPLC purification of the products; the unprotected benzophenone also can be resolved by standard techniques in the art. Keto-bearing amino acids for oxime coupling, aza/hydroxy tryptophan, biotyl-lysine and D-amino acids are among other examples of unnatural amino acids that can be utilized. It will be recognized that other protected amino acids for automated peptide synthesis can be prepared by custom synthesis following standard techniques in the art.

Other detectable labels can be incorporated into the membrane polypeptide, the lipid matrix, and/or a ligand for the polypeptide by a technique in addition to those exemplified in Schemes 1–2. In this embodiment, the detectable moiety typically is introduced post-chemical ligation. This can be done by chemical modification using a reactive substance that forms a covalent linkage once having bound to a reactive group of the target molecule. For example, a peptide or polypeptide ligation component can include several reactive groups, or groups modified for reactivity, such as thiol, aldehyde, amino groups, suitable for coupling the detectable label by chemical modification (Lundblad, et al., In: Chemical Reagents for Protein Modification, CRC Press, Boca Raton, Fla., (1984)). Site-directed mutagenesis and/or chemical synthesis also can be used to introduce and/or delete such groups from a desired position. Any number of detectable labels including biotinylation probes of a biotin-avidin or streptavidin system, antibodies, antibody fragments, carbohydrate binding domains, chromophores including fluorophores and other dyes, lectin, nucleic acid hybridization probes, drugs, toxins and the like, can be coupled in this manner. For instance, a low molecular weight hapten, such a fluorophore, digoxigenin, dinitrophenyl (DNP) or biotin, can be chemically attached to the membrane polypeptide or ligation label component by employing haptenylation and biotinylation reagents. The haptenylated polypeptide then can be directly detected using fluorescence spectroscopy, mass spectrometry and the like, or indirectly using a labeled reagent that selectively binds to the hapten as a secondary detection reagent. Commonly used secondary detection reagents include antibodies, antibody fragments, avidins and streptavidins labeled with a fluorescent dye or other detectable marker.

Depending on the reactive group, chemical modification can be reversible or irreversible. A common reactive group targeted in peptides and polypeptides are thiol groups, which can be chemically modified by haloacetyl and maleimide labeling reagents that lead to irreversible modifications and thus produce more stable products. For instance, reactions of sulfhydryl groups with α-haloketones, amides, and acids in the physiological pH range (pH 6.5–8.0) are well known and allow for the specific modification of cysteines in peptides and polypeptides (Hermason, et al., In: Bioconjugate Techniques, Academic Press, San Diego, Calif., pp. 98–100, (1996)). Covalent linkage of a detectable label also can be triggered by a change in conditions, for example, in photo-affinity labeling as a result of illumination by light of an appropriate wavelength. For photoaffinity labeling, the label, which is often fluorescent or radioactive, contains a group that becomes chemically reactive when illuminated (usually with ultraviolet light) and forms a covalent linkage with an appropriate group on the molecule to be labeled. An important class of photoreactive groups suitable for this purpose is the aryl azides, which form short-lived but highly reactive nitrenes when illuminated. Flash photolysis of photoactivatable or "caged" amino acids also can be used for labeling peptides that are biologically inactive until they are photolyzed with UV light. Different caging reagents can be used to modify the amino acids, such derivatives of o-nitrobenzylic compounds, and detected following standard techniques in the art. (Kao, et al., "Optical Microscopy: Emerging Methods and Applications," B. Herman, J. J. Lemasters, eds., pp. 27–85 (1993)). The nitrobenzyl group can be synthetically incorporated into the biologically active molecule via an ether, thioether, ester (including phosphate ester), amine or similar linkage to a hetero atom (usually O, S or N). Caged fluorophores can be used for photoactivation of fluorescence (PAF) experiments, which are analogous to fluorescence recovery after photobleaching (FRAP). Those caged on the E-amino group of lysine, the phenol of tyrosine, the γ-carboxylic acid of glutamic acid or the thiol of cysteine can be used for the specific incorporation of caged amino acids in the sequence. Alanine, glycine, leucine, isoleucine, methionine, phenylalanine, tryptophan and valine that are caged on the α-amine also can be used to prepare peptides that are caged on the N-terminus or caged intermediates that can be selectively photolyzed to yield the active amino acid either in a polymer or in solution. (Patchornik, et al., *J Am Chem Soc* (1970) 92:6333). Spin labeling techniques of introducing a grouping with an unpaired electron to act as an electron spin resonance (ESR) reporter species may also be used, such as a nitroxide compound (—N—O) in which the nitrogen forms part of a sterically hindered ring (Oh, et al., supra).

Selection of a detectable label system generally depends on the assay and its intended use. In particular, the chemical ligation methods and compositions of the invention can be employed in a screening assay of the invention characterized by binding of a ligand to a lipid matrix-embedded membrane polypeptide comprising a ligation label joined through a covalent bond to the membrane polypeptide ligation site. These include diagnostic assays, screening new compounds for drug development, and other structural and functional assays that employ binding of a ligand to a prefolded membrane polypeptide. The ligands may be derived from naturally occurring ligands or derived from synthetic sources, such as combinatorial libraries. Screening methods of particular interest involve detection of ligand binding to a lipid matrix-embedded membrane polypeptide, as produced by a method of the invention, by fluorescence spectroscopy.

In a preferred embodiment, screening for binding of a ligand to a lipid matrix-embedded membrane polypeptide comprising one or more chromophores is performed in an assay characterized by detecting fluorescence resonance energy transfer (FRET). Ligand binding to the lipid matrix-embedded membrane polypeptide can be measured by any number of methods known in the art for FRET analyses, including steady state and time-resolved fluorescence by monitoring the change in fluorescence intensity, emission energy and/or anisotropy, for example, through energy transfer from a donor moiety to an acceptor moiety of the FRET system. (See, e.g., Wu, et al., *Analytical Biochem.* (1994) 218:1–13). FRET assays allow not only distance measurements, but also resolution of the range of donor-to-acceptor distances. FRET also can be used to show that the membrane polypeptide exists alternately in a single conformational state, or with a range of donor-to-acceptor distances when in a different state, such as when bound to a ligand.

For FRET assays, the lipid-matrix-incorporated membrane polypeptide is designed to contain at least one chromophore of a donor-acceptor system. The donor molecule is always a fluorescent (or luminescent) one for detection. The acceptor molecule can be either fluorescent or non-fluorescent. Thus for a donor-acceptor system, at least two chromophores are provided: the first is provided by the lipid matrix-embedded membrane polypeptide; the second can be provided by the membrane polypeptide, the lipid matrix, or by a ligand for the polypeptide.

More than one donor-acceptor pairing may also be included. For example, the membrane polypeptide may contain one or more donor and/or acceptor molecules, and preferably at least one donor molecule comprising a chromophore. A ligand may comprise one or more donor or acceptor molecules as well. The lipid membrane matrix also may contain one or more donor or acceptor molecules, as well as secondary molecules incorporated into the lipid and/or solvent accessible channels formed by the matrix that are ligands of the target polypeptide of interest, such as G-proteins when the target membrane polypeptide comprises part or all of a seven-transmembrane receptor system.

In a preferred embodiment, the membrane polypeptide comprises one or more donor molecules and a ligand for the membrane polypeptide comprises one or more acceptor molecules. The ligands can be small organic molecules, peptides, peptide mimetics, constrained peptides, polypeptides and the like. They may be derived from naturally occurring ligands or derived from synthetic sources, such as combinatorial libraries. When a ligand is a peptide or polypeptide, it can be prepared with a chromophore label using various chemistries, such as those described herein. Of particular interest are modular "cross-over" polypeptide ligands, which can be constructed to comprise one or more chromophores produced by combining one or more functional modules from a first polypeptide and at least one second polypeptide. Synthesis of modular polypeptides is described in Kent, et al., WO 99/11655.

Ligands of particular interest compete for binding to a ligand binding site on a lipid matrix-embedded membrane polypeptide produced by any one or more of the methods and/or compositions exemplified in Schemes 1–2. These ligands can be employed in an additional method of the invention that involves contacting a lipid matrix-embedded membrane polypeptide with two or more different ligands that compete for binding to a ligand binding site of the membrane polypeptide. One or more of the different competition ligands can be labeled for detection purposes. As an example, the membrane polypeptide can be labeled with a first chromophore and a competition ligand can be labeled with a second chromophore of a donor-acceptor system. Alternatively, the membrane polypeptide or the lipid matrix can provide the second chromophore. Competition for ligand binding to the polypeptide is monitored by FRET analysis, including monitoring changes in intrinsic fluorescence of the membrane polypeptide upon binding ligand, and/or changes in the properties of a fluorescent-labeled ligand upon binding, and thus ligand binding can be detected and characterized.

When choosing a chromophore donor-acceptor pair for FRET, positioning of the first chromophore in a target polypeptide is designed to be within a sufficient distance of a second chromophore to create a donor-acceptor fluorescence resonance energy transfer system. For instance, energy transferred from the donor to an acceptor involves coupling of dipoles in which the energy is transferred over a characteristic distance called the Forster radius ($R_0$), which is defined as the distance at which energy transfer efficiency is 50% (i.e., distance at which 50% of excited donors are deactivated by FRET). This distance is referred to herein as the Forster distance. These distances range from about 10 to 100 Angstroms (Å), which is comparable to the diameter of many proteins and comparable to the thickness of membranes. Intrinsic tryptophan or tyrosine sometimes may be used as chromophores in distance measurements, but in most cases the Forster distance is limited to above 30 Å. However, an acceptor molecule comprising clusters of acceptors with high molar absorption coefficient for each acceptor may achieve a further extension of Forster distance. Thus average distances over 100 Å can be measured. As the Forster distances can be reliably calculated from the absorption spectrum of the acceptor and the emission spectrum of the donor, FRET allows determination of molecular distances. Once the Forster distance is known, the extent of energy transfer can be used to calculate the donor-to-acceptor distance.

Donor-acceptor chromophores applicable for biological molecules, and for which Forster distances are known when paired, include but are not limited to the following chromophores: ANAI (2-anthracence N-acetylimidazole); BPE (B-phycoerythrin); CF (caboxyfluorescein succinimidyl ester); CPM (7-diethylamino-3-(4'-maleimidylphenyl)-4-methylcoumarin); CY5 (carboxymethylindocyanine-N-hydroxysuccinimidyl ester, diI-$C_{13}$, 1,1'-dioctadecyl-3,3,3'3', -tetramethyl-indocarbocyanine; diO—$C_{14}$, 3,3'-ditetradecyloxacarbocyanine); DABM (4-dimethylaminophenylazo-phenyl-4'-maleimide); DACM ((7-(dimethylamino)coumarin-4-yl)-acetyl); DANZ (dansylaziridine); DDPM (N-(4-dimethylamino-3,5-dinitrophenyl)maleimide); DMAMS (dimethylamino-4-maleimidostilbene); DMSM (N-(2,5-dimethoxystiben-4-yl)-maleimide); DNP (2,4-dinitrophneyl); ε-A (1, $N^6$-ethenoadenosine); EIA (5-(iodoacetetamido) eosin); EITC (eosin thiosemicarbazide); $F_2$DNB (1,5-difluro-2,4'-dinitrobenzene); $F_2$DPS (4,4'-difluoro-3,3'-dinitrophenylsulfone); FITC (fluorescein-5-isothiocyanate); FM (fluorescein-5-maleimide); FMA (fluorescein mercuric acetate); FNAI (fluorescein N-acetylimidazole); FTS (fluorescein thiosemicarbazide); IAANS (2-(4'-iodoacetamido)amino)naphthalene-6-sulfonic acid); IAEDANS (5-(2-((iodoacetyl)amino)ethyl)amino)-naphthlene-1-sulfoni acid); IAF (5-iodoacetamidofluorescein); IANBD (N-((2-(iodoacetoxy)ethyl)-N-methyl)amino-7-nitrobenz-2-oxa-1,3-diazole); IPM (3(4-isothiocyanatophenyl)7-diethyl-4-amino-4-methylcoumarin); ISA (4-(iodoacetarnido)salicylic acid); LRH (lissaminerhodamine); LY (Lucifer yellow); mBBR (monobromobimane); MNA ((2-methoxy-1-naphthyl)-methyl); NAA (2-naphthoxyacetic acid); NBD (7-nitro-2,1,3-benzoxadiazol-4-yl); NCP (N-cyclohexyl-N'-(1-pyrenyl)carbodiimide); ODR (octadecylrhodamine); PM (N-(1-pyrene)-maleimide); SRH (sulforhodamine); TMR (tetramethylrhodamine); TNP (trinitrophenyl); TR (Texas red); BODIPY ((N1-B)-N 1'-(difluoroboryl)-3,5'-dimethyl-2-2'-pyrromethene-5-propionic acid, N-succinimidyl ester); and lanthanide-ion-chelates such as an iodoacetamide derivative of the $Eu^{3+}$-chelate of N-(p-benzoic acid) diethylenetriamine-N,N',N'-tetraacetic acid (DTTA); Eu-DTPA-cs124 and Tb-DTPA-cs124 (Eu-chelate and Tb-chelate of diethylenetriaminepentaacetic acid, carbostyril 124); Eu-TTHA-cs 124 (Eu-chelate of triethylenetetraaminehexaacetic acid, carbostyril 124); Eu-DOTA (Eu-chelate of 1,4,7,10 tetraazacyclodedecane N,N',N'',N'''tetraacetic acid); Eu-DTPA-AMCA (Eu-chelate of diethylenetriaminepentaacetic acid, 7-amino 4-methyl coumarin); and Cy5 and Cy5.5 (cyanine dye cy5 and cy5.5).

Since energy transfer measurement is most sensitive to distance variation when donor-acceptor separation is close to their Forster distance, the membrane polypeptide comprising the first chromophore of a donor-acceptor pair system is selected or engineered so that the first and second chromophores approach or are at the Forster distance. Table 1 shows some typical Forster distances of donor-acceptor pairs, with select ones shown as measured in $H_2O$ and $D_2O$ (Selvin et al., *Proc. Natl. Acad. Sci. USA* (1994) 91:10024–10028; Li, et al., *J. Amer. Chem. Soc.* (1995) 117:8132–8138; and Heyduk, et al., *Anal. Biochem.* (1997) 248:216–227) for comparison.

TABLE 1

| DONOR | ACCEPTOR | FORSTER DISTANCE (Å) |
| --- | --- | --- |
| Fluorescein | Tetramethyllrhodamine | 55 |
| IAEDANS | Fluorescein | 46 |
| EDANS | DABCYL | 33 |
| Fluorescein | Fluorescein | 44 |
| BODIPY FL | BODIPY FL | 57 |
| Tb-DTPA-cs124 | TAMRA | 60 ($H_2O$)/65($D_2O$) |
| Eu-TTHA-cs124 | Cy5 | 68.6($H_2O$)/73.5($D_2O$) |
| Eu-DTPA-cs124 | Cy5 | 56($H_2O$)/70($D_2O$) |
| Eu-DOTA | Cy5.5 | 62($H_2O$)/76($D_2O$) |
| Eu-DTPA-AMCA | Cy5 | 55($H_2O$)/61.4($D_2O$) |

Extensive compilations of Forster distances for various donor-acceptor pairs and their specific applications in FRET analysis of biological molecules including peptides, polypeptides, carbohydrates and lipids are well known in the art. (See, e.g., Wu, et al., supra; Berlman, et al., (1973) Energy Transfer Parameters of Aromatic Compounds, Academic Press, New York; Van der Meer, et al., (1994) "Resonance Energy Transfer Theory and Data," VCH Publishers; Fairclough, et al.,*J. Muscle Res. Cell Motility* (1987) 8:97; des Remedios, et al., *Meth. Enzymol.* (1978) 48:347). These Forster distances are used as a general guide when selecting a particular donor-acceptor pair.

In addition to selecting donor and acceptor moieties that are in close proximity (typically 10–100 Å) and approach or are at the Forster distance, the FRET chromophore pairs are selected so that the absorption spectrum of the acceptor overlaps the fluorescence emission spectrum of the donor, and the donor and acceptor transition dipole orientations are approximately parallel. Moreover, for anisotropy assays in which two identical chromophores are employed, where one is provided by the membrane polypeptide and a second by a ligand, the chromophores are preferably positioned so that tumbling of the donor or acceptor moiety is minimized. In a preferred embodiment, at least one chromophore is positioned in a rigid portion of the lipid matrix-embedded membrane polypeptide and/or ligation label component, such as in an α-helix or β-sheet portion. A chromophore positioned and anchored between two cysteine residues about 2–3 Å apart in an α-helix or β-sheet is particularly suited for this purpose. An advantage of reducing chromophore tumbling is increased sensitivity in FRET detection by reducing background noise in the spectrum.

For most applications, the donor and acceptor dyes are different, in which case FRET can be detected by the appearance of sensitized fluorescence of the acceptor (acceptor enhancement), by quenching of donor fluorescence (donor quenching), or fluorescence polarization (anisotropy). When the donor and acceptor are the same, FRET is typically detected by anisotropy. For instance, donor quenching (quenching of fluorescence) can be used to detect energy transfer. Excitation is set at the wavelength of donor absorption and the emission of donor is monitored. The emission wavelength of donor is selected such that no contribution from acceptor fluorescence is observed. The presence of acceptor quenches donor fluorescence. A wide variety of small molecules or ions act as quenchers of fluorescence, that is, they decrease the intensity of the emission. These substances include iodide, oxygen, chlorinated hydrocarbons, amines, and disulfide groups. The accessibility of fluorophores to quenchers is widely used to determine the location of probes on macromolecules, or the porosity of proteins and membranes to the quenchers. For example, the intensity of polypeptide- and membrane-bound fluorophores in the presence of dissolved water-soluble quenchers can be measured by donor quenching. Lipid-soluble quenchers, such as brominated fatty acids, also can be added to assess the interior acyl side chain region of membranes.

Acceptor enhancement detection techniques can be used when an acceptor is fluorescent, and its fluorescence intensity is enhanced when energy transfer occurs (with excitation into the donor). This provides additional methods to visualize energy from a fluorescence spectrum. In an emission spectrum, one excites at the wavelength of donor absorption and observes the intensity increase of acceptor. In an excitation spectrum, one sets detection at the acceptor emission wavelength and observes enhancements of intensity at a wavelength range where donor absorbs.

Anisotropy (or fluorescence polarization) analysis using FRET is of particular interest, for instance, where two identical chromophores are attached to a lipid matrix-embedded membrane polypeptide and a water-soluble ligand. The polarization properties of light and the dependence of light absorption on the alignment of the fluorophores with the electric vector of the incident light provide the physical basis for anisotropic measurements. Fluorescence probes usually remain in the excited state from 1 to 100 nanoseconds (ns), a duration called the fluorescence lifetime. Because rotational diffusion of polypeptides also occurs in 1–100 ns, fluorescence lifetimes are a favorable time scale for studies of the associative and/or rotational behavior of macromolecules. Other probes such as probes with lifetimes of several 100 microseconds include, but are not limited to: $[Ru(bpy)_2 dcbpy)]^{2+}R$, where bpy is bispyridine, dcbpy is 4.4'dicarboxyl bpy; $[Os(bpy)_2(dcbpy)]^{2+}$; and $(L)Re(CO)_3 C=NR$, where L is 1,10 phenanthroline or bpy, R is n-Bu or t-Bu, and Bu is Butyl. A review of these complexes and references to them can be found in Terpetsching, et al., (*Meth. Enzymol.* (1997) 278:295). Thus, when a sample of a lipid matrix-embedded membrane polypeptide comprising an appropriate donor-acceptor chromophore pair is illuminated with vertically polarized light, the emission can be polarized. When energy transfer occurs between the same molecules in identical environments, fluorescence intensity or lifetime does not change. The anisotropy on the other hand may change due to likely differences in spatial orientation between the membrane-polypeptide and ligand attached chromophores.

Of particular interest for anisotropic assays is the ability to rotationally restrict chromophores along their linker arms by providing two attachment sites such as two residues spaced by three intervening residues along an α-helix. Such a design prevents attached chromophores from freely rotating around the linker arm and thus prevents a loss of spatial information from anisotropy assays. If a polypeptide binds a ligand, the membrane polypeptide-bound and the ligand-chromophore (and their respective dipoles) have a defined spatial orientation with respect to one another. More importantly, their relative orientation undergoes little fluctuation if the chromophore is rigidly attached. Since the signal-to-noise ratio of an anisotropy-detected experiment is a direct function of the extent of orientational fluctuation, rigid attachment of the chromophore allows one to detect FRET via anisotropy with a higher sensitivity.

In another embodiment of the invention, methods and compositions are provided for labeling polypeptides with chelator-sensitized time-resolved metal ion probes, such as coumarin-sensitized time-resolved lanthanide probes. This aspect of the invention provides method and compositions for site-specific labeling of any peptide or polypeptide amenable to solid-phase chemical synthesis or a combination of solid-phase chemical synthesis and chemical ligation techniques, including soluble and membrane peptides and polypeptides, with a sensitized zwitterionic metal ion chelator complex (MCC) for detection of time-resolved luminescence in FRET and high throughput screening assays. The method involves labeling one or more amino acids of a peptide or polypeptide chain that is attached to a chemical synthesis resin with a zwitterionic chelator moiety capable of chelating metal ions. Thus, a chelator moiety is attached to the peptide or polypeptide chain concurrent with on-resin chemical synthesis. The metal ions may then be complexed with the chelator moiety on-resin, or after the peptide or polypeptide chain is cleaved from the resin, depending on its intended end use. Chelator moieties suitable for this method include, but are not limited to, zwitterionic chelating agents from the group of TTHA (triethylenetetraminehexaacetic acid), DTPA (diethylenetriaminepentaacetic acid), DTTA (diethylenetriamine N,N,N,N tetraacetic acid), DOTA (1,4,7,10 tetraazacyclododecance N,N',N'',N''' tetraacetic acid), TETA (1,4,8,11 tetraazacyclotetradecane N,N',N'',N''' tetraacetic acid) and any other zwitterionic chelator ligands for binding metals. Metal ions of particular interest are lanthanide ions, and more particularly Terbium ($Tb^{3+}$), Samarium ($Sm^{3+}$), and Europium ($Eu^{3+}$).

Also provided is a method to increase the solubility of zwitterionic chelating agents including, zwitterionic chelating agents from the group of TTHA, DTPA, DTTA, DOTA, TETA and any other zwitterionic chelator ligands for binding metals. This aspect of the invention involves combining an insoluble zwitterionic chelating agent with a solubilizing agent that produces a soluble salt form of the zwitterionic chelating agent. This method is applicable for any zwitterionic chelating agent having insufficient solubility in commonly used solvents such as dimethylformamide (DMF), dimethylsulfoxide (DMSO), methanol and the like. In a preferred embodiment, the zwitterionic chelating agent to be solubilized comprises a carboxyl group that is to be activated for a given subsequent coupling reaction, and the solubilizing agent is inert to activation. The preferred solubilizing agent is trifluoroacetic acid (TFA). For example, combination of the zwitterionic chelator TTHA with TFA yields the TFA salt of TTHA that can be prepared and stored as a lyophilized powder that very readily dissolves in DMF, which is commonly employed in on-resin chemical synthesis. Another example is of a solubilizing agent is para-toluene sulfonic acid (TSA). Compared to TFA, the TSA has the advantageous properties of not only being a strong acid, but it also is non-volatile and non-nucleophilic. It will be appreciated that combinations of solubilizing agents also may be employed depending on the intended end use. By employing the soluble salt of a zwitterionic chelator in on-resin labeling of peptides or polypeptides, the reaction yields are significantly improved by increasing the concentration of the soluble chelator available for reaction. Also provided is a composition comprising a soluble salt form of a zwitterionic chelator. The preferred soluble salt form of a zwitterionic chelator is TFA salt of a zwitterionic chelator. Another soluble salt form of a zwitterionic chelator is TSA salt of a zwitterionic chelator. This includes, but is not limited to, TFA and TSA salts of zwitterionic chelating agents from the group of TTHA, DTPA, DTTA, DOTA, TETA and any other zwitterionic chelator ligands for binding metals.

On-resin labeling of peptides and polypeptides with chelator-sensitized time-resolved metal ion probes permits site-specific labeling, high purity by removal of residual reaction components and dye, and unprecedented yield. This avoids previous problems in which a peptide or polypeptide is labeled after recombinant production or labeling after assembly of the chain by chemical synthesis. For instance, labelirg of folded peptide or polypeptide with dye or other label often causes non-specific, non-covalent binding of the label. In contrast, with the on-resin chelator labeling method of the invention it is much easier to control and characterize where the label is positioned using solid-phase attachment. This is because all sites of potential side-reactions are protected on the resin as opposed to unprotected in traditional labeling of folded peptides or polypeptides; the lipid matrix-assisted chemical ligation approach of the invention also can provide this advantage, such as when chelator complex preparation is utilized in conjunction with chemoselective hydrazone or similar attachment. Solid phase synthesis and on resin labeling of the method also is followed by multiple washes with organic solvent, minimizing (essentially eliminating) any residual dye or other label that could non-covalently bind. With regard to yield, prior approaches of post-resin labeling with lanthanide ion chelator complexes typically provide a reaction yield of about 10–50% for complexation involving coupling of sensitizor to dye (e.g., coupling of AMCA-X or carbostyril cs124 (7-amino,4-methyl-2(1H)-quinoline) to TTHA or DTPA (diethylenetriaminepentaacetic acid) sensitized complex (TTHA yield reported to be about 10–25%, and DTPA yield reported to be about 40–50%); see, e.g., Heyduk, et al., *Anal. Biochem.* (1997) 248:214; Li, et al., *Am. Chem. Soc.* (1995) 116:8132; and Mathis, et al., *Clin. Chem.* (1995) 41:1391. By way of contrast, the on-resin labeling method of the present invention is basically complete (>95%). This extraordinary difference in yield is due in part to (1) the inherent advantage of solid-phase synthesis in a gel material that perfectly solvates reagents, and (2) the ability to achieve high concentration of chelator (e.g., TTHA) in DMF by prior conversion of chelator to the TFA salt. Other advantages include its ease of preparation. For example, attachment of the label on-resin takes a few steps of solid-phase synthesis. All following steps such as ligation, purification and folding are identical as for native protein. In contrast, labeling of folded protein requires potentially extensive purification work to remove unreacted material.

The methods and compositions of the invention have tremendous potential for therapeutic applications, as they can be used in diagnostic assays as well as in drug discovery, for example, in high throughput screening of compound libraries that contain ligands for membrane polypeptides of interest. The invention is widely applicable for synthesis and structure/function study of folded membrane polypeptides, including single-pass and multi-pass membrane polypeptides. This includes the detectable labeling and modular assembly of membrane polypeptides from separately synthesized and folded extra-membranous and transmembrane domains. Furthermore, recombinant polypeptides that include a native or engineered cleavage site adjacent to a targeted chemoselective ligation site residue can be cleaved and ligated to almost any desired peptide using a semi-synthetic approach. Thus, the present invention allows for the incorporation of a vast variety of molecular tools such as spectroscopic probes, unnatural amino acids and molecular markers at yields that significantly exceed those achieved with currently available techniques.

Exploiting the physical and chemical properties of a lipid matrix in combination with the diversity, specificity and yield of chemoselective chemical ligation techniques provides access to virtually any membrane polypeptide comprising one or more suitable chemoselective ligation sites, whether the sites are engineered and/or occur naturally. This includes access to single or multiple transmembrane domains connected to extra-membranous domains, such as N-terminal and C-terminal sequences, and/or internal loops that extend out of the membrane bilayer. As an example, extra-membrane loops can be shortened, cut, or elongated with segments forming proteolytic cleavage sites, foreign epitopes, extra-transmembrane segments, or even whole proteins systems, for example, to facilitate purification, biochemical/biophysical studies, or crystallogenesis. Transmembrane segments, such as $\alpha$-helices, also can be deleted, duplicated, exchanged, transported into a foreign context or replaced with synthetic peptides, in order to characterize their integration into, and assembly in, the membrane and their function. Insertion of residues that serve as a subsequent target of a chemoselective ligation chemistry of interest also can serve as the basis for a great diversity of experiments, ranging from the exploration of secondary, tertiary and quaternary structures of the transmembrane region to the creation of anchoring points for reporter molecules that are joined to a prefolded membrane polypeptide through a ligation label comprising a covalent bond at the ligation site. Since the methods and compositions of the invention are amenable to chemical synthesis, and given the small size of many folding domains in membrane polypeptides, particularly $\alpha$-helical domains, modular synthesis of multi-pass membrane polypeptides is possible.

Moreover, methods and compositions of the invention can be exploited for resonance energy transfer measurements by FRET analyses. This includes access to donor-acceptor chromophore systems that can be used as a qualitative or a quantitative tool to detect and characterize interactions between a folded lipid matrix-embedded membrane polypeptide and a ligand for the polypeptide, such as a membrane bound receptor-ligand system. The principles and applications of employing resonance energy transfer systems are many and well known, and thus are readily exploited using the methods and compositions of the invention. For instance, lipid matrix-assisted chemical ligation and synthesis can be exploited to create a chromophore donor/acceptor system that enables detection through FRET. Since measurement of energy transfer is based on fluorescence detection, the assays are highly sensitive and can be used to detect ligand binding when the labeled membrane polypeptide is a receptor for the ligand. Additionally, atomic structural information for membrane polypeptides can be obtained regardless of the complexity or heterogeneity of the system. Since the time scale of resonance energy transfer can be on the order of nanoseconds to microseconds, many processes including slow conversion of conformers that are time-averaged in other techniques can be resolved. This approach can be used to infer the spatial relation between donor and acceptor chromophores to obtain structural information, including ligand-induced conformational changes. In addition to data acquisition with a conventional spectrophotofluorometer, the FRET methods can be adapted for multiple in vitro and in vivo assays including liquid chromatography, electrophoresis, microscopy, and flow cytometry etc. Thus, the present invention can be used for both in vitro and in vivo assays. The methods also can be applied as a simple diagnostic tool, as well as used in the study of membrane structure and dynamics, or extend it to molecular interactions on cell surfaces or in single cells.

Lipid matrix-assisted chemical ligation and membrane polypeptide synthesis also can be exploited for "D-target" screening. Many drugs are targeted at integral membrane polypeptides, such as receptors, particularly G-protein coupled receptors, and ion channels. Such drugs are typically either chiral small molecules often natural-product derived (usually receptor antagonists), or chiral {peptide, polypeptide, or carbohydrate} molecules. These latter biomolecular ligands can have either agonist or antagonist effects on the integral membrane polypeptide depending on the properties of a particular system. See, for example, Kent, et al., WO 93/25667.

All naturally occurring polypeptides are made up exclusively of L-amino acids plus the achiral amino acid glycine. (Very rarely an amino acid may be chirally inverted to the opposite "D-" configuration by post-translational enzymatic action.) Thus, natural polypeptides are made up of polypeptide chains exclusively of the L-configuration. The chiral polypeptide chain folds to form a defined three dimensional structure characteristic of a particular polypeptide molecule. It is this folded three-dimensional form that gives a polypeptide its specific properties such as binding, enzymatic activity, transporter function, etc.

The particular folded shape of a polypeptide is determined by the sequence and chirality of the amino acids in the polypeptide chain. It has been shown experimentally that a polypeptide chain of opposite chirality i.e. one made up of D-amino acids [inverted stereochemistry at all chiral centers including the side chain Cβ atoms of Thr and Ile], will fold to form a polypeptide molecule with a shape that is the mirror image of the polypeptide molecule formed by folding the corresponding L-polypeptide chain. Furthermore, such a "D- polypeptide" will have reciprocal chiral ligand-binding properties compared with the corresponding L- polypeptide, i.e. from a mixture of enantiomers, the L- polypeptide will bind one enantiomer of a compound, while the D- polypeptide will bind the other enantiomer of the same compound.

These reciprocal binding properties of mirror image properties can be taken advantage of in the discovery of new drug leads i.e. unique chiral small molecules that bind to a particular polypeptide and interfere with its biological function. Thus, a mixture of small molecules, of arbitrary chirality and consisting of only a single enantiomer of each molecule, such as a mixture of natural product compounds isolated from microbial, plant, or other natural sources, can be used for screening for binding molecules using the mirror image, i.e. D-form of a membrane polypeptide produced using lipid matrix-assisted chemical ligation and synthesis. Chiral molecules identified as binding molecules by this process will bind only to the D- polypeptide and will not bind the corresponding L- polypeptide. However, if the chiral molecule(s) identified as binding molecules for the D-polypeptide are reproduced (synthesized) as the identical molecule but of opposite chirality i.e. the other enantiomer that was not present in the original compound mixture used for screening, then that newly synthesized enantiomer will not bind the D- polypeptide used for screening, but will bind the corresponding L- polypeptide.

In this way, unique chiral binding molecules for natural polypeptide drug targets can be discovered in libraries of chiral (natural product) molecules. Such binding molecules could not be discovered using the corresponding natural polypeptide of L-configuration.

Lipid matrix-assisted membrane polypeptide chemical ligation according to the method of the invention also can be utilized to gain facile access to integral membrane proteins that are anchored to the lipid bilayer by covalent attachment of hydrophobic moieties such as fatty acids, prenyl groups or glyosylphosphatidylinositol anchors. Although many such polypeptides themselves are soluble, attachment of these hydrophobic moieties may reduce the solubility of these proteins and render them difficult to work with in a cell free environment. Accordingly, performing chemical ligation in the presence of a lipidic phase facilitate synthetic access to the acylated forms of these proteins that are inaccessible by other approaches.

Fatty acid chains, such as myristyl acid, can be site-specifically attached to the N-terminus of a peptide on resin through an amide bond. Prenyl groups and palmitic acid groups can be coupled to specific cysteine residues on resin through thioether linkages. The peptide can then be cleaved off the resin in HF, yielding an unprotected peptide with a covalently attached fatty acid or lipid chain.

The following examples illustrate various aspects of this invention. These examples do not limit the scope of this invention.

| Abbreviations | |
| --- | --- |
| AGRP | Agouti-Related Protein |
| AMCA-X | 6-((7-amino-4-methylcoumrin-3-acetyl)amino)hexanoic acid |
| Boc | tert-butoxycarbonyl |
| CLP | Cubic Lipidic Phase matrix |
| DIEA | diisopropylethyleamine |
| DMF | N, N-dimethylformamide |
| DMSO | dimethylsulfoxide |
| DNP | dinitrophenyl |
| DOPC | Dioleoyl phosphatidyl choline |
| DPC | dodecylphosphocholine |
| EDTA | Ethylene diamine tetraacetic acid, tetrasodium salt |
| ES/MS | electrospray mass spectrometry |
| Fmoc | 9-fluorenylmethoxycarbonyl |
| FRET | Fluorescence Resonance Energy Transfer |
| HBTU | O-(1H-benzotriazol-1-yl)-1,1,3,3-tetramethyl-uronium hexafluorophosphate |
| HEPES | 4-(2-hydroxyethyl)-1-piperazineethanesulfonic acid |
| HF | hydrogen fluoride |
| hIL-8 | Human Interleukin 8 |
| HPLC | High Performance Liquid Chromatography |
| IRK1 | Inward-Rectifying Potassium channel pore |
| KCSA | potassium ion channel pore of *Streptomyces lividans* |
| LUV | Large Unilamellar Vesicles |
| MALDI | matrix assisted laser desorption (mass spectrometry) |
| MBHA | methylbenzhydrylamine |
| MC4 | melanocortin |
| MO | 1-monooleoyl-rac-glycerol (C18:1, {cis}-9) |
| OG | β-octyl glucopyranoside |
| PAM | phenyl(acetamido)methyl, i.e. $OCH_2C_6H_4CH_2CONHCH_2C_6H_4$-(polystyrene) |
| SDS-PAGE | Sodium Dodecyl Sulfate-PolyAcrylamide Gel Electrophoresis |
| TAMRA | carboxytetramethylrhodamine |
| TCEP | triscarboxy ethyl phosphine |
| TFA | trifluoroacetic acid |
| TFE | trifluoroethanol |
| TTHA | triethylenetetraminehexaacetic acid |

EXAMPLES

Example 1

Design and Synthesis of Bacteriorhodopsin Membrane Polypeptide

Bacteriorhodopsin functions as a light-driven proton pump in the purple membrane of halobacteria and has a characteristic seven helical structural motif. It is part of a family of retinal-binding proteins that includes the mammalian vision receptor, rhodopsin. Bacteriorhodopsin can be refolded from a fully denatured state into a functional, native protein, and its atomic structure is known. Segments of bacteriorhodopsin can also be designed which independently form a membrane bilayer spanning α-helix when incorporated into a lipid membrane (Hunt, et al., *Biophysical Journal* (1991) 59:400a).

A membrane polypeptide derived from the first transmembrane α-helix of bacteriorhodopsin and its first extracellular loop (corresponding to bacteriorhodopsin residues 5–42) is selected for native chemical ligation. The membrane polypeptide is modified so that the N-terminal Thr residue (corresponding to Thr5 of bacteriorhodopsin) is replaced with a Cys residue to serve as ligation site for native chemical ligation (Dawson, et al., *Science* (1994) 266:776–779).

This Cys residue is capped with an N-terminal Factor Xa protease cleavage site and a few random residues to test for the ability to obtain a free N-terminal cysteine residue by protease cleavage. To ease peptide purification and detection for MALDI-analysis, an imino-biotin label is attached to the C-terminal Lys residue (corresponding to Lys41 of bacteriorhodopsin). Unless otherwise stated, all amino acid sequences are provided in the N-terminal to C-terminal direction.

Bacteriorhodopsin membrane polypeptide 1: Native bacteriorhodopsin α-helix 1 and first extracellular loop (SEQ ID NO:1): TGRPEWIWLA LGTALMGLGT LYFLVKGMGV SDPDAKK. Bacteriorhodopsin membrane polypeptide 2: Cys-modified bacteriorhodopsin α-helix 1 and first extracellular loop (SEQ ID NO:2): CGRPEWIWLA LGTALMGLGT LYFLVKGMGV SDPDAKK. Bacteriorhodopsin membrane polypeptide 3: Factor Xa protease cleavage site, Cys-modified bacteriorhodopsin α-helix 1 and first extracellular loop (SEQ ID NO:3): GKGYIEGRCG RPEWIWLALG TALMGLGTLY FLVKGMGVSD PDAKK Bacteriorhodopsin membrane polypeptide 3 (SEQ ID NO:3) is synthesized on an MBHA resin using a in situ neutralization protocol for Boc chemistry using established side-chain protection strategies except that the ε-amino group of the C-terminal Lys is protected with an Fmoc group (Schnolzer, et al., *Int. J. Pept. Protein Res.* (1992) 40:180–193). Machine-assisted peptide synthesis is performed on a custom-modified Applied Biosystems 430A peptide synthesizer following established protocols (Schnolzer, et al., supra). The Fmoc protecting group of the C-terminal Lys is removed after peptide synthesis by incubation with 20% piperidine in DMF and an N-imino biotin group is attached to the free amino group by addition of 2-imino N-hydroxysuccinimide (Sigma, St. Louis). The peptide is deprotected and simultaneously cleaved from the resin by treatment with HF in the presence of 10% v/v p-cresol for 1 hour at 0° C. The crude peptide is precipitated in diethyl ether, taken up in 75% B (acetonitrile+0.1% TFA) and lyophilized. Polypeptide 3 (SEQ ID NO:3) is purified by preparative reversed-phase HPLC (45–75% B over 60 minutes at 10 ml/min) and characterized by electrospray MS (obs. MW 5080±1 kD, calc. 5080 kD (average isotope composition)). Gradient HPLC is performed on a Rainin dual-pump high-pressure mixing system with 214 nm UV detection using a Vydac C-4 semipreparative column (10 μm particle size, 1 cm×25 cm) or a Vydac C-4 preparative column (10 μm particle size, 2.2 cm×25 cm). Electrospray mass spectra is obtained using a Sciex API-1 quadrupole ion-spray mass spectrometer. MALDI mass spectra is obtained using a ciphergen xyz TOF-MALDI instrument.

Example 2

Design and Synthesis of Ligation Label

A C-terminal thioester-modified ligation label peptide EAQL (SEQ ID NO:4) designed for native chemical ligation to the lipid matrix-incorporated membrane polypeptide (SEQ ID NO:2) is synthesized manually on a PAM-thioester generating resin, cleaved and deprotected as described above. The crude peptide is precipitated in diethyl ether, taken up in 50% B and lyophilized. The peptide is purified by semi preparative reversed-phase HPLC (25–45% B over 45 minutes at 10 ml/min) and characterized by electrospray MS (obs. MW 647±1 kD, calc. 647 (average isotope composition)).

Example 3

Preparation of CLP Matrix and Incorporation of Bacteriorhodopsin Membrane Polypeptide Cubic lipidic phase matrices admixed with membrane polypeptide 3 (SEQ ID NO:3) are prepared following standard protocols by centrifugation of the lipid matrix constituents in a Haraeus Biofuge 13 table-top centrifuge. In particular, 75 μg of membrane polypeptide 3 (SEQ ID NO:3) is dissolved in 3 μl 200 mM Tris buffer containing 2% OG at pH 8. These polypeptide solutions are added to a 1.7 ml eppendorf tube containing 14.2 mg MO. Subsequently, 1.5 μl 200 mM Tris buffer (pH 8) is added to decrease the lipid:water ratio. The mixture is spun for 3 hours at 12,000 rpm at approximately 25° C. Formation of CLP's is indicated by the formation of optically clear, gel-like phases. These phases remain optically clear at room temperature for at least two months. Off-resonance Raman spectra excited at 514.5 nm is used to demonstrate that the addition of the membrane polypeptide does not perturb the membrane bilayer structure of the CLP, as indicated by an unaltered intensity ratio of the C—H stretching modes at 2885 and 2845 $cm^{-1}$ in the absence and presence of membrane polypeptide in the CLP (Razumas, et al., *Chemistry and Physics of Lipids* (1996) 84:123–138).

Example 4

Affinity Purification of CLP Matrix-Incorporated Bacteriorhodopsin Membrane Polypeptide and MALDI-TOF Analysis CLPs (MO) containing bacteriorhodopsin membrane polypeptide 3 (SEQ ID NO:3) are solubilized by adding 33 mg of OG in 100 μl of water. To prevent unwanted ligation during analysis, 20% β-mercaptoethanol is added during solubilization. The pH of the solubilized phase is adjusted to 9.5 using 0.2 M NaOH. Streptavidin-coated magnetic beads (Sigma, S 2415) are added to the solubilized phases and incubated at room temperature for 1 hour. The magnetic beads are washed 5 times with 20 mM Bis-Tris Propane buffer, pH 9.5, isolated by magnetic separation after each wash. The magnetic beads are resuspended in a saturated solution of α-cyano-4-hydroxy-cinnamic acid in 50% acetonitrile/0.1% TFA. A 1 mL aliquot of the magnetic beads/matrix suspension is deposited directly on the sample slide and allowed to air dry. The sample preparations are analyzed using a Ciphergen Biosystems Massphoresis System time-of-flight mass spectrometer. All spectra are internally calibrated using peptide standards and represent an average of 25 shots.

Example 5

Protease Cleavage of CLP Matrix-Incorporated Bacteriorhodopsin Membrane Polypeptide Protease cleavage of the CLP matrix-incorporated bacteriorhodopsin membrane polypeptide 3 (SEQ ID NO:3) is preformed by adding 1.5μl of a 1 mg/ml solution of Factor Xa (New-England Biolabs) in 50% glycerol and 20 mM HEPES, 50 mM NaCl, 2 mM $CaCl_2$ (pH 8.0) to the CLP. The mixture is thoroughly mixed using a plastic pipette tip and the CLP spun for 15 minutes at 12,000 rpm to obtain formation of an optically clear phase. The extent of cleavage after incubation overnight and generation of CLP incorporated cleavage product is determined by MALDI mass spectrometry as described above.

Example 6

Native Chemical Ligation of CLP Matrix-Incorporated Bacteriorhodopsin Membrane Polypeptide Native chemical ligation of CLP-incorporated polypeptide is performed as follows. Approximately 10 μg of the ligation label peptide EAQL (SEQ ID NO:4) is dissolved in 1 μl of 200 mM Tris buffer (pH 8) and added to the CLP containing the Cys-terminal transmembrane polypeptide (SEQ ID NO:2), followed by addition of 0.5 μl thiophenol and 3 mg MO to maintain an appropriate lipid:water ratio compatible with CLP formation. The mixture is mixed thoroughly using a small pipette tip. The CLP is then spun for 15 minutes at 12,000 rpm to form an optically clear phase. Aliquots of the CLP are removed at specific time intervals to monitor the progress of ligation by MALDI mass spectrometry as described above. The primary chemical ligation reaction product is as follows.

Bacteriorhodopsin membrane polypeptide 5: Chemical ligation labeled, Cys-modified bacteriorhodopsin α-helix 1 and first extracellular loop (SEQ ID NO:5): EAQL-CGRPEW IWLALGTALM GLGTLYFLVK GMGVSDP-DAK K.

Figure 3:
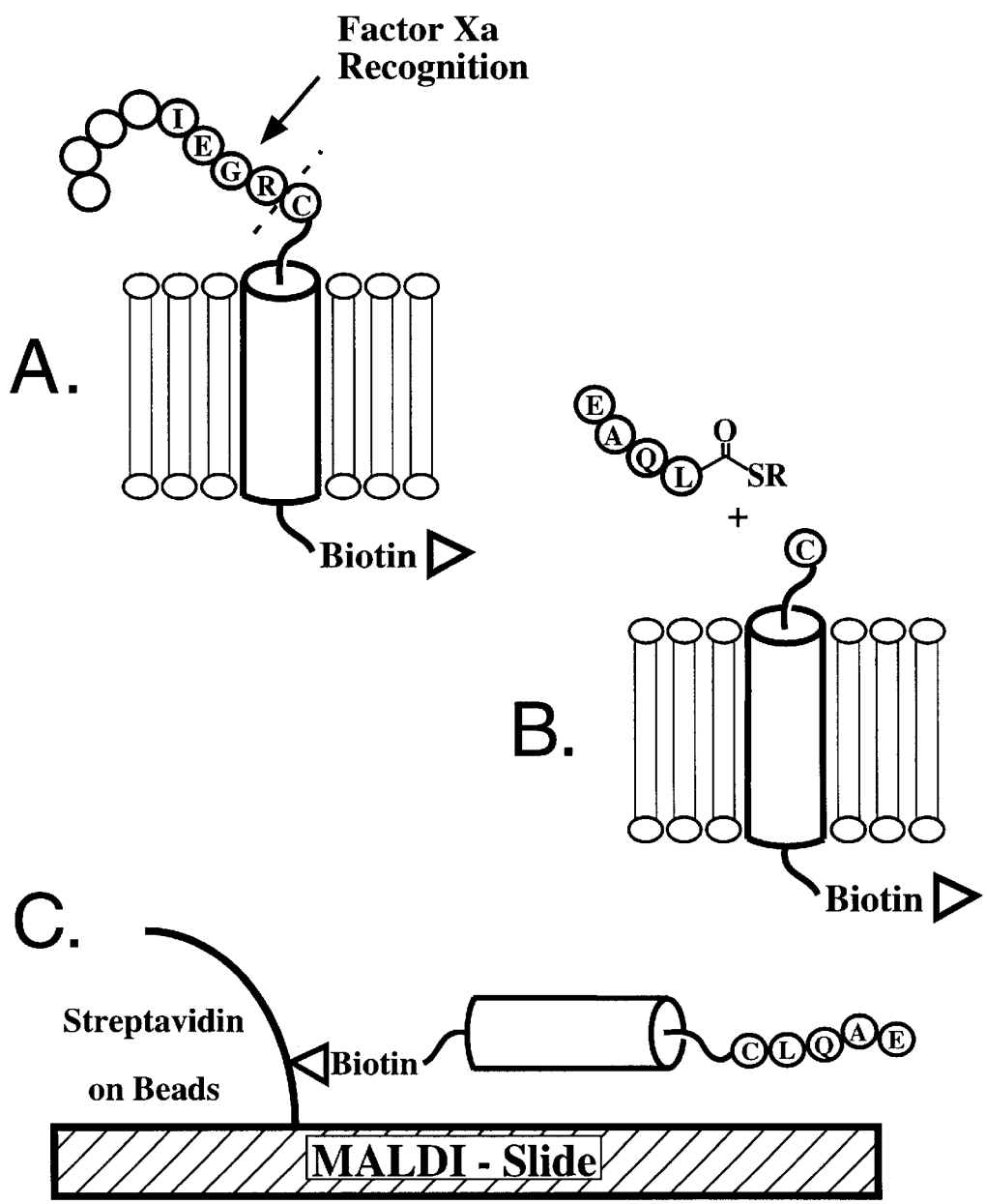
FIGS. 3 A–C shows schematic demonstrating site-specific protease cleavage and native chemical ligation of a lipid matrix-embedded membrane polypeptide.

FIG. 3 provides a schematic illustrating protease cleavage and use of native chemical ligation to generate a labeled CLP matrix-embedded membrane polypeptide. After incorporation into the CLP lipid bilayer, the N-terminal polypeptide containing the protease recognition site is removed by Factor Xa cleavage (A). A ligation peptide corresponding to the N-terminus of bacteriorhodopsin (Ile4 is replaced with Leu4 to optimize ligation) is then ligated to the transmembrane polypeptide to obtain the full bacteriorhodopsin N-terminus (B). The extent of cleavage and the progress of the ligation inside the CLP is measured by obtaining MALDI mass spectra of the transmembrane polypeptide adsorbed to magnetic beads through a N-iminobiotin label (C).

Figure 4:
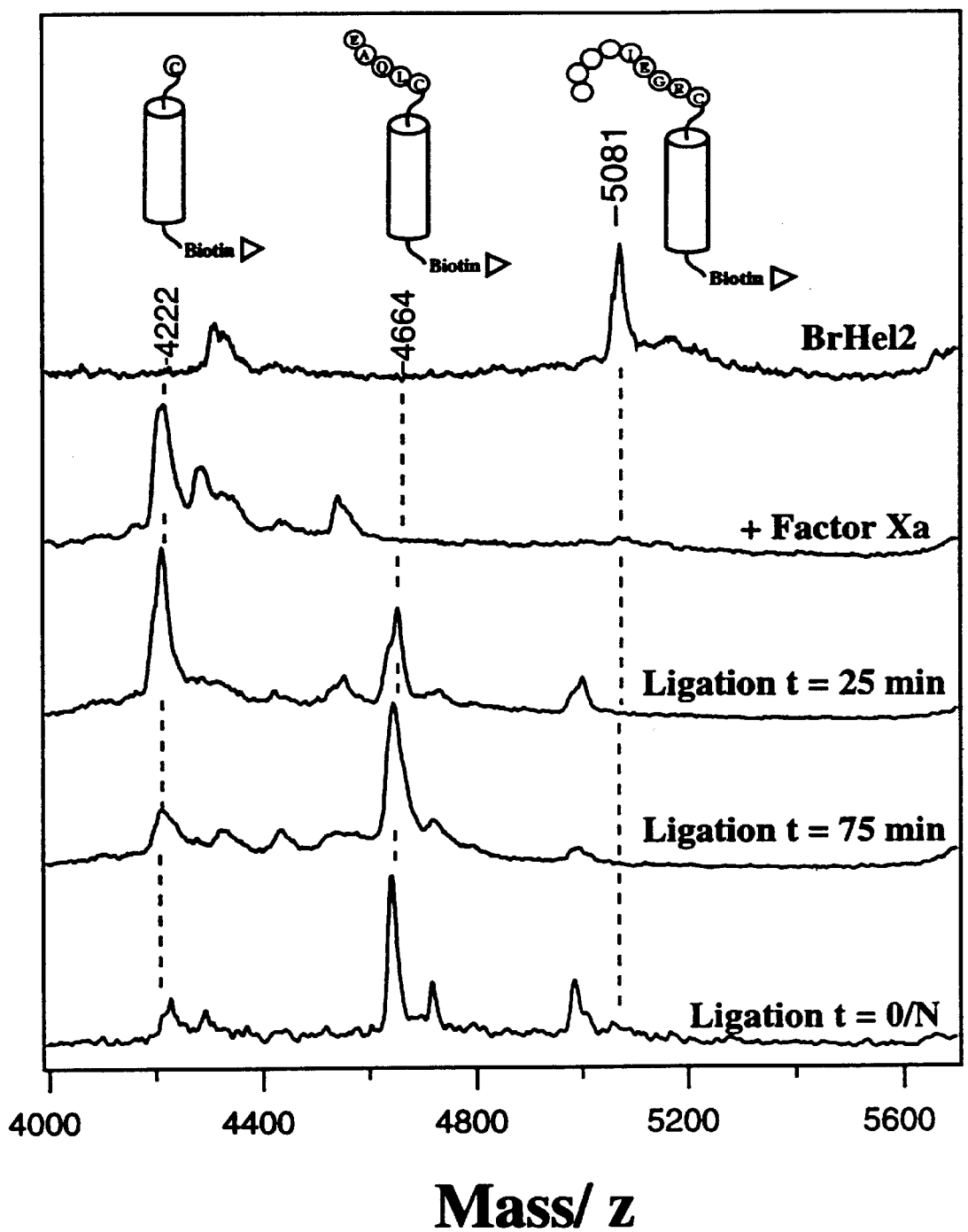
FIG. 4 shows a typical matrix assisted laser desorption (MALDI) mass spectra output that monitors creation of a free unprotected N-terminal cysteine residue by site-specific cleavage, followed by native chemical ligation of a ligation label of choice to this residue.
Figure 5:
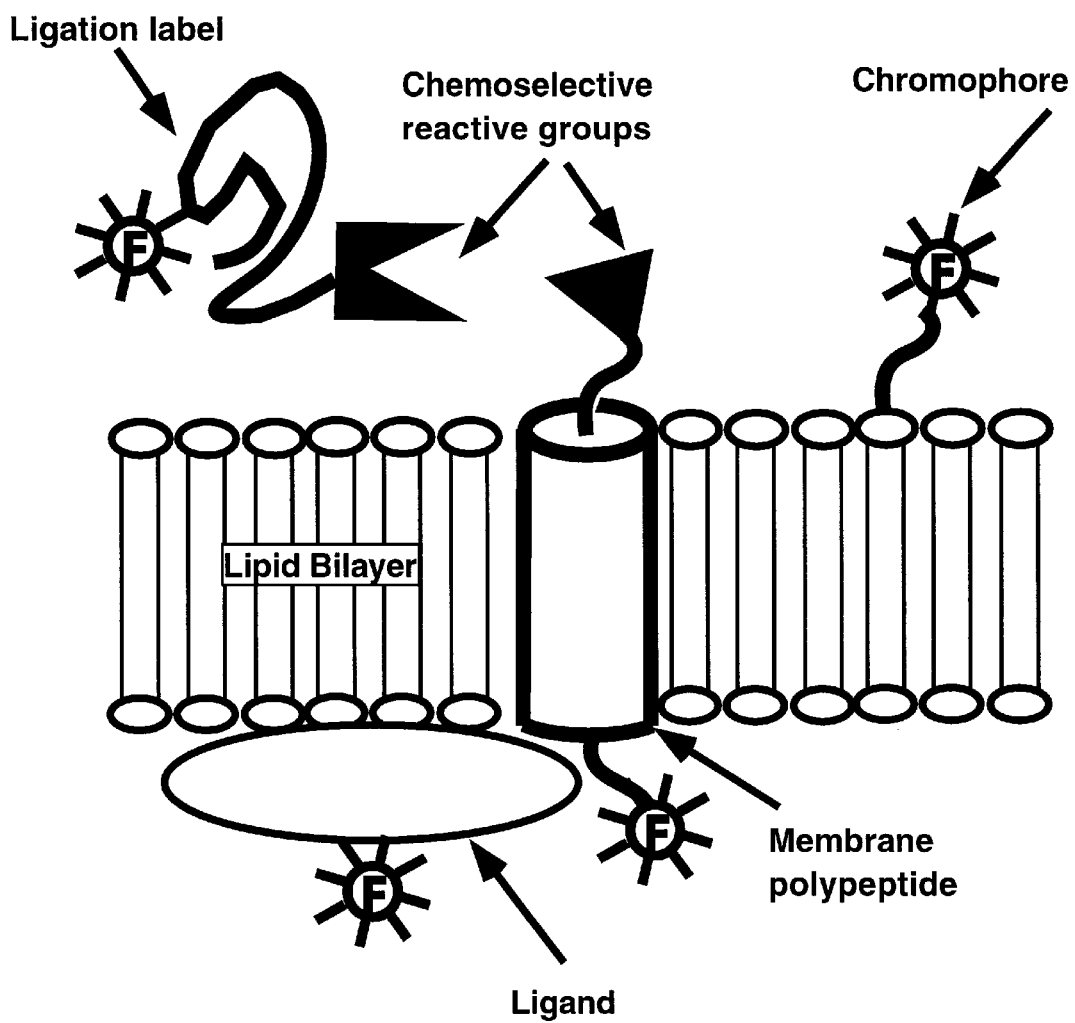
FIG. 5 illustrates donor-acceptor chromophore pair labeling schemes for resonance energy transfer (FRET) assays of a lipid-matrix embedded membrane polypeptide.
Figure 6:
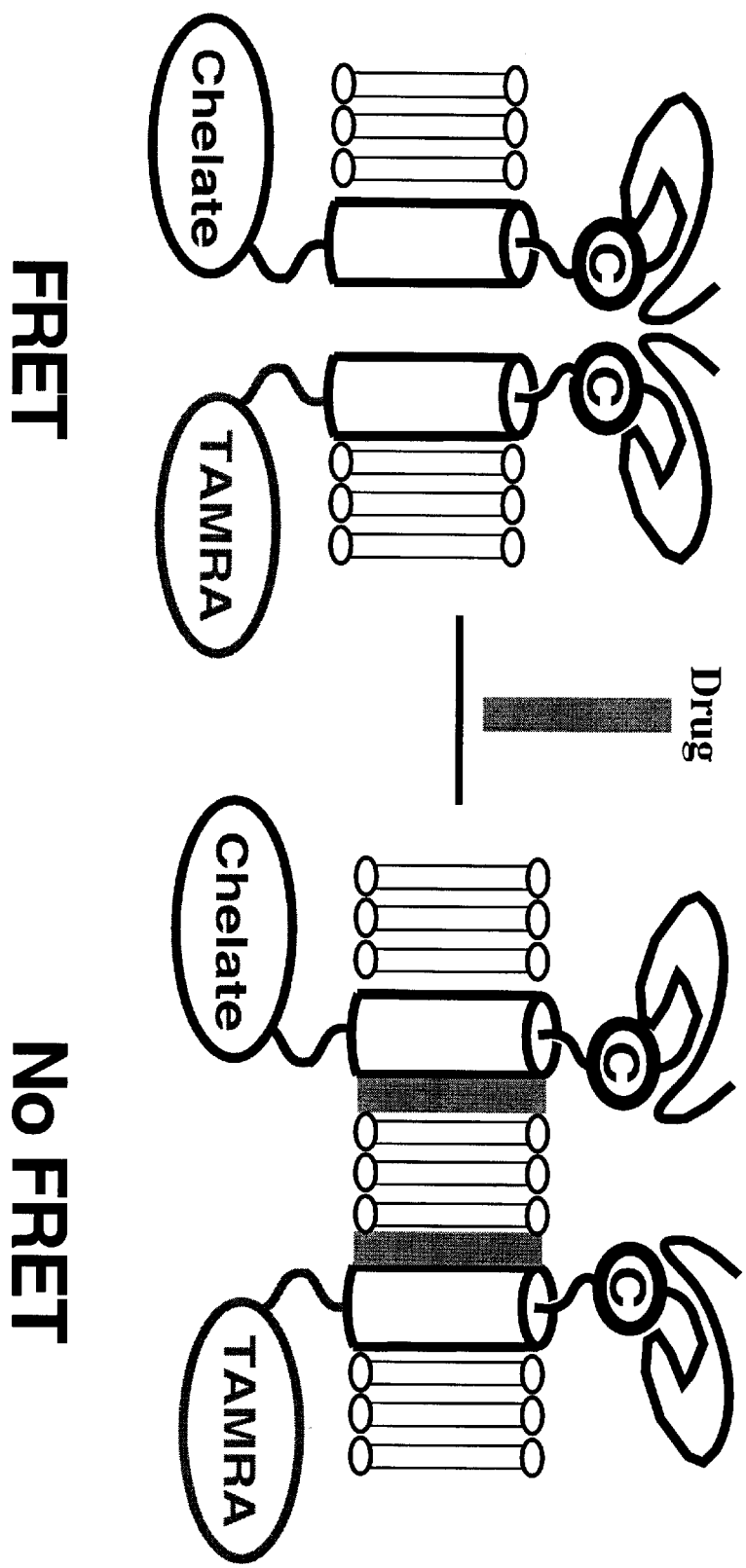
FIG. 6 illustrates FRET assays for ion channels.
Figure 7:
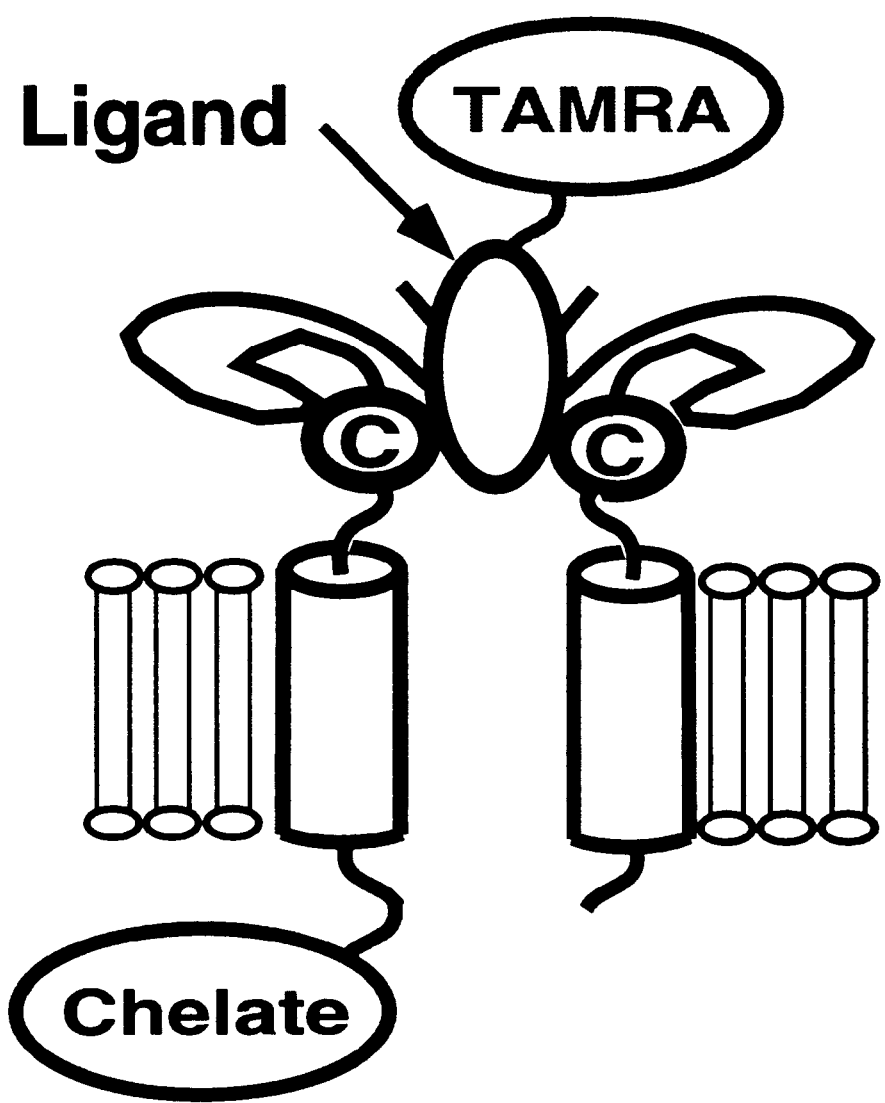
FIG. 7 illustrates FRET proximity assays for ion channels.
Figure 8:
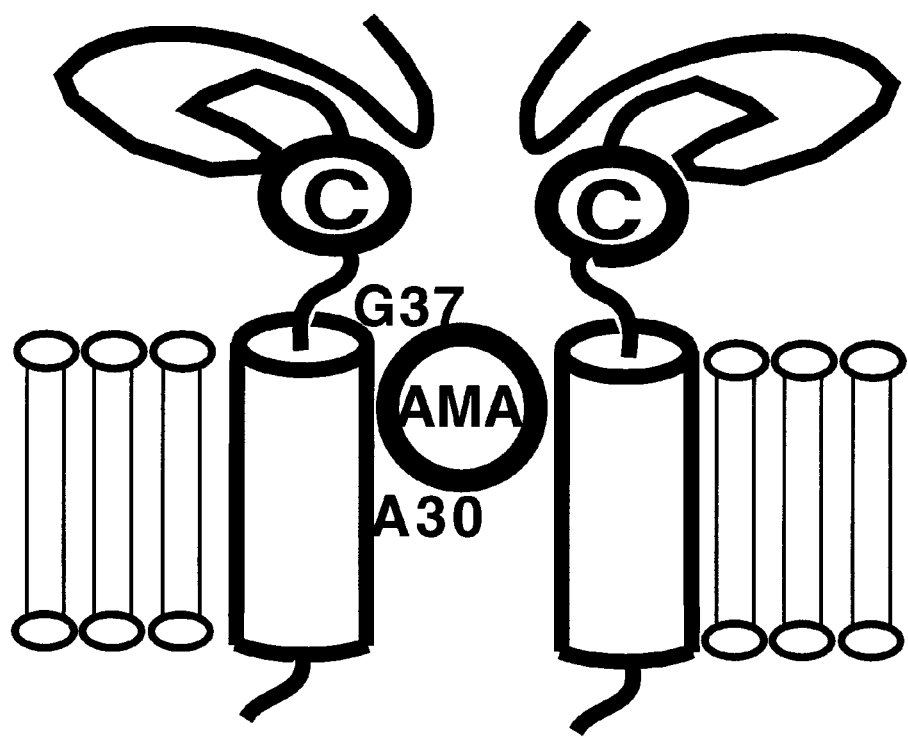
FIG. 8 illustrates structure-activity relationship (SAR) assays by NMR for ion channels.

FIG. 4 shows a typical MALDI mass spectra output that monitors creation of a free unprotected N-terminal cysteine by protease cleavage, followed by the chemical ligation of a ligation peptide of choice to this residue. Spectrum A presents a MALDI spectrum of polypeptide 3 (SEQ ID NO:3) after incorporation into a CLP, followed by dissolution of the CLP in OG/20% β-mercaptoethanol. The spectrum displays one major peak at m/z=5080, corresponding to the mass of the uncleaved polypeptide 3 (SEQ ID NO:3). Smaller peaks represent impurities from the affinity beads, and also are present in spectra in the absence of protein (data not shown). Spectrum B presents a mass spectrum of the same polypeptide after cleavage with Factor Xa overnight. The disappearance of the major peak at m/z=5080 concomitant with the appearance of a major peak at m/z=4220 is consistent with almost complete removal of the Cys-capping sequence GKGYIEGR by the Factor Xa protease and generation of polypeptide 2 (SEQ ID NO:2).

Spectra C, D and E monitor the appearance of ligation product after addition of a 2-fold excess of ligation peptide 4 (SEQ ID NO:4) with 5% thiophenol to the Cys-terminal membrane polypeptide 2 (SEQ ID NO:2) after 25 and 75 minutes and overnight incubation, respectively. The gradual disappearance of the peak at m/z=4220 with a concomitant increase of a peak at m/z=4661 demonstrates the progress of the formation of a native amide bond between the α-helical transmembrane polypeptide 2 (SEQ ID NO:2) and ligation peptide 4 (SEQ ID NO:4). As judged from the MALDI mass spectrum, the conversion from the Cys-capped transmembrane polypeptide to the fully ligated transmembrane polypeptide (SEQ ID NO:5) is completed to greater than 90%.

Example 6

Reverse Phase HPLC Purification of Membrane Polypeptide Incorporated in Cubic Lipidic Phase Membrane polypeptide chemical ligation is performed with membrane polypeptide 1 (SEQ ID NO:1) and membrane polypeptide 4 (SEQ ID NO:4) as described above to yield CLP-incorporated membrane polypeptide 5 (SEQ ID NO:5). After ligation is complete, the entire CLP is dissolved in 50 μl 85% aqueous isopropanol containing 50 mM formic acid. The solution is then diluted with an equal volume of 50 mM aqueous formic acid.

A C1 8 reverse-phase HPLC column is equilibrated at 45% (6:3:1/ isopropanol/acetonitrile/water including 0.1% TFA). 20 μl of dissolved CLP are injected into the column and eluted isocratically at 45% isopropanol/acetonitrile/water including 0.1 TFA. The ligated membrane polypeptide 5 (SEQ ID NO:5) is eluted after 10 minutes isocratic elution and is positively identified by ES/MS. MO is eluted isocratically between 16 and 20 minutes. Membrane polypeptide 5 (SEQ ID NO:5) is isolated by lyophilization.

Example 7

Location of Bacteriorhodopsin Membrane Polypeptide in CLP Matrix

The channels inside a CLP are filled with aqueous buffer, whereas at a lipid:detergent ratio of 300:1, excess detergent is absorbed into the lipid bilayer phase. Additionally, complete ligation also is observed in the absence of detergent (data not shown). Peptide 1 is extremely hydrophobic peptide and does not dissolve in 6M guanidinium HCl/200 mM phosphate (pH 7.5). It is therefore unlikely for significant amounts of this peptide to be dissolved in the aqueous channel. Furthermore, no visible aggregation of hydrophobic peptide is observed after prolonged spinning of the CLP's at 12,000 rpm after incorporation of 1 mg of peptide into a CLP of the same size. Taken together with the previous observation by CD FTIR spectroscopies and proteolysis protection experiments that peptide 1 folds independently to an α-helical transmembrane peptide inside liposomes, (Hunt, et al., *Biophysical Journal* (1991) 59:400a), it is reasonable to interpret that the cleavage and ligation of peptide 1 is performed on a peptide incorporated into the membrane bilayer.

The above Examples collectively indicate that cleavage of transmembrane peptide 3 (SEQ ID NO:3) and ligation of transmembrane peptide 2 (SEQ ID NO:2) and peptide 4 (SEQ ID NO:4) is indeed performed on a polypeptide that is incorporated into the membrane bilayer to form a lipid-matrix in which transmembrane peptide 5 (SEQ ID NO:5) is properly and functionally embedded.

Example 8

Chromophore Labeling and FRET Analyses of Bacteriorhodopsin Membrane Polypeptide in CLP Matrix A chromophore labeled CLP matrix-embedded bacteriorhodopsin membrane polypeptide is constructed and analyzed by FRET by first labeling bacteriorhodopsin membrane polypeptide 1 (SEQ ID NO:1) with TTHA coumarin and labeling the thioester ligation label, peptide 4 (SEQ ID NO:4) with TEXAS RED.

Membrane polypeptide 1 (SEQ ID NO:1) and ligation label peptide 4 (SEQ ID NO:4) are synthesized on a PAM thioester generating resin and carboxy-generating resin, respectively using an in situ neutralization protocol for Boc chemistry using established side-chain protection strategies. The transmembrane bacteriorhodopsin with a coumarin-lanthanide complex as follows.

Prior to the actual labeling step, the TTHA-TFA salt reagent is prepared; 100 mg TTHA is dissolved in 50 ml neat TFA for 4 hours at room temperature. The solution is dried on a Rotavap, taken up in 50% aqueous acetonitrile and lyophilized to yield a white powder that very readily dissolves in DMF.

Labeling of free amino groups on-resin: For coupling to the polypeptide N-terminus, N-terminally Boc protected peptide resin is equilibrated in DMF. The terminal Boc group is removed by treatment with TFA (2×1 minute) and then washed with DMF, 10% DIEA in DMF and DMF. For coupling to a lysine residue, ε-Fmoc protected Boc-lysine is incorporated into the target polypeptide chain during chain assembly. The Fmoc-group is removed either by treatment with 20% piperdine in DMF (2×5 minutes) or by treatment with a two-fold excess of DBU (1,8-dioazabicyclo[5.4.0] undec-7-ene) for one minute for the target polypeptide on thioester-generating resin. The polypeptide is then washed with DMF.

ACMA-X-Chelating complex fluorescent probes: The N-terminally Boc protected peptide resin is equilibrated in DMF. The Fmoc protecting group of Lysine 36 in membrane polypeptide 1 (SEQ ID NO:1) is removed by treatment with 20% piperidine in DMF for 10 minutes. Then, 10 mg of AMCA-X (~2×excess) is dissolved in 150 µl DMSO and added to 0.01 mmol drained peptide resin for 1 hours. Unreacted AMCA-X is washed away with DMSO and DMF. Ninhydrin tests before and after the coupling reaction demonstrated>95% reaction efficiency. Approximately 0.03 mmol TTHA-TFA salt was dissolved in an equimolar amount of 0.5 M HBTU solution in DMF containing ~20% DIEA and coupled to the peptide resin overnight. The resin is washed with DMF and dichloromethane and dried. HF-resin cleavage and peptide purification are performed following standard procedures (Schnoelzer, 1992, supra). For complexation with the lanthanide ions ($Eu^{3+}$, $Tb^{3+}$, or $Sm^{3+}$) the peptide is dissolved in 50% acetonitrile containing a 3-fold excess aqueous lanthanide chloride. Metal incorporation is monitored by ES/MS analysis. Absorbance spectra of the complexed peptide showed an absorption maximum at 329 nm.

TEXAS RED fluorescent probe: The N-terminally Boc protected polypeptide (SEQ ID NO:4) resin is equilibrated in DMF and the Boc group removed by treatment with TFA two times for 1 minute. The N-terminus is then neutralized by treatment with 10% DIEA for 2×1 minute. 25 mg of TEXAS RED (~2×excess) is dissolved in 150 µl DMSO and added to 0.02 mmol drained peptide resin for 1 hour. Unreacted dye is washed away with DMSO and DMF. Ninhydrin tests before and after the coupling reaction demonstrated>95% reaction efficiency. HF-resin cleavage and peptide purification are performed following standard procedures. (Schnoelzer, 1992, supra).

Both polypeptides (SEQ ID NO: 1 and SEQ ID NO:4) are added to the CLP matrix as described in Example 4 along with an aqueous buffer solution containing three-fold excess of chelating metal ($Eu^{3+}$, $Tb^{3+}$, or $Sm^{3+}$) and 1% thiophenol. After ligation, the lipid matrix containing the ligated membrane polypeptide is transferred into a small cuvette and equilibrated to obtain an optically isotropic CLP matrix gel. Fluorescence energy transfer experiments are performed in a fluorolog 3 spectrofluorometer exciting with a pulsed Xe flash lamp at 330 nm and detecting after a 50 microsecond gate between 500 and 750 nm. FRET distances are analyzed by comparison to the known distance between the labeling sites in the bacteriorhodopsin crystal structure.

Example 9

Chemical Ligation of Liposome-Incorporated Bacteriorhodopsin Membrane Polypeptide For preparation of lipid vesicles, egg-lecithin is dissolved in 2:1 chloroform/methanol, evaporated to form a dry film in a round-bottom flask and further dried under vacuum in a lyophilizer. The lipid is suspended in aqueous buffer (5 mM HEPES, 0.2 mM EDTA, pH 7.2) by vortexing for 30 s to form multilamellar liposome vesicles. LUV's are prepared from phospholipids after 10 freeze/thaw cycles by extrusion through polycarbonate membranes three times with 0.4 µm pore diameter and then ten times with 0.1 µm pore diameter. The solution is spun at 500×g to pellet lipid aggregates and the liposomes are then pelleted at 48,000×g.

Bacteriorhodopsin membrane polypeptide 3 (SEQ ID NO:3) is dissolved in a minimum amount of neat TFE and added to a suspension of egg-lecithin liposome vesicles in aqueous buffer (5 mM HEPES, 0.2 mM EDTA, pH 7.2) at a lipid:protein ratio of 1000:1. Incorporation of membrane polypeptide into liposome lipid membrane is observed by monitoring fluorescence emission of tryptophan above 300 nm. The proteoliposomes are pelleted at 48,000 g and frozen in aliquots at −80° C.

For chemical ligation of the lipid-embedded polypeptide, an aliquot of proteoliposomes is suspended in 5 mM HEPES, 0.2 mM EDTA, pH 7.2 and treated with 1/100th molar equivalent of Factor Xa protease and ligated as described in Examples 3 and 5–6 and ligation monitored as in Example 4.

Example 10

Chemical Ligation of Micelle-Incorporated Bacteriorhodopsin Membrane Polypeptide 300 μg of membrane polypeptide 2 (SEQ ID NO:2) and 50 μg C-terminal α-thioester modified ligation polypeptide 4 (SEQ ID NO:4) are dissolved in 100 μl 100 mM phosphate buffer (pH 7.5) containing 10% Ammonyx-LO (N,N-dimethyl amineoxide) and 1 μl thiophenol. The solution is stirred for 24 hours at room temperature in an eppendorf tube. The progress of the ligation is monitored by analytical reverse-phase HPLC. Ligated membrane polypeptide is isolated using semi-preparative reverse-phase HPLC and the identity of ligated product (membrane polypeptide 5 (SEQ ID NO:5)) is confirmed by mass analysis employing lectrospray mass spectrometry.

Example 11

Chemical Ligation of Cell Membrane-Incorporated Melanocortin Receptor MC4

Membrane polypeptide chemical ligation of recombinantly produced melanocortin receptor MC4, embedded in native lipid membrane patches isolated from cells, is performed as follows. HEK-293 cells overexpressing MC4 receptor containing an engineered Factor Xa cleavage site (SEQ ID NO:6) are constructed as follows, where the MC4 Receptor Membrane Polypeptide w/Factor Xa Cleavage Site (SEQ ID NO:6) has the following amino acid sequence:

MVNSTHRGMH TSLHLWNRSS YRLHSNASES

LGKGYIEGRC YEQLFVSPEV FVTLGVISLL ENILVIVAIA

KNKNLHSPMY FFICSLAVAD MLVSVSNGSE TIIITLLNST

DTDAQSFTVN IDNVIDSVIC SSLLASICSL LSIAVDRYFT

IFYALQYHNI MTVKRVGIII SCIWAACTVS GILFIIYSDS

SAVIICLITM FFTMLALMAS LYVHMFLMAR LHIKRIAVLP

GTGAIRQGAN MKGAITLTIL IGVFVVCWAP FFLHLIFYIS

CPQNPYCVCF MSHFNLYLIL IMCNSIIDPL IYALRSQELR

KTFKEIICCY PLGGLCDLSS RY

The MC4 membrane polypeptide (SEQ ID NO:6) is designed for chemical ligation following Factor Xa cleavage to a C-terminal α-thioester modified MC4 Receptor Ligation Label (SEQ ID NO:7) having the following amino acid sequence:

MVNSTHRG MHTSLHLW NRSSYRLH

SNASESLG KGYSDGG

The ligation label optionally is modified to contain other modifications, such as the insertion of non-natural amino acids, isotopically labeled amino acids, or fluorescent probes attached at specific sites. For example, N-terminus of the ligation label is modified by coupling a TEXAS RED in DMSO as described in Example 8.

Eukaryotic HEK-293 cells overexpressing the MC4 receptor (SEQ ID NO:6) are constructed as follows. The coding region of the gene for the MC4 receptor is subcloned into bacteriophage M13 for performing single stranded site-directed mutagenesis (Sambrook, et al., supra). Oligonucleotide-directed mutagenesis (Kunkel, 1984; Zoller & Smith, 1987), in vitro mutagenesis kit Muta-Gene T4® (BioRad; Hercules, Calif.), is utilized to generated the Factor Xa site (bacteriophage M13 vector containing the mutant receptor gene, pGRFN-MC4-8a). Presence of the Factor X cleavage site is confirmed by a single-stranded DNA sequencing (Sequenase Version 2.0 (Life Science; Cleveland, Ohio)). DNA encoding mutant MC4 receptors are subcloned into eukaryotic expression vector pcDNA3.1 (Invitrogen, Carlsbad, Calif.) to create the MC4 receptor expression construct pGRFN-MC4-8b. This construct is transfected into HEK-293 cells (ATCC, Manassas, Va.) following standard protocols (LipfectAmine Reagent® (Life Technologies; Gaithersburg, Md.)) to obtain cell line cGRFN-MC4-8a.

Membrane patches are isolated from cGRFN-MC4-8a cells expressing MC4 receptor membrane polypeptide (SEQ ID NO:6). Cells containing approximately $10^7$ receptors per cell recovered from 10 cm culture plate are washed five times with PBS (PBS: 1.12 M NaCl, 2.6 mM KCl, 8.1 mM $Na_2HPO_4$, pH 7.4), and incubated in hypotonic buffer (1 mM Tris-HCl, pH 6.8, 10 mM EDTA). Cells are disrupted by shearing them in a syringe three times through a 26-gauge needle. Disrupted cells are loaded onto a step-density gradient and spun at 20,000×g for 10 minutes. The gradient interface containing the membrane patches is taken up with a Pasteur pipette. The membrane patches are sedimented at 48,000×g for 10 minutes and washed three times followed by sedimentation. All procedures are performed at 4° C. unless stated otherwise.

For cleavage of MC4 membrane polypeptide (SEQ ID NO:6) with Factor Xa and native chemical ligation to the MC4 receptor ligation label (SEQ ID NO:7), membrane patches containing recombinant MC4 receptor (SEQ ID NO:6) are suspended in 50 μl of 100 mM Tris/pH 8 containing protease inhibitors that are not targeting Factor Xa protease such as aprotinin, 2 mg/mL, N-[N-(L-3-Transcarboxirane-2-carbonyl)-L-leucyl]-agmatine, 10 μg/mL, and pepstatin A, 2 mg/mL. 2 μl Factor Xa solution (1.0 mg/ml) is added and the suspension incubated overnight at room temperature (~25° C.). The membrane patches are sedimented at 48,000×g and washed three times with 100 mM phosphate buffer (pH 7.5). Cleavage of MC4 (SEQ ID NO:6) with Factor Xa yields the MC4 Receptor Membrane Polypeptide Factor Xa Cleavage Product (SEQ ID NO:8):

CYEQLFVSPE VFVTLGVISL LENILVIVAI AKNKNLHSPM

YFFICSLAVA DMLVSVSNGS ETIIITLLNS TDTDAQSFTV

NIDNVIDSVI CSSLLASICS LLSIAVDRYF TIFYALQYHN

IMTVKRVGII ISCIWAACTV SGILFIIYSD SSAVIICLIT

MFFTMLALMA SLYVHMFLMA RLHIKRIAVL

PGTGAIRQGA NMKGAITLTI LIGVFVVCWA PFFLHLIFYI

SCPQNPYCVC FMSHFNLYLI LIMCNSIIDP LIYALRSQEL

RKTFKEIICC YPLGGLCDLS SRY

Chemical ligation of cleaved MC4 (SEQ ID NO:8) in membrane patches to a MC4 ligation label (SEQ ID NO:7) with or without AMCA-X/TTHA/$Eu^{3+}$ is performed as follows. A 2 mM solution of MC4 ligation label (SEQ ID NO:7) containing a C-terminal thioester is added in 1.5 M guanidinium chloride/100 mM sodium phosphate (pH 7.5) containing 1% thiophenol and incubated overnight. Fluorescence labeled or native MC4 ligation label (SEQ ID NO:7) containing a C-terminal thioester is then added in 1.5 M guanidinium chloride/100 mM phosphate (pH 7.5) containing 1% thiophenol. Labeling with AMCA-X/TTHA/ $Eu^{3+}$ chelate is performed as described in Example 8, with the following modifications. After overnight incubation, the modified MC4 receptor-containing membranes are washed with PBS and aliquots are frozen at −80° C. The ligation product has the following amino acid sequence (SEQ ID NO:9) corresponding to the semi-synthetic lipid matrix-embedded MC4 receptor, with or without the site specific fluorescence label:

MC4 Receptor membrane polypeptide-ligation label ligate (SEQ ID NO:9):

MVNSTHRGMH TSLHLWNRSS YRLHSNASES

LGKGYSDGGC YEQLFVSPEV FVTLGVISLL ENILVIVAIA

KNKNLHSPMY FFICSLAVAD MLVSVSNGSE TIIITLLNST

DTDAQSFTVN IDNVIDSVIC SSLLASICSL LSIAVDRYFT

IFYALQYHNI MTVKRVGIII SCIWAACTVS GILFIIYSDS

SAVIICLITM FFTMLALMAS LYVHMFLMAR LHIKRIAVLP

GTGAIRQGAN MKGAITLTIL IGVFVVCWAP FFLHLIFYIS

CPQNPYCVCF MSHFNLYLIL IMCNSIIDPL IYALRSQELR

KTFKEIICCY PLGGLCDLSS RY

Membrane patches containing chemically ligated MC4 receptor (SEQ ID NO:9) are dissolved in 10% SDS-PAGE loading buffer and loaded onto a 10% SDS-PAGE gel are identified by Western blotting. Alternatively, the fluorescent probe-labeled MC4 receptor is visualized directly on the gel.

Example 12

FRET Analysis of Chromophore-Labeled Melanocortin Receptor MC4

FRET analysis of cs124/ TTHA/$Tb^{+3}$ or AMCA-X/ TTHA/$Eu^{3+}$ chelate-labeled MC4 receptor is performed as follows. Membrane patches containing receptors carrying cs124/TTHA/$Tb^{+3}$ or AMCA-X/TTHA/$Eu^{3+}$ chelate are constructed as in Example 11 and are suspended in PBS in a 200 μl cuvette. MC4 receptor ligand AGRP is labeled with TAMRA (paired with $Th^{+3}$ chelate) or TEXAS RED (paired with $Eu^{+3}$ chelate) following the procedure described in Example 11. The human AGRP sequence (SEQ ID NO:10) is:

MLTAAVLSCAL LLALPATRGAQ MGLAPMEGIRR

PDQALLPELPG LGLRAPLKKTT AEQAEEDLLQE

AQALAEVLDLQ DREPRSSRRCV RLHESCLGQQV

PCCDPCATCYC RFFNAFCYCRK LGTAMNPCSRT

TAMRA-labeled or TEXAS RED-labeled AGRP is titrated into the cuvette from a stock solution in PBS and fluorescence spectra are taken in a Fluorolog 3 spectrofluorometer equipped with a Xe flash lamp. Emission is detected after 50 μs for 1 ms between 400 and 700 nm.

To screen for inhibitors of ligand binding, potential inhibitors are added and the change in shape of the fluorescence spectrum is monitored. Alternatively, the decay of the fluorescence emission is monitored at 543 nm for TAMRA or 614 nm for TEXAS RED. Replacement of the quenching natural ligand by the inhibitor increases the fluorescence lifetime at this wavelength.

Example 13

Total Synthesis of the Inward-Rectifying Potassium Channel Pore IRKI and FRET Analyses of its Interaction with Toxin Ligand Polypeptides for total chemical synthesis and chromophore labeling of channel pore IRKI are designed based on the three-dimensional structure of the homologous potassium channel of *Streptomyces lividans* (Dole, et al., *Science* (1998) 280:69–77) and to accommodate toxin binding (MacKinnon, et al., *Science* (1998) 280:106). The polypeptides are constructed so that the N-terminal domain entails the outer helix and the C-terminal domain engenders the inner and pore helices. A glycine residue is engineered into position 120 of IRK 1 to ease chemical ligation. Polypeptides for stepwise synthesis and the ligation product of IRK1 are depicted in the following SEQ ID NOS:

IRK1 N-terminal domain polypeptide (SEQ ID NO:11):

MTIFITAFLG SWFFFGLLWY AVAYIHKDLP EFHPSANHTG

IRK1 C-terminal domain polypeptide (SEQ ID NO:12):

CVENINGLTS AFLFSLETQV TIGYGFRCVT EQCATAIFLL

IFQSILGVII NSFMCGAILA KISRPK

Total Synthetic/Ligated IRK1 polypeptide (SEQ ID NO:13):

MTIFITAFLG SWFFFGLLWY AVAYIHKDLP EFHPSANHTG

CVEAINSLTD AFLFSLETQV TIGYGFRCVT EQCATAIFLL

IFQSILGVII NSFMCGAILA KISRPK

The N-terminus of IRK1 (76–120) (SEQ ID NO:11) is synthesized on a PAM thioester generating resin using an in situ neutralization protocol for Boc chemistry using established side-chain protection strategies. A TTHA-coumarin label is attached to the N-terminus of the N-terminal polypeptide following the procedures described above. The polypeptides are deprotected and simultaneously cleaved from the resin by treatment with HF in the presence of 10% v/v p-cresol for 1 hour at 0° C. The crude polypeptide is precipitated and washed three times in cold ether, and dissolved in neat TFA. The TFA is removed on a Rotavap and the residue taken up in neat TFE to form a clear solution. The TFE solution is diluted 10× with 50% aqueous acetonitrile containing 0.1% TFA and lyophilized.

For purification, the crude polypeptide is taken up in neat TFE and diluted with 2 equivalents of 6M guanidinium chloride containing 100 mM acetate (pH 4). The material is loaded onto an 1 inch ID C4 prep HPLC column equilibrated at 45% buffer B (100% acetonitrile containing 0.1% TFA). After running the column isocratically at 45% C at 10 ml/min for 15 minutes, the peptide is eluted in a gradient from 45% to 75% C in 60 minutes at 10 ml/min.

Fractions are collected every 5 ml and analyzed for purity by ES/MS.

The C-terminus of IRK1 (120–186) (SEQ ID NO:12) is synthesized on amide generating MBHA resin using an in situ neutralization protocol for Boc chemistry using established side-chain protection strategies. The peptides are deprotected and simultaneously cleaved from the resin by treatment with HF in the presence of 10% v/v p-cresol for one hour at 0° C. The crude peptide is precipitated and washed three times in cold ether, and dissolved in neat TFA. The TFA is removed on a Rotavap and the residue taken up in neat TFE to form a clear solution. The TFE solution is diluted 10× with 50% aqueous acetonitrile containing 0.1% TFA and lyophilized.

For purification, the crude polypeptide is taken up in neat TFE and diluted with 2 equivalents of 6M guanidinium chloride containing 100 mM acetate (pH 4). The material is loaded onto a 1 inch ID C4 prep HPLC column equilibrated at 65% buffer C (60% isopropanol, 30% acetonitrile, 10% H2O containing 0.1% TFA). After running the column isocratically at 65% buffer C at 10 ml/min for 15 minutes, the peptide is eluted in a gradient from 65% to 95% buffer C in 45 minutes at 10 ml/min. Fractions collected every 5 ml are reconstituted with lanthanide ion chelate (e.g., terbium chelate—$Tb^{3+}Cl_3$) and analyzed for purity by ES/MS.

For lipid-matrix assisted membrane chemical ligation in CLP matrix forming lipid, 50 μg N-terminal polypeptide (SEQ ID NO:11) and 60 μg C-terninal polypeptide (SEQ ID NO:12) are dissolved in 3 μl DMSO and added to 42.6 mg MO and 1 μl thiophenol in an Eppendorf centrifuge tube. The mixture is spun for 2.5 hours until formation of a clear phase observed. The reaction is left overnight. MALDI analysis shows the presence of ligation product (SEQ ID NO:13) by mass analysis.

Figure 10:
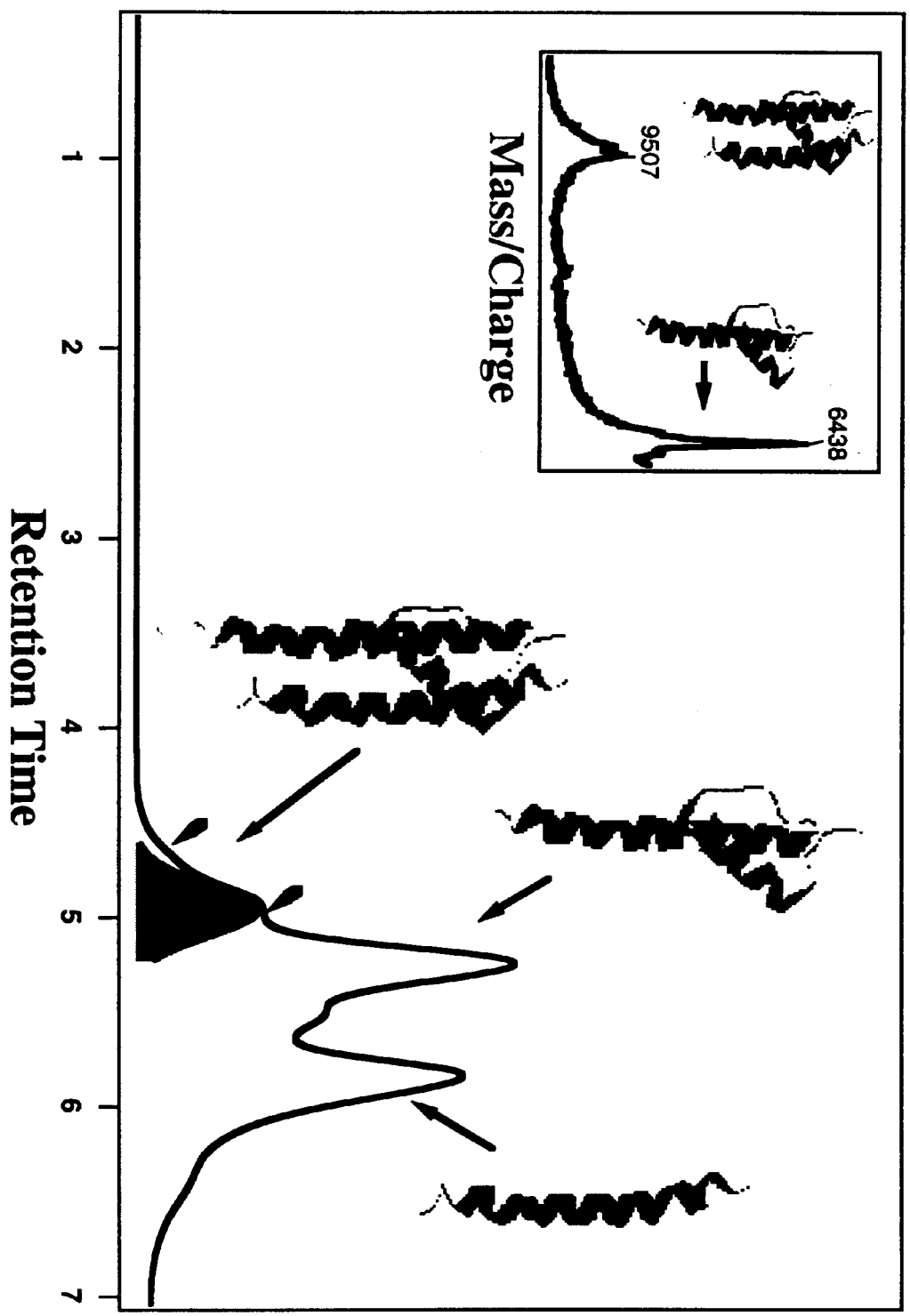
FIG. 10 illustrates gel permeation HPLC and mass analysis employing MALDI mass spectrometry of *S. livdans* potassium ion channel (KCSA) precursor N-terminal and C-terminal peptides and ligation product following initiation of and overnight ligation in 1-monooleoyl-racglycerol (C18:1, {cis}-9) (MO) cubic lipidic phase (CLP).

Agitoxin ligand (SEQ ID NO:14) designed to bind to the synthetic IRK1 potassium channel is constructed by chemical synthesis taking into consideration the known channel-toxin interaction sites (Doyle, et al., supra; Savarin, et al., *Biochemistry* (1998) 37:5407–5416). A TEXAS RED label is attached to the C-terminal lysine (residue 39) of agitoxin2 (SEQ ID NO:14) following the procedure described in Example 8. The toxin, IRK1 Agitoxin2 Ligand (SEQ ID NO:14), has the following amino acid sequence:

GVPINVSCTG SPQCIKPCKD AGMRFGKCMN RKCHCTPK

The IRK1 toxin peptide is purified by reverse phase HPLC and folded in 2M guanidinium chloride/100 mM Tris, pH 8.6 containing 8 mM cystine/1 mM cysteine followed by preparative reversed-phase HPLC (25–45% B (isopropanol/acetonitrile 2:1) over 45 minutes at 10 ml/min.

Lyophilized IRK1 toxin is then mixed with the CLP matrix containing the lanthanide ion chelate labeled IRK1 membrane polypeptide (SEQ ID NO:13) and spun for equilibration. The ciear, red gel is then applied to a solid sample holder in a Spex-Fluorolog 3 Fluorimeter and the presence of energy transfer is determined by obtaining the 330 nm-excited fluorescence spectrum of the gel between 450 and 600 nm. An aqueous solution of a small-molecule antagonist is then mixed into the CLP and displacement of the toxin from the channel is observed by a decrease in fluorescence.

Example 14

Chemical Ligation of CLP-Incorporated Potassium Ion Channel of S. livdans.

Peptides utilized for the membrane spanning domains of the potassium ion channel pore of *Streptomyces lividans* (KCSA) are designed based on the known KCSA structure (Doyle, et al., *Science* (1998) 280:69–77). The N-terrninal transmembrane domain (SEQ ID NO:15) utilized for ligation is designed to entail the outer helix, whereas the C-terminal transmembrane domain (SEQ ID NO:16) design engenders the inner and pore helices. This ligation design yields a truncated version of the naturally occurring KCSA to isolate fimctionality of the membrane spanning domain form extracellular portions. Also, a cysteine is incorporated in place of Ala54 of the naturally occurring KCSA (160 residues) during peptide synthesis to introduce a chemoselective group amenable to native chemical ligation, for the purpose of generating a native peptide backbone at the ligation site. Sequences of the N-terminal, C-terminal and final ligation product are depicted below.

KCSA Potassium Channel N-terminal Segment (SEQ ID NO:15):

ALHWRAAGAA TVLLVIVLLA GSYLAVLAER G

KCSA Potassium Channel C-terminal Segment (SEQ ID NO:16):

CPGAQLITYP RALWWSVETA TTVGYGDLYP
VTLWGRLVAV VVMVAGITSF GLVTAALAT

KCSA Potassium Channel Ligation Product (SEQ ID NO:17):

ALHWRAAGAA TVLLVIVLLA GSYLAVLAER
GCPGAQLITY PRALWWSVET ATTVGYGDLY
PVTLWGRLVA VVVMVAGITS FGLVTAALAT

The N-terminus of KCSA (residues 23–53) (SEQ ID NO:15) is synthesized on a PAM thioester generating resin using an in situ neutralization protocol for Boc chemistry and established side-chain protection strategies. The peptides are deprotected and simultaneously cleaved from the resin by treatment with HF in the presence of 10% v/v p-cresol for 1 hour at 0° C. The crude peptide is precipitated and washed 3× in cold ether, and dissolved in neat TFA. The TFA is removed on a Rotavap and the residue taken up in neat TFE to form a clear solution. The TFE solution is diluted 10× with 50% aqueous acetonitrile containing 0.1% TFA and lyophilized. For purification, the crude peptide (SEQ ID NO:15) is taken up in neat TFE and diluted with 2 equivalents of 6M guanidinium chloride containing 100 mM acetate (pH 4). The material is loaded onto a 1 in. ID C4 prep HPLC column equilibrated at 45% buffer C (60% isopropanol, 30% acetonitrile, 10% $H_2O$ containing 0.1% TFA). After running the column isocratically at 45% buffer C at 10 ml/min for 15 minutes, the peptide is eluted in a gradient from 45% to 75% buffer C in 60 minutes at 10 ml/min. Fractions collected every 5 ml and analyzed for purity by ES/MS.

The C-terminus of KCSA (residues 54–118) (SEQ ID NO:16) is synthesized on amide generating MBHA resin using an in situ neutralization protocol for Boc chemistry and established side-chain protection strategies. The peptide is deprotected and simultaneously cleaved from the resin by treatment with HF in the presence of 10% v/v p-cresol for 1 hour at 0° C. The crude peptide is precipitated and washed 3× in cold ether, and dissolved in neat TFA. The TFA is removed on a Rotavap and the residue taken up in neat TFE to form a clear solution. The TFE solution is diluted 10× with 50% aqueous acetonitrile containing 0.1% TFA and lyophilized. For purification, the crude peptide (SEQ ID NO:16) is taken up in neat TFE and diluted with 2 equivalents of 6M guanidinium chloride containing 100 mM acetate (pH 4). The material is loaded onto a 1 inch ID C4 prep HPLC column equilibrated at 65% buffer C. After running the column isocratically at 65% buffer C at 10 ml/min for 15 minutes, the peptide eluted in a gradient from 65% to 95% buffer C in 45 minutes at 10 ml/min. Fractions collected every S ml and analyzed for purity by ES/MS.

For incorporation into a CLP matrix, 50 mg of MO is dissolved in 2 ml (2:1 chloroform/methanol). 2 mg of DOPC is added to the solution. 70 μg N-terminal peptide (SEQ ID NO:15) and 90 μg C-terminal peptide (SEQ ID NO:16) are dissolved in 150 µl TFE and heated to 60° C. for 30 minutes in a glass vial. Both solutions are then combined. The combined solution is dried by blowing off solvent with argon gas and leaving under vacuum overnight to get a milky film. 35 µl Sodium phosphate (100 mM, pH 7.5) and 0.5 µl thiophenol are added to the dry film. The mixture is spun for 2.5 hours until formation of a clear phase is observed. The reaction is left overnight. The next day, 100 µl TFE containing 20% β-mercaptoethanol is added to the phase. The phase is briefly vortexed and spun in a tabletop centrifuge for 10 minutes. Then 150 pl buffer C (6:3:1 isopropanol/acetonitrile/H$_2$O containing 0.1% TFA) in 0.1% aqueous TFA is added. Residual precipitate is dissolved in neat TFA. The solution is filtered and a spatula tip of TCEP is added to reduce the sample. Finally, the dissolved reaction mixture is injected into a GPC (gel permeation chromatography) column filled with divinylbenzene equilibrated in buffer C. The elutant peaks are collected and the fractions analyzed by MALDI mass spectrometry. (See FIG. 10).

Example 15

Chemical Ligation of Micelle-Incorporated HIV VPU Ion Channel

Total chemical synthesis of the HIV vpu ion channel utilizing native chemical ligation is performed as follows. The N-terminal peptide (vpu residues 1–39) (SEQ ID NO:18): MEPIQLAIVA LVVAIIIAIV VWSIVIIYRK ILRQRKID is synthesized on thioester-generating resin, and the C-terminal peptide (vpu residues 40–81) (SEQ ID NO:19): CLIDRLIERA EDSGNESEGE ISALVEMGVE MGHHAPWDID DL, on standard resin-OCH$_2$ PAM. The peptides are combined by native chemical ligation at a non-native cysteine residue suitably introduced during peptide synthesis and positioned in the center of the protein. A 2 mM solution of the N-terminal peptide is prepared in a micelle-forming ligation buffer containing 250 mM phosphate buffer (pH 7.5) containing 8 M urea, 250 mM DPC and 1 µl thiophenol. To this solution, a 1.2 fold molar excess of C-terminal peptide is added. The solution is stirred for 3 hours at room temperature in an Eppendorf tube. The progress of the ligation is monitored by analytical reversed-phase HPLC. The reaction is completed after 3 hours, and represents greater than 95% yield of the initial reaction components. Ligated membrane polypeptide is isolated using semi-preparative reversed-phase HPLC and the identity of ligated product confirmed by mass analysis employing electrospray mass spectrometry to have a mass corresponding to expected sequence as follows (SEQ ID NO:20):

MEPIQLAIVA LVVAIIIAIV VWSIVIIYRK ILRQRKIDCL

IDRLIERAED SGNESEGEIS ALVEMGVEMG HHAPWDIDDL

Figure 9:
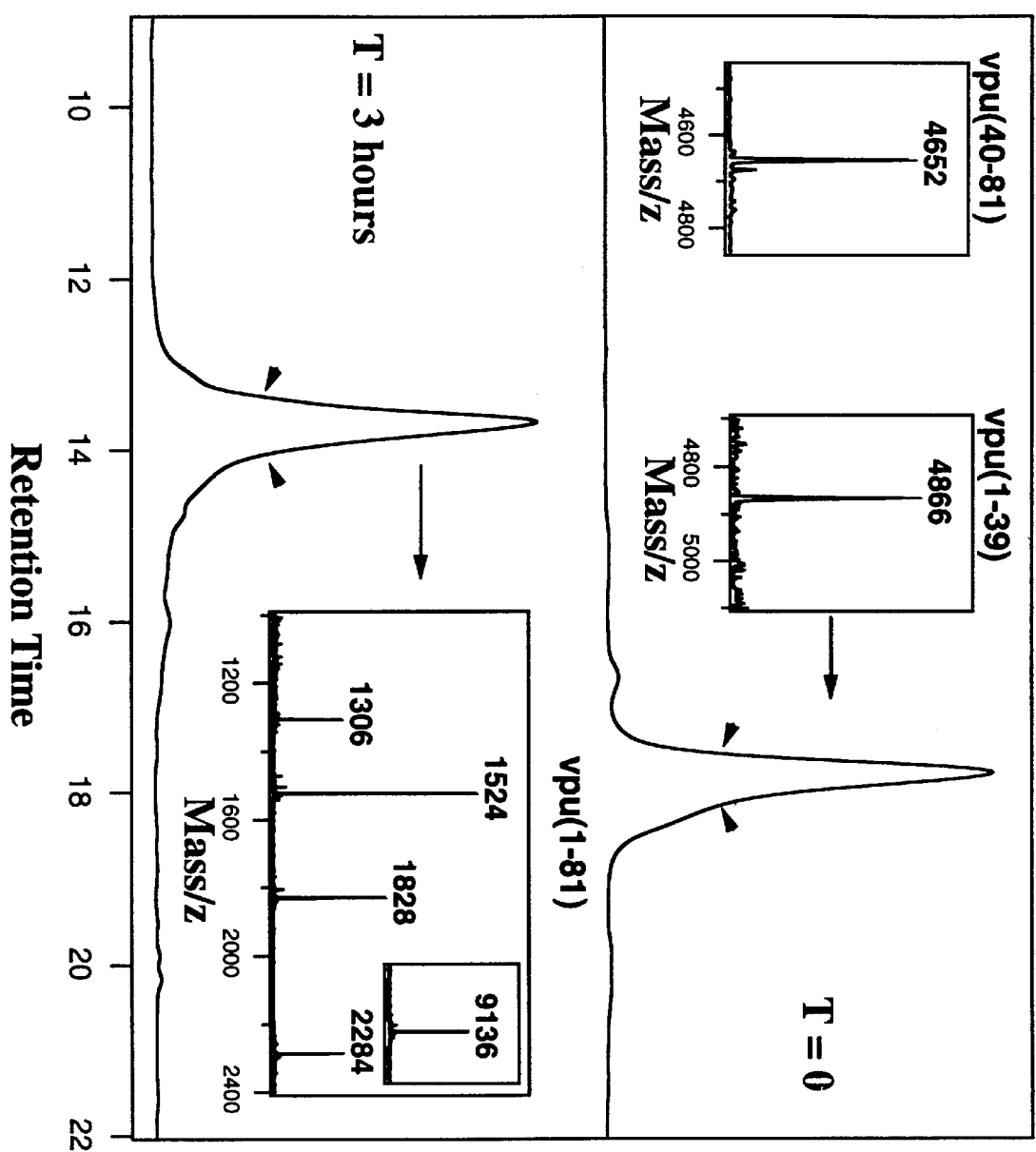
FIG. 9 illustrates reversed-phase HPLC and mass analysis employing electrospray mass spectrometry of HIV vpu ion channel precursor N-terminal and C-terminal peptides at time=0 hours and ligation product at time=3 hours following initiation of ligation in dodecylphosphocholine (DPC) micelle.

See FIG. 9.

Example 16

Chemical Ligation of Micelle-Incorporated Influenza M2 Ion Channel

Total chemical synthesis of the influenza M2 ion channel is prepared as described in Example 15 using the following M2 peptides for micelle-mediated ligation. The N-terminal peptide synthesized on thioester-generating resin has the following sequence(SEQ ID NO:21):

MSLLTEVETP IRNEWGSRCN DSSDPLVVAA SIIG-ILHLIL WILDRLFFK which corresponds to M2 residues 1–49. The C-terminal peptide synthesized on standard resin-OCH$_2$ PAM has the following sequence (SEQ ID NO:22): CIYRFFEHGL KRGPSTEGVP ESMREEYRKE QQSAVDADDS HFVSIELE, which corresponds to M2 residues 50–97. As with the HIV vpu ion channel, the reaction is completed after 3 hours with greater than 95% of the initial peptides being ligated in the reaction to yield the ligated product (M2 residues 1–97). Semi-preparative reversed-phase HPLC and mass analysis employing electrospray mass spectrometry confirmed a ligation product having a mass corresponding to the expected sequence as follows (SEQ ID NO:23):

MSLLTEVETP IRNEWGSRCN DSSDPLVVAA SIIG-ILHLIL

WILDRLFFKC IYRFFEHGLK RGPSTEGVPE SMREEYRKEQ

QSAVDADDSH FVSIELE

Analytical ultra centrifugation of the M2 ligation product incorporated into DPC micelles demonstrates that M2 oligomerizes into tetramers.

Example 17

Total Chemical Synthesis and On-Resin Labeling of Human IL-8 Chemokines and FRET Analysis of Dimerization in Solution Human IL-8 (hIL-8) is a member of the alpha (CXC) chemokine family and its dimerization properties have been well studied (Rajaratham, et al. (1997) *Methods in Enzymology* 287:89–105). The hIL-8 is synthesized and labeled on-resin with a FRET pair to characterize dimerization properties in solution and for assays with its membrane polypeptide receptors CXCR1 and CXCR2. A FRET pair TTHA-cs124-Tb$^{3+}$ label (donor) and TAMRA (acceptor) is an example of a labeling system chosen as suitable for this purpose.

Peptides required for the total chemical synthesis and fluorescent on-resin labeling of human IL-8 are designed using the published amino acid sequence of this protein. For synthesis and labeling design, an additional lysine residue is added onto the C-terminus for on-resin attachment of the fluorescent probe, and a cysteine ligation site is selected in the middle of the sequence, resulting in two polypeptides of 33 and 40 amino acids.

hIL-8 (1–33) N-terminal peptide (SEQ ID NO:24):
SAKELRCQCI KTYSKPFHPK FIKELRVIES GPH hIL-8 (34–73) C-terminal peptide (SEQ ID NO:25):
CANTEIIVKL SDGRELCLDP KENWVQRVVE KFLKRAENSK Synthetic full length hIL-8 (1–73) (SEQ ID NO:26):
SAKELRCQCI KTYSKPFHPK FIKELRVIES GPH-CANTEII

VKLSDGRELC LDPKENWVQR VVEKFLKRAE NSK

The N-terminus thioester peptide of hIL-8 (1–33) is synthesized, deprotected and cleaved as described above, see e.g. Example 13. To purify, the crude peptide is first dissolved in 6M guanidinium chloride/0.1 M sodium acetate, pH 4.0, then loaded onto a C4 reverse phase preparative column equilibrated in 10% buffer B (100% acetonitrile containing 0.1% TFA). The guanidinium was eluted by running isocratically for 15 minutes at 10% buffer B at 13 mL/min. A gradient of 30% to 50% in 60 minutes is used to elute off the peptide. Fractions are collected every 6 mL, analyzed for purity by ES/MS, then lyophilized.

The acceptor-labeled C-terminal peptide hIL-8 (34–73-TAMRA) is synthesized on MBHA resin and labeled as described in Example 8 using 5-(and-6)-carboxytetramethyl rhodamine, succinimidyl ester. The polypeptide is then deprotected, cleaved and purified in a similar manner to the N-terminal peptide. Donor labeled C-terminal peptide hIL-8-TTHA-cs124 is prepared as follows. The Fmoc side chain on lysine 73 is removed by 20% piperidine (2×5 minutes) then washed well with DMF. 10 Equivalents of the TFA salt of TTHA is dissolved in 0.5 M HBTU (1:1 molar ratio of TTHA to HBTU), neutralized with 3.5 molar equivalents of DIEA, then added to the resin. This is allowed to couple for 3 hours, until the ninhydrin looks clear. To couple the cs124 to the TTHA on-resin, one equivalent of HBTU per TTHA is added to the resin with 4 equivalents of DIEA and allowed to activate for 1 minute. To the activated resin, 10 molar equivalents of cs124 dissolved in DMF are added and coupled for 3 hours. Excess cs124 is washed away with DMF and the resin is cleaved in HF as described above. The labeled C-terminal peptide hIL-8 (34–73-TTHA-cs124) is purified as described above.

Chemical ligation of the purified N-terminal peptide with each of the labeled purified C-terminal peptides is performed in solution (6 M guanidinium chloride/0.1 M sodium phosphate, pH 7.0, 1 mM peptide) with 0.1% thiophenol as a catalyst. Reaction is complete after 16 hours. Both ligation products are treated with β-mercaptoethanol (20%) at pH 8.6 for 20 minutes to remove any remaining DNP protecting groups on the histidine residues. The pH of the solution is dropped to 4.0, TCEP is added to reduce any disulfides and the reaction mix is loaded on the C4 reverse phase semi-prep column in 10% buffer B. Ligation product is eluted off using a gradient of 30 to 50% buffer B over 60 minutes. Fractions of 1.5 mL are collected, analyzed by ES-MS for purity, then lyophilized.

The TAMRA-labeled hIL-8 polypeptide is folded by first dissolving the lyophilized ligation product in 6 M guanidinium chloride/0. 1 M Tris, pH 8.0, then diluting down to 2 M with 0.1 M Tris, pH 8.0. Final peptide concentration is 1 mg/ML. A redox buffer of 8 mM cysteine and 1 mm cystine is included to assist disulfide shuffling. After 16 hours, the folding reaction is complete. This folded product is purified by RP-HPLC as described above. Fractions containing desired product are identified by ES-MS. A loss of 4 amu confirms the presence of two disulfide bridges and the subsequent loss of 4 protons. The folded product is lyophilized and stored at −20° C. until use. The TTHA-cs124 labeled hIL-8 polypeptide is folded in a similar manner.

Folded hIL-8 (1–73-TTHA-cs124) is dissolved in 20 mM Bis Tris Propane, pH 6.5 and reconstituted with 3 equivalents of TbC13. The emission spectra of the protein is collected using an excitation wavelength of 342 nm and shows strong metal emission bands at 488, 543 and 583 nm, typical of $Tb^{3+}$ emission. Folded hIL-8 (1–73-TAMRA) is also dissolved in 20 mM Bis Tris Propane, pH 6.5 and possesses a typical rhodamine emission centered at 577 nm when excited at 553 nm.

Distance between the donor and acceptor labels in a protein complex can be determined from the measured fluorescent lifetimes according to the following equations (Biological Spectroscopy by I. D. Campbell and R. A. Dwek (1984), Benjamin/Cummings Publishing Company, Inc. PP. 114–115.). The efficiency of energy transfer (E) between the two probes is determined by comparing the lifetime of the donor ($\tau_D$) to the lifetime of the donor in the presence of the acceptor ($\tau_{DA}$) using this equation, $E=1-(\tau_{DA}/\tau_D)$. This efficiency is then related to the Forster distance ($R_o$) to determine the average distance (R) between the two labels using this equation, $R=R_o\{(1-E)/E\}^{1/6}$.

Equal concentrations (30 µM) of the donor, hIL-8 (1–73-TTHA-cs124-$Tb^{3+}$), and the acceptor, hIL-8 (1–73-TAMRA) are mixed together and the lifetime at 488 nm is measured. At this concentration, a large portion of the protein will be dimerized in solution as the dimerization constant is ~10 µM. The decay curve exhibits bi-exponential decay. The major component of this decay possesses a shorter lifetime of 0.22 ms and corresponds to the lifetime of the complex between donor and acceptor (TDA). This decrease in the fluorescent lifetime of the donor emission is due to fluorescence resonance energy transfer, FRET, from the donor to the acceptor.

The minor component of the decay has a lifetime of ~1 ms and corresponds to the monomeric donor protein, or the donor protein in complex with itself. The loss of emission over time at 570 nm is also measured and shows a single phase decay with a lifetime of 0.24 ms. At this wavelength, only the decay of the acceptor emission resulting from FRET is observed. This lifetime is similar to that determined at 488 nm. Finally, the decay of the fluorescence emission at 488 nm of the donor alone (30 µM) is monitored over time after excitation at 342 nm. This decay curve exhibits mono-exponential decay, with a calculated lifetime of 0.94 ms (ED).

Using the measured lifetimes and the equations described above, an efficiency of energy transfer (E) of 75% and a distance (R) of ~50 Å is observed. This is a reasonable estimate of distance based on the previously determined NMR structure of the complex. The distance between the two C-termini in this structure is 40 Å. If the additional lysine side chains are considered, an estimate of 50 Å seems reasonable. These results demonstrate that the proteins are folded and forming dimers in solution. These results also further demonstrate the advantages of employing on-resin labeling for providing the specificity, purity and yield to conduct highly sensitive FRET analyses.

Example 18

Micelle-Mediated Chemical Ligation of emrE Transporter

Micelle-mediated chemical ligation is applied for the total chemical synthesis of the emrE transport protein (SEQ ID NO:27):

MNPYIYLGGA ILAEVIGTTL MKFSEGFTRL WPS-VGTIICY

CASFWLLAQT LAYIPTGIAY AIWSGVGIVL ISLLSWGFFG

QRLDLPAIIG MMLICAGVLI INLLSRSTPH

The N-terminal emrE peptide segment 1(SEQ ID NO:28): MNPYIYLGGA ILAEVIGTTL MKFSEGFTRL WPSVGTIICY, and middle emrE peptide segment 2 (SEQ ID NO:29): C(Acm) ASFWLLAQT LAY AIWSGVGIVL ISLLSWGFFG QRLDLPAIIG MMLI are synthesized on thioester-generating resin and the C-terminal emrE peptide segment 3 (SEQ ID NO:30): CAGVLI INLLSRSTPH, on standard resin MBHA resin. 3.5 mg each of emrE peptide segments 2 thioester and emrE peptide segment 3 are jointly dissolved in 50 µl TFE and 350 µg water. 10 mg DPC powder are added. The clear solution is frozen in liquid nitrogen, and lyophilized for 5 hours, yielding a micelle matrix of DPC interspersed with peptide. 400 µl 200 mM Phosphate buffer (pH 7.5) containing 8 M urea and 4 µl thiophenol are added to the lipid matrix, resulting in a clear solution of the peptide segments. After 2 days of ligation, the ligation mix is added to a solution of 2 ml TFE, 2 ml water containing 20% β-mercaptoethanol and incubated for 20 minutes. The solution is acidified with a solution of 15 mg/ml TCEP in 20% aqueous acetic acid and loaded onto a semi-preparative reverse-phase HPLC column. Fractions containing the desired first ligation product (ligation product of emrE segments 2+3) are identified by electrospray mass spectrometry and lyophilized overnight.

To remove the N-terminal "Acm" (acetamidomethyl) group, the resulting lyophilized/ligated emrE peptide segment (ligation product of emrE segments 2+3, ~2 mg) is dissolved in 50 μl TFE and 350 μl 0.5M acetic acid. The Acm group is then removed by treatment with a 1.5 molar excess (relative to the total cysteine concentration) of a Hg(acetate)$_2$ solution for 1 hour. The solution is then made 20% in β-mercaptoethanol, loaded onto an analytical reverse-phase HPLC column and purified with a step gradient. Fractions containing the desired ligated product were identified by electrospray mass spectrometry and lyophilized overnight.

Equal amounts of the resulting deprotected ligated emrE peptide segment (ligation product of emrE segments 2+3) and the final emrE segment 1 thioester are jointly dissolved in 50 μl TFE and 350 μl water. 5 mg DPC powder is added. The clear solution is frozen in liquid nitrogen, and lyophilized for several hours, yielding a micelle matrix of DPC interspersed with peptide. 200 μl 250 mM Phosphate buffer (pH 7.5) containing 8 M urea and 2 μl thiophenol are added to the lipid matrix, resulting in a clear solution of the peptide segments. After 1 day of ligation, the ligation mix is added to a solution of 1.4 ml TFE, 0.7 ml β-mercaptoethanol, 0.7 ml piperidine and 1.4 ml water, and incubated for 20 minutes to remove any remaining protecting groups. The solution is acidified with a solution of 15 mg/ml TCEP in 20% aqueous acetic acid, loaded onto a semi-preparative reverse-phase HPLC column and purified with a linear gradient. Fractions containing the desired ligated product (SEQ ID NO:27) are identified by electrospray mass spectrometry and lyophilized overnight.

All publications and patent applications mentioned in this specification are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A method for chemoselective chemical ligation of a membrane polypeptide, said method comprising contacting under chemoselective chemical ligation conditions:
   (i) a polypeptide comprising a first amino acid having an unprotected reactive group, wherein said polypeptide is incorporated in a lipid matrix; with
   (ii) a ligation label comprising a second an amino acid having an unprotected reactive group, wherein said second amino acid is capable of chemoselective chemical ligation with said first amino acid;
wherein said contacting of said polypeptide with said ligation label causes a covalent bond to be formed between said unprotected reactive groups of said first and second amino acids.

2. The method of claim 1, wherein said chemoselective chemical ligation is selected from the group consisting of native chemical ligation, oxime-forming ligation, thioester-forming ligation, thioether-forming ligation, hydrazone-forming ligation, thiazolidine-forming ligation, and oxazolidine-forming ligation.

3. The method of claim 1, wherein said lipid matrix comprises lipid molecules capable of forming a lyotropic phase.

4. The method of claim 3, wherein said lipid matrix is selected from the group consisting of a planner bilayer membrane, a liposome, a micelle, or a cubic lipidic phase matrix.

5. The method of claim 1, wherein said membrane polypeptide is folded.

6. The method of claim 1, wherein said membrane polypeptide is an integral membrane polypeptide.

7. The method of claim 6, wherein said integral membrane polypeptide is a transmembrane polypeptide.

8. The method of claim 7, wherein said transmembrane polypeptide is a receptor.

9. The method of claim 1, wherein said ligation label comprises one or more amino acids.

10. The method of claim 9, wherein said ligation label comprises a peptide.

11. The method of claim 10, wherein said peptide is a water soluble peptide.

12. The method of claim 10, wherein said peptide is a lipid soluble peptide.

13. The method of claim 10, wherein said peptide comprises a polypeptide.

14. The method of claim 13, wherein said polypeptide is a membrane polypeptide.

15. The method of claim 9, wherein said peptide comprises an unnatural amino acid.

16. The method of claim 15, wherein said unnatural amino acid comprises a chromophore.

17. The method of claim 16, wherein said chromophore is an acceptor moiety of an acceptor-donor resonance energy transfer pair.

18. The method of claim 16, wherein said chromophore is a donor moiety of an acceptor-donor resonance energy transfer pair.

19. A composition comprising an integral membrane polypeptide embedded in a lipid matrix and at least one non-naturally occurring amino acid comprising a unprotected reactive group capable of chemoselective chemical ligation with a ligation label having a compatible unprotected reactive group.

20. The composition of claim 19, wherein said integral membrane polypeptide includes a first amino acid residue covalently linked to a second amino acid residue through a unnatural backbone bond selected from the group consisting of oxime, thioester, thioether, hydrazone, thiazolidine, and oxazolidine.

21. The composition of claim 19, wherein said membrane polypeptide is an integral membrane polypeptide.

22. The composition of claim 21, wherein said integral membrane polypeptide is a transmembrane polypeptide.

23. The composition of claim 22, wherein said transmembrane polypeptide comprises one or more lipid membrane anchoring domains of a receptor.

24. The composition of claim 22, wherein said transmembrane polypeptide comprises one or more lipid membrane anchoring domains of an ion channel.

25. The composition of claim 19, wherein said membrane polypeptide comprises an unnatural amino acid comprising a detectable label.

26. A composition comprising a membrane polypeptide embedded in a lipid matrix, said membrane polypeptide having at least two amino acid residue covalently joined through an unnatural backbone bond.

27. The composition of claim 26, wherein said unnatural backbone bond is selected from the group consisting of oxime, thioester, thioether, hydrazone, thiazolidine, and oxazolidine.

28. A method for chemoselective chemical ligation of a membrane polypeptide and a ligation label, said method comprising admixing in a ligation buffer:

(i) a membrane polypeptide comprising a first amino acid having an unprotected reactive group, wherein said polypeptide de is incorporated in a lipid matrix; and (ii) a ligation label comprising a second amino acid having an unprotected reactive group, wherein said second amino acid is capable of chemoselective chemical ligation with said first amino acid;

said ligation buffer comprising as components a micelle forming lipid matrix, a chaotrope, a buffer, and a chemical ligation catalyst that catalyzes the formation of a covalent bond between said unprotected reactive groups of said first and second amino acids.

29. The method of claim 28, wherein said chemoselective chemical ligation is selected from the group consisting of native chemical ligation, oxime-forming ligation, thioester-forming ligation, thioether-forming ligation, hydrazone-forming ligation, thiazolidine-forming ligation, and oxazolidine-forming ligation.

30. The method of claim 28, wherein said micelle forming lipid matrix is dodecylphosphocholine.

31. The method of claim 28, wherein said chaotrope is selected from the group consisting of urea and guanidinium chloride.

32. The method of claim 29, wherein said chemoselective chemical ligation is native chemical ligation.

33. The method of claim 32, wherein said chemical ligation catalyst is thiophenol.

* * * * *

SEQUENCE LISTING

```
<160> NUMBER OF SEQ ID NOS: 30

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence:Synthetic

<400> SEQUENCE: 1

Thr Gly Arg Pro Glu Trp Ile Trp Leu Ala Leu Gly Thr Ala Leu Met
  1               5                  10                  15

Gly Leu Gly Thr Leu Tyr Phe Leu Val Lys Gly Met Gly Val Ser Asp
             20                  25                  30

Pro Asp Ala Lys Lys
         35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence:Synthetic

<400> SEQUENCE: 2

Cys Gly Arg Pro Glu Trp Ile Trp Leu Ala Leu Gly Thr Ala Leu Met
  1               5                  10                  15

Gly Leu Gly Thr Leu Tyr Phe Leu Val Lys Gly Met Gly Val Ser Asp
             20                  25                  30

Pro Asp Ala Lys Lys
         35

<210> SEQ ID NO 3
<211> LENGTH: 45
<212> TYPE: PRT
<213> ORGANISM: Artificial Sequence
<220> FEATURE:
```

```
<223> OTHER INFORMATION: Description of Artificial Sequence:Synthetic

<400> SEQUENCE: 3

Gly Lys Gly Tyr Ile Glu Gly Arg Cys Gly Arg Pro Glu Trp Ile Trp
 1               5                   10                  15

Leu Ala Leu Gly Thr Ala Leu Met Gly Leu Gly Thr Leu Tyr Phe Leu
                20                  25                  30

Val Lys Gly Met Gly Val Ser Asp Pro Asp Ala Lys Lys
            35                  40                  45

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:Synthetic

<400> SEQUENCE: 4

Glu Ala Gln Leu
 1

<210> SEQ ID NO 5
<211> LENGTH: 41
<212> TYPE: PRT
<213> ORGANISM: Artificial Sequence
<220> FEATURE:
<223> OTHER INFORMATION: Description of Artificial Sequence:Synthetic

<400> SEQUENCE: 5

Glu Ala Gln Leu Cys Gly Arg Pro Glu Trp Ile Trp Leu Ala Leu Gly
 1               5                   10                  15

Thr Ala Leu Met Gly Leu Gly Thr Leu Tyr Phe Leu Val Lys Gly Met
                20                  25                  30

Gly Val Ser Asp Pro Ala Lys Lys
            35                  40

<210> SEQ ID NO 6
<211> LENGTH: 332
<212> TYPE: PRT
<213> ORGANISM: Artificial Sequence
<220> FEATURE:
<223> OTHER INFORMATION: Description of Artificial Sequence:Synthetic

<400> SEQUENCE: 6

Met Val Asn Ser Thr His Arg Gly Met His Thr Ser Leu His Leu Trp
 1               5                   10                  15

Asn Arg Ser Ser Tyr Arg Leu His Ser Asn Ala Ser Glu Ser Leu Gly
                20                  25                  30

Lys Gly Tyr Ile Glu Gly Arg Cys Tyr Glu Gln Leu Phe Val Ser Pro
            35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Ile Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125
```

```
Ile Cys Ser Ser Leu Leu Ala Ser Ile Cys Ser Leu Leu Ser Ile Ala
    130                 135                 140

Val Asp Arg Thr Phe Thr Ile Phe Tyr Ala Leu Gln Tyr His Asn Ile
145                 150                 155                 160

Met Thr Val Lys Arg Val Gly Ile Ile Ser Cys Ile Trp Ala Ala
                165                 170                 175

Cys Thr Val Ser Gly Ile Leu Phe Ile Ile Tyr Ser Asp Ser Ser Ala
                180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
    210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
                260                 265                 270

Gln Asn Pro Tyr Cys Val Cys Phe Met Ser His Phe Asn Leu Tyr Leu
                275                 280                 285

Ile Leu Ile Met Cys Asn Ser Ile Ile Asp Pro Leu Ile Tyr Ala Leu
        290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330

<210> SEQ ID NO 7
<211> LENGTH: 39
<212> TYPE: PRT
<213> ORGANISM: Artificial Sequence
<220> FEATURE:
<223> OTHER INFORMATION: Description of Artificial Sequence:Synthetic

<400> SEQUENCE: 7

Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
            20                  25                  30

Lys Gly Tyr Ser Asp Gly Gly
        35

<210> SEQ ID NO 8
<211> LENGTH: 293
<212> TYPE: PRT
<213> ORGANISM: Artificial Sequence
<220> FEATURE:
<223> OTHER INFORMATION: Description of Artificial Sequence:Synthetic

<400> SEQUENCE: 8

Cys Tyr Glu Gln Leu Phe Val Ser Pro Glu Val Phe Val Thr Leu Gly
1               5                   10                  15

Val Ile Ser Leu Leu Glu Asn Ile Leu Val Ile Val Ala Ile Ala Lys
            20                  25                  30

Asn Ile Asp Asn Val Ile Asp Ser Val Ile Cys Ser Ser Leu Leu Ala
        35                  40                  45

Val Ala Asp Met Leu Val Ser Val Ser Asn Gly Ser Glu Thr Ile Ile
    50                  55                  60
```

```
Ile Thr Leu Leu Asn Ser Thr Asp Thr Asp Ala Gln Ser Phe Thr Val
 65                  70                  75                  80

Asn Ile Asp Asn Val Ile Asp Ser Val Ile Cys Ser Ser Leu Leu Ala
                 85                  90                  95

Ser Ile Cys Ser Leu Leu Ser Ile Ala Val Asp Arg Tyr Phe Thr Ile
            100                 105                 110

Phe Tyr Ala Leu Gln Tyr His Asn Ile Met Thr Val Lys Arg Val Gly
        115                 120                 125

Ile Ile Ile Ser Cys Ile Trp Ala Ala Cys Thr Val Ser Gly Ile Leu
    130                 135                 140

Phe Ile Ile Tyr Ser Asp Ser Ser Ala Val Ile Ile Cys Leu Ile Thr
145                 150                 155                 160

Met Phe Phe Thr Met Leu Ala Leu Met Ala Ser Leu Tyr Val His Met
                165                 170                 175

Phe Leu Met Ala Arg Leu His Ile Lys Arg Ile Ala Val Leu Pro Gly
            180                 185                 190

Thr Gly Ala Ile Arg Gln Gly Ala Asn Met Lys Gly Ala Ile Thr Leu
        195                 200                 205

Thr Ile Leu Ile Gly Val Phe Val Val Cys Trp Ala Pro Phe Phe Leu
    210                 215                 220

His Leu Ile Phe Tyr Ile Ser Cys Pro Gln Asn Pro Tyr Cys Val Cys
225                 230                 235                 240

Phe Met Ser His Phe Asn Leu Tyr Leu Ile Leu Ile Met Cys Asn Ser
                245                 250                 255

Ile Ile Asp Pro Leu Ile Tyr Ala Leu Arg Ser Gln Glu Leu Arg Lys
            260                 265                 270

Thr Phe Lys Glu Ile Ile Cys Cys Tyr Pro Leu Gly Gly Leu Cys Asp
        275                 280                 285

Leu Ser Ser Arg Tyr
        290

<210> SEQ ID NO 9
<211> LENGTH: 332
<212> TYPE: PRT
<213> ORGANISM: Artificial Sequence
<220> FEATURE:
<223> OTHER INFORMATION: Description of Artificial Sequence:Synthetic

<400> SEQUENCE: 9

Met Val Asn Ser Thr His Arg Gly Met His Thr Ser Leu His Leu Trp
 1               5                  10                  15

Asn Arg Ser Ser Tyr Arg Leu His Ser Asn Ala Ser Glu Ser Leu Gly
                20                  25                  30

Lys Gly Tyr Ser Asp Gly Gly Cys Tyr Glu Gln Leu Phe Val Ser Pro
            35                  40                  45

Glu Val Phe Val Thr Leu Gly Val Ile Ser Leu Leu Glu Asn Ile Leu
        50                  55                  60

Val Ile Val Ala Ile Ala Lys Asn Lys Asn Leu His Ser Pro Met Tyr
 65                  70                  75                  80

Phe Phe Ile Cys Ser Leu Ala Val Ala Asp Met Leu Val Ser Val Ser
                 85                  90                  95

Asn Gly Ser Glu Thr Ile Ile Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125
```

```
Ile Cys Ser Ser Leu Leu Ala Ser Ile Cys Ser Leu Leu Ser Ile Ala
        130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ile Ser Cys Ile Trp Ala Ala
                165                 170                 175

Cys Thr Val Ser Gly Ile Leu Phe Ile Ile Tyr Ser Asp Ser Ala
                180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
        210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
                260                 265                 270

Gln Asn Pro Tyr Cys Val Cys Phe Met Ser His Phe Asn Leu Tyr Leu
                275                 280                 285

Ile Leu Ile Met Cys Asn Ser Ile Ile Asp Pro Leu Ile Tyr Ala Leu
        290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330

<210> SEQ ID NO 10
<211> LENGTH: 132
<212> TYPE: PRT
<213> ORGANISM: Artificial Sequence
<220> FEATURE:
<223> OTHER INFORMATION: Description of Artificial Sequence:Synthetic

<400> SEQUENCE: 10

Met Leu Thr Ala Ala Val Leu Ser Cys Ala Leu Leu Ala Leu Pro
 1               5                  10                  15

Ala Thr Arg Gly Ala Gln Met Gly Leu Ala Pro Met Glu Gly Ile Arg
                20                  25                  30

Arg Pro Asp Gln Ala Leu Leu Pro Glu Leu Pro Gly Leu Gly Leu Arg
                35                  40                  45

Ala Pro Leu Lys Lys Thr Thr Ala Glu Gln Ala Glu Glu Asp Leu Leu
        50                  55                  60

Gln Glu Ala Gln Ala Leu Ala Glu Val Leu Asp Leu Gln Asp Arg Glu
65                  70                  75                  80

Pro Arg Ser Ser Arg Arg Cys Val Arg Leu His Glu Ser Cys Leu Gly
                85                  90                  95

Gln Gln Val Pro Cys Cys Asp Pro Cys Ala Thr Cys Tyr Cys Arg Phe
                100                 105                 110

Phe Asn Ala Phe Cys Tyr Cys Arg Lys Leu Gly Thr Ala Met Asn Pro
        115                 120                 125

Cys Ser Arg Thr
        130

<210> SEQ ID NO 11
```

<211> LENGTH: 40
<212> TYPE: PRT
<213> ORGANISM: Artificial Sequence
<220> FEATURE:
<223> OTHER INFORMATION: Description of Artificial Sequence:Synthetic

<400> SEQUENCE: 11

```
Met Thr Ile Phe Ile Thr Ala Phe Leu Gly Ser Trp Phe Phe Gly
 1               5                  10                  15

Leu Leu Trp Tyr Ala Val Ala Tyr Ile His Lys Asp Leu Pro Glu Phe
             20                  25                  30

His Pro Ser Ala Asn His Thr Gly
         35                  40
```

<210> SEQ ID NO 12
<211> LENGTH: 66
<212> TYPE: PRT
<213> ORGANISM: Artificial Sequence
<220> FEATURE:
<223> OTHER INFORMATION: Description of Artificial Sequence:Synthetic

<400> SEQUENCE: 12

```
Cys Val Glu Asn Ile Asn Gly Leu Thr Ser Ala Phe Leu Phe Ser Leu
 1               5                  10                  15

Glu Thr Gln Val Thr Ile Gly Tyr Gly Phe Arg Cys Val Thr Glu Gln
             20                  25                  30

Cys Ala Thr Ala Ile Phe Leu Leu Ile Phe Gln Ser Ile Leu Gly Val
         35                  40                  45

Ile Ile Asn Ser Phe Met Cys Gly Ala Ile Leu Ala Lys Ile Ser Arg
     50                  55                  60

Pro Lys
 65
```

<210> SEQ ID NO 13
<211> LENGTH: 106
<212> TYPE: PRT
<213> ORGANISM: Artificial Sequence
<220> FEATURE:
<223> OTHER INFORMATION: Description of Artificial Sequence:Synthetic

<400> SEQUENCE: 13

```
Met Thr Ile Phe Ile Thr Ala Phe Leu Gly Ser Trp Phe Phe Gly
 1               5                  10                  15

Leu Leu Trp Tyr Ala Val Ala Tyr Ile His Lys Asp Leu Pro Glu Phe
             20                  25                  30

His Pro Ser Ala Asn His Thr Gly Cys Val Glu Ala Ile Asn Ser Leu
         35                  40                  45

Thr Asp Ala Phe Leu Phe Ser Leu Glu Thr Gln Val Thr Ile Gly Tyr
     50                  55                  60

Gly Phe Arg Cys Val Thr Glu Gln Cys Ala Thr Ala Ile Phe Leu Leu
 65                  70                  75                  80

Ile Phe Gln Ser Ile Leu Gly Val Ile Ile Asn Ser Phe Met Cys Gly
                 85                  90                  95

Ala Ile Leu Ala Lys Ile Ser Arg Pro Lys
            100                 105
```

<210> SEQ ID NO 14
<211> LENGTH: 38
<212> TYPE: PRT
<213> ORGANISM: Artificial Sequence
<220> FEATURE:

```
<223> OTHER INFORMATION: Description of Artificial Sequence:Synthetic

<400> SEQUENCE: 14

Gly Val Pro Ile Asn Val Ser Cys Thr Gly Ser Pro Gln Cys Ile Lys
 1               5                  10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 15
<211> LENGTH: 31
<212> TYPE: PRT
<213> ORGANISM: Artificial Sequence
<220> FEATURE:
<223> OTHER INFORMATION: Description of Artificial Sequence:Synthetic

<400> SEQUENCE: 15

Ala Leu His Trp Arg Ala Ala Gly Ala Ala Thr Val Leu Leu Val Ile
 1               5                  10                  15

Val Leu Leu Ala Gly Ser Tyr Leu Ala Val Leu Ala Glu Arg Gly
            20                  25                  30

<210> SEQ ID NO 16
<211> LENGTH: 59
<212> TYPE: PRT
<213> ORGANISM: Artificial Sequence
<220> FEATURE:
<223> OTHER INFORMATION: Description of Artificial Sequence:Synthetic

<400> SEQUENCE: 16

Cys Pro Gly Ala Gln Leu Ile Thr Tyr Pro Arg Ala Leu Trp Trp Ser
 1               5                  10                  15

Val Glu Thr Ala Thr Thr Val Gly Tyr Gly Asp Leu Tyr Pro Val Thr
            20                  25                  30

Leu Trp Gly Arg Leu Val Ala Val Val Met Val Ala Gly Ile Thr
        35                  40                  45

Ser Phe Gly Leu Val Thr Ala Ala Leu Ala Thr
    50                  55

<210> SEQ ID NO 17
<211> LENGTH: 90
<212> TYPE: PRT
<213> ORGANISM: Artificial Sequence
<220> FEATURE:
<223> OTHER INFORMATION: Description of Artificial Sequence:Synthetic

<400> SEQUENCE: 17

Ala Leu His Trp Arg Ala Ala Gly Ala Ala Thr Val Leu Leu Val Ile
 1               5                  10                  15

Val Leu Leu Ala Gly Ser Tyr Leu Ala Val Leu Ala Glu Arg Gly Cys
            20                  25                  30

Pro Gly Ala Gln Leu Ile Thr Tyr Pro Arg Ala Leu Trp Trp Ser Val
        35                  40                  45

Glu Thr Ala Thr Thr Val Gly Tyr Gly Asp Leu Tyr Pro Val Thr Leu
    50                  55                  60

Trp Gly Arg Leu Val Ala Val Val Met Val Ala Gly Ile Thr Ser
65                  70                  75                  80

Phe Gly Leu Val Thr Ala Ala Leu Ala Thr
            85                  90
```

```
<210> SEQ ID NO 18
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 18

Met Glu Pro Ile Gln Leu Ala Ile Val Ala Leu Val Val Ala Ile Ile
 1               5                  10                  15

Ile Ala Ile Val Val Trp Ser Ile Val Ile Ile Tyr Arg Lys Ile Leu
            20                  25                  30

Arg Gln Arg Lys Ile Asp
        35

<210> SEQ ID NO 19
<211> LENGTH: 42
<212> TYPE: PRT
<213> ORGANISM: Artificial Sequence
<220> FEATURE:
<223> OTHER INFORMATION: Description of Artificial Sequence:Synthetic

<400> SEQUENCE: 19

Cys Leu Ile Asp Arg Leu Ile Glu Arg Ala Glu Asp Ser Gly Asn Glu
 1               5                  10                  15

Ser Glu Gly Glu Ile Ser Ala Leu Val Glu Met Gly Val Glu Met Gly
            20                  25                  30

His His Ala Pro Trp Asp Ile Asp Asp Leu
        35                  40

<210> SEQ ID NO 20
<211> LENGTH: 80
<212> TYPE: PRT
<213> ORGANISM: Artificial Sequence
<220> FEATURE:
<223> OTHER INFORMATION: Description of Artificial Sequence:Synthetic

<400> SEQUENCE: 20

Met Glu Pro Ile Gln Leu Ala Ile Val Ala Leu Val Val Ala Ile Ile
 1               5                  10                  15

Ile Ala Ile Val Val Trp Ser Ile Val Ile Ile Tyr Arg Lys Ile Leu
            20                  25                  30

Arg Gln Arg Lys Ile Asp Cys Leu Ile Asp Arg Leu Ile Glu Arg Ala
        35                  40                  45

Glu Asp Ser Gly Asn Glu Ser Glu Gly Glu Ile Ser Ala Leu Val Glu
    50                  55                  60

Met Gly Val Glu Met Gly His His Ala Pro Trp Asp Ile Asp Asp Leu
65                  70                  75                  80

<210> SEQ ID NO 21
<211> LENGTH: 49
<212> TYPE: PRT
<213> ORGANISM: Artificial Sequence
<220> FEATURE:
<223> OTHER INFORMATION: Description of Artificial Sequence:Synthetic

<400> SEQUENCE: 21

Met Ser Leu Leu Thr Glu Val Glu Thr Pro Ile Arg Asn Glu Trp Gly
 1               5                  10                  15

Ser Arg Cys Asn Asp Ser Ser Asp Pro Leu Val Val Ala Ala Ser Ile
            20                  25                  30
```

```
Ile Gly Ile Leu His Leu Ile Leu Trp Ile Leu Asp Arg Leu Phe Phe
            35                  40                  45
Lys

<210> SEQ ID NO 22
<211> LENGTH: 48
<212> TYPE: PRT
<213> ORGANISM: Artificial Sequence
<220> FEATURE:
<223> OTHER INFORMATION: Description of Artificial Sequence:Synthetic

<400> SEQUENCE: 22

Cys Ile Tyr Arg Phe Phe Glu His Gly Leu Lys Arg Gly Pro Ser Thr
 1               5                  10                  15

Glu Gly Val Pro Glu Ser Met Arg Glu Glu Tyr Arg Lys Glu Gln Gln
            20                  25                  30

Ser Ala Val Asp Ala Asp Asp Ser His Phe Val Ser Ile Glu Leu Glu
            35                  40                  45

<210> SEQ ID NO 23
<211> LENGTH: 97
<212> TYPE: PRT
<213> ORGANISM: Artificial Sequence
<220> FEATURE:
<223> OTHER INFORMATION: Description of Artificial Sequence:Synthetic

<400> SEQUENCE: 23

Met Ser Leu Leu Thr Glu Val Glu Thr Pro Ile Arg Asn Glu Trp Gly
 1               5                  10                  15

Ser Arg Cys Asn Asp Ser Ser Asp Pro Leu Val Val Ala Ala Ser Ile
            20                  25                  30

Ile Gly Ile Leu His Leu Ile Leu Trp Ile Leu Asp Arg Leu Phe Phe
            35                  40                  45

Lys Cys Ile Tyr Arg Phe Phe Glu His Gly Leu Lys Arg Gly Pro Ser
        50                  55                  60

Thr Glu Gly Val Pro Glu Ser Met Arg Glu Glu Tyr Arg Lys Glu Gln
 65                  70                  75                  80

Gln Ser Ala Val Asp Ala Asp Asp Ser His Phe Val Ser Ile Glu Leu
                85                  90                  95

Glu

<210> SEQ ID NO 24
<211> LENGTH: 33
<212> TYPE: PRT
<213> ORGANISM: Artificial Sequence
<220> FEATURE:
<223> OTHER INFORMATION: Description of Artificial Sequence:Synthetic

<400> SEQUENCE: 24

Ser Ala Lys Glu Leu Arg Cys Gln Cys Ile Lys Thr Tyr Ser Lys Pro
 1               5                  10                  15

Phe His Pro Lys Phe Ile Lys Glu Leu Arg Val Ile Glu Ser Gly Pro
            20                  25                  30

His

<210> SEQ ID NO 25
<211> LENGTH: 40
<212> TYPE: PRT
<213> ORGANISM: Artificial Sequence
<220> FEATURE:
<223> OTHER INFORMATION: Description of Artificial Sequence:Synthetic
```

```
<400> SEQUENCE: 25

Cys Ala Asn Thr Glu Ile Ile Val Lys Leu Ser Asp Gly Arg Glu Leu
  1               5                  10                  15

Cys Leu Asp Pro Lys Glu Asn Trp Val Gln Arg Val Val Glu Lys Phe
                 20                  25                  30

Leu Lys Arg Ala Glu Asn Ser Lys
            35                  40

<210> SEQ ID NO 26
<211> LENGTH: 73
<212> TYPE: PRT
<213> ORGANISM: Artificial Sequence
<220> FEATURE:
<223> OTHER INFORMATION: Description of Artificial Sequence:Synthetic

<400> SEQUENCE: 26

Ser Ala Lys Glu Leu Arg Cys Gln Cys Ile Lys Thr Tyr Ser Lys Pro
  1               5                  10                  15

Phe His Pro Lys Phe Ile Lys Glu Leu Arg Val Ile Glu Ser Gly Pro
                 20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
     50                  55                  60

Phe Leu Lys Arg Ala Glu Asn Ser Lys
 65                  70

<210> SEQ ID NO 27
<211> LENGTH: 110
<212> TYPE: PRT
<213> ORGANISM: Artificial Sequence
<220> FEATURE:
<223> OTHER INFORMATION: Description of Artificial Sequence:Synthetic

<400> SEQUENCE: 27

Met Asn Pro Tyr Ile Tyr Leu Gly Gly Ala Ile Leu Ala Glu Val Ile
  1               5                  10                  15

Gly Thr Thr Leu Met Lys Phe Ser Glu Gly Phe Thr Arg Leu Trp Pro
                 20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
     50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                 85                  90                  95

Gly Val Leu Ile Ile Asn Leu Leu Ser Arg Ser Thr Pro His
            100                 105                 110

<210> SEQ ID NO 28
<211> LENGTH: 40
<212> TYPE: PRT
<213> ORGANISM: Artificial Sequence
<220> FEATURE:
<223> OTHER INFORMATION: Description of Artificial Sequence:Synthetic

<400> SEQUENCE: 28

Met Asn Pro Tyr Ile Tyr Leu Gly Gly Ala Ile Leu Ala Glu Val Ile
```

-continued

```
                1               5                    10                   15
Gly Thr Thr Leu Met Lys Phe Ser Glu Gly Phe Thr Arg Leu Trp Pro
                        20                  25                  30
Ser Val Gly Thr Ile Ile Cys Tyr
                35              40
```

<210> SEQ ID NO 29
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 29

```
Ala Ser Phe Trp Leu Leu Ala Gln Thr Leu Ala Tyr Ala Ile Trp Ser
 1               5                  10                  15
Gly Val Gly Ile Val Leu Ile Ser Leu Leu Ser Trp Gly Phe Phe Gly
                20                  25                  30
Gln Arg Leu Asp Leu Pro Ala Ile Ile Gly Met Met Leu Ile
        35                  40                  45
```

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence:Synthetic

<400> SEQUENCE: 30

```
Cys Ala Gly Val Leu Ile Ile Asn Leu Leu Ser Arg Ser Thr Pro His
 1               5                  10                  15
```